US006878368B2

(12) United States Patent
Ohta et al.

(10) Patent No.: US 6,878,368 B2
(45) Date of Patent: Apr. 12, 2005

(54) COMPOSITION FOR BLENDING TO HAIR TREATING AGENTS AND A HAIR TREATING AGENT

(75) Inventors: Toshio Ohta, Tokyo (JP); Michihiro Aga, Tokyo (JP); Katsuhiro Watanabe, Tokyo (JP)

(73) Assignee: San-Ei Kagaku Co., Ltd., Tokyo (JP)

( * ) Notice: Subject to any disclaimer, the term of this patent is extended or adjusted under 35 U.S.C. 154(b) by 0 days.

(21) Appl. No.: 10/105,234

(22) Filed: Mar. 26, 2002

(65) Prior Publication Data

US 2003/0103923 A1 Jun. 5, 2003

(30) Foreign Application Priority Data

Mar. 29, 2001 (JP) ....................................... 2001-095360
Mar. 29, 2001 (JP) ....................................... 2001-095361
Mar. 30, 2001 (JP) ....................................... 2001-099822
Mar. 30, 2001 (JP) ....................................... 2001-099823

(51) Int. Cl.[7] ............................ A61K 7/06; A61K 7/09

(52) U.S. Cl. ................ 424/70.19; 424/70.1; 424/70.12; 424/70.21; 424/70.22; 424/70.27; 424/70.31

(58) Field of Search ............................ 424/70.1, 70.12, 424/70.19, 70.21, 70.22, 70.27, 70.31, 70.11, 70.6, 70.2

(56) References Cited

U.S. PATENT DOCUMENTS 5,849,272 A * 12/1998 Baba et al. .................. 424/59

* cited by examiner

*Primary Examiner*—Jyothsna Venkat
(74) *Attorney, Agent, or Firm*—Sherman & Shalloway

(57) ABSTRACT

The present invention is provide compositions for blending in hair treating agents which can prepare hair conditioners, hair colorings, waving agents, finishing agents, additives that increase the feeling effects, aromatic material dispersants, refreshers or thickening agents used on preparing hair treating agents easily and by lower cost. Further the present invention provides hair treating agents which are excellent in the features of hair treating agents such as moist feel, slippery feel, rustle feeling, wet look, luster, smooth feel, soft feel, suppleness, good feel, slightly oily feel, bounce, smoothness, less damage of hair, no hardness and no squeak and smooth combing, and which are excellent in functionalities such as easy appliance, well spread, thickening ability and gelling ability of hair colorings, decolorizing ability of decolorizing agents, setting ability of finishing agents, and dispersibility and dissolving ability to aromatic materials and azulenes by containing alcohols.

28 Claims, No Drawings

COMPOSITION FOR BLENDING TO HAIR TREATING AGENTS AND A HAIR TREATING AGENT

FIELD OF THE INVENTION

The present invention relates to compositions for blending in hair treating agents, and also the hair treating agents therefrom. Especially, the present invention relates to compositions to be blended in hair treating agents, and also the present invention relates to the hair treating agents prepared therefrom such as hair conditioners (Including hair treatments and rinses etc.), hair colorings, waving agents, finishing agents, additives that increase the feeling effects, aromatic material dispersants, refreshers, thickening agents used on preparing hair treating agents, deodorizing rinse liquids, intermediate treating agents for permanents and depilatories.

DESCRIPTION OF THE PRIOR ART

Recently, the beauty sense required to hair is becoming more serious, and along with said requirement, the requirement to a heir treating agent is also becoming serious. Therefore, hair treating agents, which are excellent in feels when used such as the moist feel, slippery feel, rustle feeling, wet look (Moisture feel.), luster, smooth feel, soft feel, suppleness, good feel, slightly oily feel, bounce, smoothness, pleasant sense of touch to the hair, no tangle and no twining, less damage of hair, no hardness and no squeak and smooth combing, and which are excellent in functionalities such as easy appliance, well spread, adhesive, moisturizing ability, no drip, easiness of retouching work (retouching workability), conditioning ability (easy hair care.), long-lasting treatment effects, thickening ability and gelling ability of hair colorings, decolorizing ability of decolorizing agents, tight-knit wave, firmly rooted and no uneven wave formation, quick wave formation, less harsh smell (of ammonia) when and after permanent, low irritation to the skin, good appearance of treating agent (for example, high-class pearly appearance, setting ability of finishing agents, and dispersibility and dissolving ability to aromatic materials and azulenes, are more strongly required.

For the purpose to satisfy the above-mentioned requirement of the consumer, hair treating agents such as hair conditioners, hair colorings, waving agents, finishing agents, additives that increase the feeling effects, aromatic material dispersants, refreshers, thickening agents used on preparing hair treating agents, deodorizing rinse liquids, intermediate treating agents for permanents and depilatories, in which various ingredients were contained, have been proposed.

However, at the preparation of the conventional hair treating agents, the processes are complicated and take long time and high cost because each ingredient must be respectively weighed, added and blended, and these processes are considered as a serious problem.

Further, in the conventional hair treating agents, the specific ingredients, for example, fatty esters, surfactants or silicones are blended to the hair treating agents.

However, these compounds are not popular because they have specific chemical structures. Therefore, these materials have a problem that they are difficult to purchase in the market and are expensive. Further, these materials have also a problem that the hair treatments effects are not sufficient.

SUMMARY OF THE INVENTION

The object of the present invention is to provide compositions for blending in hair treating agents, which can prepare hair treating agents including, for example, hair conditioners, hair colorings, waving agents, finishing agents, additives that increase the feeling effects, aromatic material dispersants, refreshers, thickening agents used on preparing hair treating agents, deodorizing rinse liquids, intermediate treating agents for permanents and depilatories], easily and by lower cost. Further, the object of the present invention is to provide the hair treating agents, which are excellent feels when used such as the the moist feel, slippery feel, rustle feeling, wet look (Moisture feel.), luster, smooth feel, soft feel, suppleness, good feel, slightly oily feel, bounce, smoothness, pleasant sense of touch to the hair, no tangle and no twining, less damage, no hardness and no squeak and smooth smooth combing, and which are excellent in functionalities such as easy appliance, well spread, adhesive, moisturizing ability, no drip, easiness of retouching work (retouching workability), conditioning ability (easiness of hair care.), durability of treatment effects, thickening and gelling ability of hair colorings, decolorizing ability of decolorizing agents, a tight-knit wave, firmly rooted and no uneven wave formation, quick wave formation, less harsh smell (of ammonia) when and after permanent are applied, low irritation to the skin, good appearance of treating agent (for example, high-class pearly appearance, setting ability of finishing agents, and dispersibility and dissolving ability to aromatic materials and azulenes.

For the purpose to dissolve above-mentioned problems, the inventors of the present invention have conduced an ardent study and have found out that the use of compositions for blending in hair treating agents, in which alcohols were contained, could prepare hair treating agents having the above-mentioned excellent hair treating effect easily and by lower cost, and accomplished the present invention.

That is, the present invention provides compositions for blending in hair treating agents, which contain alcohols.

Further, the present invention provides the hair treating agents in which the above-mentioned compositions are blended.

Now, the present inventions will be described according to the following embodiment and Examples.

DETAILED DESCRIPTION OF PREFERRED EMBODIMENTS

The First Embodiment

In this embodiment, alcohols are contained in the compositions for blending in hair treating agents of the present invention.

As alcohols, for example, lower and higher alcohols, aromatic alcohols, polyhydric alcohols (e.g. glycols, glycerols, mannitol etc.) and partial etherified products of them or propylene oxide (PO) adducts of them etc. may be exemplified.

Concretely, one to four compounds selected from the group consisting of ethanol, isopropanol, hexyldecanol, cetanol, oleyl alcohol, benzyl alcohol, phenoxyisopropanol, propylene glycol, 1,3-butylene glycol, dipropylene glycol, diethylene glycol monoethyl ether, polyoxypropylene (5–15 PO) diglyceryl ether and D-mannitol may be exemplified.

For example, in compositions for blending in hair conditioners, in compositions for blending in waving agents, in compositions for blending in finishing agents and in compositions for blending in additives that increase the feeling effects, ethanol may be contained. In a composition for blending in a finishing agent and in a composition for blending in a refresher, 1,3-butylene glycol may be contained.

Further, in the compositions for blending in hair treating agents of the present invention, any kind of additives may be contained in accordance with the kind and the purposes of hair treating agents. For example, in the composition for blending in hair treating agent of the present invention, one to five ingredients selected from the group consisting of nonionic surfactants, polymers, silicones (i.e. Si containing compounds), organic acids, amines, cyclic amides, parabens, sequestering agents, hydrolyzed animal protein, UV absorbents and water may be contained as additives.

For example, in compositions for blending in hair colorings, in compositions for blending in finishing agents, in compositions for blending in additives that increase the feeling effects, and in compositions for blending in thickening agents used on preparing hair treating agents, nonionic surfactants may be contained.

In compositions for blending in hair conditioners, in compositions for blending in waving agents, in compositions for blending in finishing agents and in compositions for blending in additives that increase the feeling effects, for example, at least one ingredients selected from the group consisting of polymers, organic acids and parabens may be contained.

In compositions for blending in finishing agents, for example, amines may be contained.

In compositions for blending in refreshers, for example, cyclic amides may be contained.

In compositions for blending in hair conditioners, in compositions for blending in waving agents, in compositions for blending in finishing agents, in compositions for blending in additives that increase the feeling effects and in compositions for blending in thickening agents used on preparing hair treating agents, for example, water may be contained.

As nonionic surfactants, for example, polyoxyethylene alkyl ethers, polyoxyethylene alkenyl ethers, polyoxyethylene alkyl aryl ethers, polyoxyethylene derivatives prepared from natural fatty acids, ethylene oxide.propylene oxide block copolymers and fatty acid alkylolamides may be exemplified.

Ethylene oxide (EO) addition polymerization degree of "polyoxyethylene" may be, for example, 4–70 moles. Propylene oxide (PO) addition polymerization degree of "polyoxypropylene" may be, for example, 5–20 moles.

As nonionic surfactants, for examople, one or two ingredients selected from the groups consisting of polyoxyethylene lauryl ether, polyoxyethylene isostearyl ether, polyoxyethylene oleyl ether, polyoxyethylene behenyl ether, polyoxyethylene nonylphenyl ether, polyoxyethylene lanolin, polyoxyethylene.polyoxypropylene glycol, and coconut fatty acid diethanolamid may be exemplified.

As polymers, one to three compounds selected from the groups consisting of hydroxyethyl cellulose (the degree of viscosity of 2% aqueous solution, e.g. 1000–1500 cps.), polyethylene glycol (average molecular weight, e.g. 300–2000), propylene glycol alginate (the degree of viscosity of 1% aqueous solution, e.g. 10–100 cps.), carboxyvinylpolymer (average molecular weight, e.g. 1–5 million), polyacrylic acid (the degree of viscosity of 20% aqueous solution, e.g. 1000–10,000 cps.), polyvinylpyrrolidone (average molecular weight, e.g. 10000–100000), vinyl methyl ether.ethyl maleate copolymer, vinyl methyl ether-.butyl maleate copolymer, vinyl acetate.crotonic acid copolymer, carrageenan (the degree of viscosity of 1% aqueous solution, e.g. 100–1,000 cps.), polyvinylpyrrolidone N, N-dimethyl aminoethyl methacrylic acid copolymer diethyl sulfate (average molecular weight, e.g. 100000–1 million), octylamide acrylate.hydroxypropyl acrylate-butylaminoethyl methacrylate copolymer, dimethyl diallyl ammonium chloride.acrylamidecopolymer (average molecular weight, e.g. 100,000–1 million) and N-methacryloyl oxyethyl N, N-dimethyl ammonium-α-N-methyl carboxy betaine.alkyl methacrylate copolymer (the degree of viscosity of 30% ethanol solution, e.g. 100–1,000 cps.) may be concretely exemplified.

As silicones, at least one to three compounds selected from the groups consisting of decamethyl cyclopentasiloxane, methyl polysiloxane [e.g. low polymerized one (1–20 cs etc.), moderately polymerized one (1,000–5,000 cs etc.) or highly polymerized one (more than 10 million cs.),], methylphenyl polysiloxane (e.g. 1–100 cs.) and polyoxyethylene methyl polysiloxane copolymer (softening temperature, e.g. 30–60° C.) may be exemplified.

As organic acids, fatty acids, polyacids and amino acids may be exemplified. Concretely, at least one compound selected from the groups consisting of stearic acid, tartaric acid and trimethylglycine may be exemplified. Triethanolamine and/or AMP (2-amino-2-methyl-1-propanol) may be exemplified as amins.

As cyclic amides, N-methyl-2-pyrrolidone may be exemplified. As parabens, methyl parahydroxybenzoate, and/or propyl parahydroxybenzoate may be exemplified. As sequestering agents, disodium edetate may be exemplified. As UV absorbents, oxybenzone may be exemplified.

In the formulations of the compositions for blending in hair treating agents of the present invention, when the content of alcohols is A (wt %), it is desirable for A to be within following ranges; $0.5 \leqq A \leqq 90$.

For example, in a case of the compositions for blending in hair conditioners and in a case of compositions for blending in additives that increase the feeling effects, A may be $1 \leqq A \leqq 10$.

In a case of compositions for blending in hair colorings, A may be, for example, $10 \leqq A \leqq 65$.

In a case of compositions for blending in waving agents, A may be, for example, $1 \leqq A \leqq 85$.

In a case of compositions for blending in finishing agents, A may be, for example, $0.5 \leqq A \leqq 70$.

In a case of the compositions for blending in aromatic material dispersants, A may be, for example, $15 \leqq A \leqq 45$.

In a case of compositions for blending in refreshers, A may be, for example, $10 \leqq A \leqq 80$.

In a case of compositions for blending in thickening agents used on preparing hair treating agents, A may be, for example, $10 \leqq A \leqq 40$.

As the substantial method to prepare the compositions for blending in hair treating agents of this embodiment, following method may be exemplified. That is, alcohols and ingredients such as additives (If necessary) are mixed and stirred under heating (If necessary) until completely dissolved. The heating temperature is desirably lower than the decomposition temperature of the mixture, for example, lower than 100° C., more desirably lower than 85° C. The adding order of each ingredient is not limited.

In another preparation method of the compositions for blending in hair treating agents of this embodiment, for example, alcohols and other oiliness ingredients are stirred and mixed homogeneously under heating if necessary. Next, water is added to this homogeneous mixture (or this homogeneous mixture is added to water), and then mixed homogeneously as stirring to prepare the compositions for blending in hair treating agents of this embodiment.

The hair treating agents of the present invention contain the above-mentioned compositions for blending in hair treating agents of the present invention.

Hair conditioners, hair colorings, waving agents, finishing agents, additives that increase the feeling effects, aromatic material dispersants, refreshers and thickening agents used on preparing hair treating agents are illustrated below as the hair treating agents.

The hair conditioners of the present invention contain above-mentioned compositions for blending in hair conditioners. One or more kinds of the compositions for blending in hair conditioners may be used.

Further, in the hair conditioners of the present invention, alcohols, esters, cationic surfactants and water may be contained as additives.

Higher alcohols (e.g. cetanol) may be exemplified as alcohols.

As esters, fatty esters (glyceryl monostearate etc.) may be exemplified. As cationic surfactants, higher alkyl trimethyl ammonium salts (concretely, cetyl trimethyl ammonium chloride etc.) may be exemplified.

In the formulations of the hair conditioners of the present invention, the contents of the compositions for blending in hair conditioners are, for example, from 1 to 20 wt. %.

The preparing methods of the hair conditioners of the present invention are not limited. For example, alcohols, esters, cationic surfactants and water are mixed homogeneously under heating. After the mixtures are cooled, the composition for blending in the hair conditioner is added to the mixtures to prepare the hair conditioner of the present invention. In another preparing method of the hair conditioner of the present invention, for example, alcohols, esters, cationic surfactants, the composition for blending in the hair conditioner and water are mixed homogeneously under heating to prepare the hair conditioner of the present invention.

As hair colorings of the present invention, oxidizing hair coloring agents may be exemplified. The oxidizing hair coloring agents are composed of No. 1 agents and No. 2 agents. No. 1 agents of the oxidizing hair coloring agents of the present invention may contain dye intermediates, alcohols, antioxidants, sequestering agents, alkaline agents and water may be contained besides the compositions for blending in hair colorings of the present invention (In the present invention, No. 1 agents alone are also comprised in the hair colorings of the present invention.).

As dye intermediates, for example, phenylene diamines (e.g. ortho-, meta-, para-phenylene diamine), phenols (e.g. ortho-, meta-, para-aminophenol, nitrophenols), resorcinol and aminocresols may be exemplified. As alcohols, for example, lower alcohols (ethanol, isopropanol etc.) and glycols (Propylene glycol etc.) may be exemplified.

As antioxidants, such compounds that are ordinarily used to the oxidizing hair coloring agents, for example, sodium sulfite, ammonium thioglycolate (ATG), ascorbic acid and cysteine may be exemplified. As the sequestering agents, for example, disodium edetate (EDTA.2 Na.) may be exemplified. As alkaline agents, ammonia aqueous solution and monoethanolamine (MEA) may be exemplified.

In the formulations of No. 1 agents of oxidizing hair coloring agents, the contents of the compositions for blending in hair colorings are, for example, from 40 to 80 wt. %.

As the substantial methods to prepare No. 1 agents of oxidizing hair coloring agents, following methods may be exemplified. That is, for example, alcohols is poured into heated water to prepare aqueous solution, and then dye intermediates is added and dissolved homogeneously. Next, the composition for blending in the hair coloring is added and mixed homogeneously. After cooling, additives such as alkaline agents, antioxidants and sequestering agents may be added to the mixture by constant stirring to prepare No. 1 agent of oxidizing hair coloring agent. The heating temperature of water and the composition for blending in hair coloring are desirably lower than decomposition temperatures of the ingredients, for example, lower than 95° C.

As No. 2 agents of oxidizing hair coloring agents, such No. 2 agents that are generally used as the usual No. 2 agents of oxidizing hair coloring agents may be exemplified. Concretely, hydrogen peroxide may be exemplified.

As another hair treating agent, decolorizing agents may be exemplified. The decolorizing agents are generally composed of No. 1 agents and No. 2 agents.

No. 1 agents of the decolorizing agents of the present invention may contain alcohols, antioxidants, sequestering agents, alkaline agents and water may be contained besides the compositions for blending in hair colorings of the present invention (In the present invention, the decolorizing agents and No. 1 agents of the decolorizing agents alone are also comprised in the hair colorings of the present invention). As alcohols, antioxidants, sequestering agents and alkaline agents, the same ones that are illustrated respectively in the above-mentioned No. 1 agents of oxidizing hair coloring agents may be exemplified concretely.

In formulations of No. 1 agents of decolorizing agents, the desirable contents of the compositions for blending in hair colorings are, for example, from 40 to 80 wt. %.

As the substantial methods to prepare No. 1 agents of decolorizing agents, following method may be exemplified. That is, for example, alcohols is poured into heated water to prepare aqueous solution, and then the composition for blending in hair coloring is added and mixed homogeneously. After cooled down as stirring, additives such as alkaline agents, antioxidants and sequestering agents may be added to the mixture. The heating temperature of water and the composition for blending in hair coloring is desirably lower than decomposition temperatures of the ingredients, for example, lower than 95° C.

The above-mentioned No. 2 agents of the oxidizing hair coloring agents may be used as No. 2 agents of the decolorizing agents.

Waving agents of the present invention may be composed of No. 1 agents and No. 2 agents. No. 1 agents of the waving agents of the present invention may contain reducing agents, alkaline agents and water besides the compositions for blending in waving agents of the present invention (In the present invention, No. 1 agents alone are also comprised in the hair treating agents of the present invention).

One or more kinds of the compositions for blending in waving agents may be used. As reducing agents, thioglycolic acid, cysteine or salts [ammonium salt, monoethanolamine (MEA) salt, hydrochloric acid salts etc.) of them may be exemplified. As alkaline agents, ammonia, amines (MEA, isopropanolamine, etc.), ammonium salts (ammonium bicarbonate etc.) and basic amino acid may be exemplified.

In formulations of No. 1 agents of the waving agents of the present invention, the contents of the compositions for blending in waving agents are, for example, from 0.1 to 20 wt. %.

As the substantial methods to prepare No. 1 agents of the waving agents, following method may be exemplified. That is, for example, the composition for blending in waving agent, reducing agents, alkaline agents and water are mixed as stirring under heating, if necessary, to prepare the No. 1 agent of the waving agent of the present invention.

As No. 2 agents of the waving agents, such No. 2 agents as are ordinaly used in the waving agents may be exemplified. As such No. 2 agents of waving agents, the mixture prepared by dissolving oxidizing agents (e.g. sodium bromide) and surfactants (lauryl trimethyl ammonium chloride, lauryl trimethyl ammonium bromide etc.) homogeneously in water may be exemplified.

The finishing agents of the present invention contain the compositions for blending in finishing agents, and generally further contain water. One or more kinds of the compositions for blending in finishing agents may be used. Further, additive compositions, silicones, parabens, alcohols, nonionic surfactants, UV absorbents, perfumes, colorants, alkaline agent, fats and oils, hydrocarbons, cyclic amides, amines, gum substances and polymers may be contained as additives.

As additive compositions, aqueous compositions that contain amphoteric surfactants, nonionic surfactants and phosphoric acid, and silicone compositions may be exemplified. As parabens, methyl parahydroxybenzoate and propyl parahydroxybenzoate may be exemplified. As alcohols, ethanol may be exemplified. As nonionic surfactants, polyoxyethylene nonylphenyl ether, polyoxyethylene stearyl ether and polyethylene glycol monostearate may be exemplified. As UV absorbents, oxybenzone may be exemplified.

As perfumes, any kinds of perfumes, which are generally used to the finishing agents, may be exemplified. As colorants, tar dye may be exemplified. As alkaline agents, sodium hydroxide and potassium hydroxide may be exemplified. As fats and oils, jojoba oil may be exemplified. As hydrocarbons, squalane may be exemplified. As cyclic amides, N-methl-2-pyrrolidone may be exemplified. As amines, AMP may be exemplified. As gum substances, xanthan gum may be exemplified. As polymers, carrageenan may be exemplified.

In formulations of the finishing agents of the present invention, the contents of the compositions for blending in finishing agents are, for example, from 1 to 35 wt. %.

As the substantial methods to prepare the finishing agents of the present invention, following method may be exemplified. That is, for example, each ingredient is mixed homogeneously as stirring to prepare the finishing agents. All ingredients may be added at a time. Or, all ingredients may be added in such order as each ingredient can be dissolved homogeneously. Concretely, additive compositions, water, polymers, cyclic amides, the composition for blending in finishing agents, parabens and perfumes are added in order as stirring and mixed homogeneously to prepare the finishing agents.

In another preparation method of finishing agents of the present invention, for example gum substances, parabens and water are mixed and heated to prepare aqueous solutions. On the other hand, the composition for blending in finishing agent is dissolved homogeneously under heating. Next, the above-mentioned heated aqueous solution are added to the homogeneous dissolved composition for blending in finishing agent with constant stirring to prepare emulsions. Then, the emulsion is cooled to prepare the finishing agents.

Additives that increase the feeling effects of the present invention are such one as may be blended to hair treating agents such as hair conditioners and permanent waving agents, and as can increase the feels, especially, moist feel and rustle feeling at the time of finishing, and further as can prevent hair damage. The compositions for blending in additives that increase the feeling effects of the present invention may be used solely as additives that increase the feeling effects. Or, additives that increase the feeling effects may further contain fats and oils (e.g. animal and vegetable fats and oils etc.) and surfactants (e.g. cationic surfactants).

The contents of additives that increase the feeling effects of the present invention are 2–7 wt. % of total weights of hair treating agents containing the additives that increase the feeling effects, when the additives that increase the feeling effects are blended to hair treating agents such as hair conditioners and permanent waving agents.

Aromatic material dispersants of the present invention may be blended to hair treating agents such as permanent waving agents. Aromatic material dispersants are such ones as disperse or soluve aromatic materials and azulenes.

Aromatic material dispersants of the present invention contain the compositions for blending in aromatic material dispersants and aromatic materials, and generally further contain water. Aromatic materials are not limited, and any kinds of aromatic materials, which are generally blended to the hair treating agents such as permanent waving agents, may be used.

In the formulations of the aromatic material dispersants of the present invention, for example, 1–5 part by weight of the compositions for blending in aromatic material dispersants may be blended per 1 part by weight of aromatic materials.

As the substantial methods to prepare aromatic material dispersants, following method may be exemplified. That is, for example, the composition for blending in aromatic material dispersant and aromatic materials are mixed homogeneously. Next, water is added to the mixture as stirring under heating, if necessary, and then the obtained mixture is dispersed or soluved to prepare aromatic material dispersants.

In the formulations of the aromatic material dispersants of the present invention, the contents of the aromatic materials are, for example, from 0.01 to 1 wt. %, when the aromatic material dispersants are blended to hair treating agents such as waving agents.

Refreshers of the present invention are such ones as can remove hair coloring materials applied on hair and as can restore the hair. Refreshers of the present invention contain the compositions for blending in refreshers. Refreshers may further contain additive compositions, nonionic surfactants, reducing agents and water etc.

As additive compositions, mixtures of natural fatty acids (hard lanolin fatty acid etc.), alcohols (cetanol etc.), esters (Isopropyl myristate etc.), hydrocarbons (Paraffines etc.), nonionic surfactants and cationic surfactants (cetyl trimethyl ammonium chloride etc) may be exemplified. As nonionic surfactants, polyoxyethylene oleyl ether and polyoxyethylene cetyl ether may be exemplified. As a reducing agent, sodium sulfite may be exemplified.

In formulations of the refreshers of the present invention, the contents of the compositions for blending in refreshers are, for example, from 1 to 25 wt. %.

As the substantial methods to prepare the refreshers of the present invention, following method may be exemplified. That is, for example, the composition for blending in refresher, additive compositions, nonionic surfactants and parabens are mixed as stirring under heating. Next, to this mixture, reducing agents, alkaline agents and water are added and emulsified to prepare the refreshers.

Thickening agents used on preparing hair treating agents of the present invention are such ones as may be blended to hair treating agents such as waving agents when hair treating agents are prepared and as can increase the viscosity of hair treating agents. The compositions for blending in thickening agents used on preparing hair treating agents of the present invention may be used solely as thickening agents used on preparing hair treating agents. Or, thickening agents used on preparing hair treating agents may further contain esters, glycols, preservatives and water.

As esters, fatty esters such as cetyl octanoate may be exemplified. As glycols, 1,3-butylene glycol may be exemplified. As preservatives, parabens such as methyl parahydroxybenzoate may be exemplified.

The contents of thickening agents used on preparing hair treating agents of the present invention are 1–25 wt. % of total weights of hair treating agents containing the thickening agents used on preparing hair treating agents, when the thickening agents used on preparing hair treating agents are blended to hair treating agents such as waving agents.

The Second Embodiment

In this embodiment, at least one selected from the groups consisting of anionic surfactants, inorganic acids and inorganic alkaline agents besides alcohols are contained in the compositions for blending in hair treating agents of the present invention.

As alcohols, for example, lower and higher alcohols, natural alcohols, aromatic alcohols, polyhydric alcohols (e.g. glycols glycerols etc.) may be exemplified.

Concretely, one to four compounds selected from the group consisting of ethanol, isopropanol, lauryl alcohol, cetanol, stearyl alcohol, oleyl alcohol, behenyl alcohol, cetostearyl alcohol, benzyl alcohol, propylene glycol, 1,3-butylene glycol and glycerin (concentrated glycerin) may be exemplified.

For example, in compositions for blending in waving agents and in compositions for blending in hair colorings, lauryl alcohol and/or cetanol may be contained. In compositions for blending in hair conditioners, in compositions for blending in hair colorings, in compositions for blending in waving agents and in compositions for blending in finishing agents, glycerin may be contained.

Further, in the compositions for blending in hair treating agents of the present invention, anionic surfactants, inorganic acids or inorganic alkaline agents are contained.

For example, in compositions for blending in hair colorings, in compositions for blending in waving agents, in compositions for blending in finishing agents and in compositions for blending in depilatories, anionic surfactants may be contained. In compositions for blending in hair colorings, in compositions for blending in waving agents, in compositions for blending in finishing agents and in compositions for blending in additive that increases the feeling effects, for example, inorganic acids may be contained. In compositions for blending in hair conditioners and in compositions for blending in hair colorings, for example, inorganic alkaline agents may be contained.

As anionic surfactants, for example, higher alkyl sulfuric acid salts, sulfonic acid salts of higher fatty acid amides, esters of higher alkyl ether sulfuric acid or esters of higher alkyl ether phosphoric acid may be exemplified.

Concretely, one or two compounds selected from the groups consisting of sodium lauryl sulfate, triethanolamine lauryl sulfate, sodium cetyl sulfate, sodium N-myristoyl methyl taurate, triethanolamine polyoxyethylene lauryl ether sulfate and polyoxyethylene oleylether phosphate may be exemplified. Ethylene oxide (EO) polymerization degrees of "polyoxyethylene" may be, for example, 2–5.

As inorganic acids, for example, phosphoric acid and the salts of it may be exemplified. Concretely, phosphoric acid or dibasic sodium phosphate may be exemplified.

As inorganic alkaline agents, for example, hydroxides of alkali metals (concretely, sodium hydroxide) may be exemplified.

Further, in the compositions for blending in hair treating agents of the present invention, any kind of additives may be contained in accordance with the kind and the purposes of hair treating agents. For example, in the compositions for blending in hair treating agents of the present invention, one to six ingredients selected from the group consisting of nonionic surfactants, fats and oils, hydrocarbon, polymers, organic acids, organic bases, amphoteric surfactants, sequestering agents, hydrolyzed animal protein, perfume, parabens, such solvents that are containing nitrogen element and water may be contained.

For example, in compositions for blending in hair colorings, in compositions for blending in waving agents, in compositions for blending in finishing agents, in compositions for blending in additive that increases the feeling effects and in compositions for blending in depilatories, nonionic surfactants may be contained. In compositions for blending in waving agents, for example, one or two selected from the group consisting of fats and oils, organic acids, amphoteric surfactants and perfume may be contained.

In compositions for blending in depilatories, for example, hydrocarbons may be contained. In compositions for blending in hair conditioners, in compositions for blending in hair colorings, in compositions for blending in waving agents, in compositions for blending in finishing agents and in compositions for blending in additive that increases the feeling effects, for example, polymers may be contained. In compositions for blending in hair conditioners, in compositions for blending in hair colorings and in compositions for blending in waving agents, for example, organic acids may be contained. In compositions for blending in waving agents and in compositions for blending in additive that increases the feeling effects, for example, sequestering agents may be contained.

In compositions for blending in hair conditioners, for example, hydrolyzed animal protein, may be contained. In compositions for blending in hair conditioners, in compositions for blending in waving agents, in compositions for blending in finishing agents and in compositions for blending in additive that increases the feeling effects, for example, parabens may be contained. In compositions for blending in hair colorings, for example, such solvents that are containing nitrogen element, may be contained. In compositions for blending in hair conditioners, in compositions for blending in hair colorings, in compositions for blending in waving agents, in compositions for blending in finishing agents, in compositions for blending in additive that increases the feeling effects and in compositions for blending in depilatories, for example, water may be contained.

As nonionic surfactants, for example, polyoxyethylene alkyl ethers, polyoxyethylene alkenyl ethers, polyoxyethylene alkylaryl ethers, polyoxyethylene derivatives prepared from natural fatty acids, ethylene oxide.propylene oxide block copolymers, fatty acid alkylolamides and esters (e.g. tetraesters) prepared from polyhydric alcohols (e.g. sorbitane etc.) and higher fatty acids may be exemplified.

Ethylene oxide (EO) addition polymerization degrees of "polyoxyethylene" may be, for example, 2–70 moles. Propylene oxide (PO) addition polymerization degrees of "polyoxypropylene" may be, for example, 4–25 moles.

As nonionic surfactants, one, two, three, four or six compounds selected from the groups consisting of polyoxyethylene lauryl ether, polyoxyethylene cetyl ether, polyoxyethylene stearyl ether, polyoxyethylene oleyl ether, polyoxyethylene nonylphenyl ether, polyoxyethylene castor oil, polyoxyethylene hydrogenated castor oil, polyoxyethylene lanolin, polyoxyethylene cocoalkyl amine, polyoxyethylene.polyoxypropylene cetyl ether, polyoxyethylene.polyoxpropylene lanolin, oleic acid diethanolamide, stearic acid diethanolamide, polyoxyethylene sorbitol tetraoleate and cocodimethyl amine oxide may be exemplified concretely.

As fats and oils, animal and vegetable fats and oils may be exemplified. As fats and oils, one or two compounds selected from the groups consisting of meadowfoam oil, olive oil, shea butter and mink wax may be exemplified concretely. As hydrocarbons, liquid petrolatum may be exemplified.

As polymers, dimethyl diallyl ammonium chloride-acrylamide copolymer (average molecular weight, e.g. 100,000–1 million), hydroxyethyl cellulose (the degree of viscosity, e.g. 500–5,000 cps.), polypropylene (10–50 PO) glycol, carboxyvinylpolymer (average molecular weight, e.g. 2–5 million) or polyoxypropylene (10–50 PO) methylglucoside ether may be exemplified concretely.

As organic acid, glycolic acid or tartaric acid may be exemplified concretely. As organic bases, triethanolamine may be exemplified concretely. As amphoteric surfactants, 2-alkyl N-carboxymethyl N-hydroxyethyl imidazolinium betaine or cocamidopropyl betaine may be exemplified concretely. As sequestering agents, 1-hydroxyethane-1,1-diphosphonic acid or disodium edetate may be exemplified concretely.

As perfumes, orange oil may be exemplified concretely. As parabens, one or two compounds selected from the groups consisting of propyl parahydroxybenzoate, isopropyl parahydroxybenzoate and methyl parahydroxybenzoate may be exemplified concretely. As nitrogen containing solvent is, N-methyl-2-pyrrolidone may be exemplified concretely.

In the formulations of the compositions for blending in hair treating agents of the present invention, when the respective contents of alcohols and one kind ingredient selected from the groups consisting of anionic surfactants, inorganic acids and inorganic alkaline agents are B and C (wt %), B and C desirably satisfy the ranges of $0.1 \leqq B \leqq 90$, $0.05 \leqq C \leqq 65$ and $B+C \leqq 100$.

For example, in a case of the compositions for blending in hair conditioners, B and C may be $1 \leqq B \leqq 30$, $0.1 \leqq C \leqq 10$.

In a case of compositions for blending in hair colorings, B and C may be, for example, $10 \leqq B \leqq 65$, $0.1 \leqq C \leqq 10$.

In a case of compositions for blending in waving agents, B and C may be, for example, $0.1 \leqq B \leqq 90$, $0.05 \leqq C \leqq 65$ and $B+C \leqq 100$.

In a case of compositions for blending in finishing agents, B and C may be, for example, $15 \leqq B \leqq 50$, $0.05 \leqq C \leqq 20$.

In a case of compositions for blending in additives that increase the feeling effects, B and C may be, for example, $1 \leqq B \leqq 10$, $0.1 \leqq C \leqq 10$.

In a case of compositions for blending in depilatories, B and C may be, for example, $20 \leqq B \leqq 60$, $1 \leqq C \leqq 10$.

As the substantial methods to prepare the compositions for blending in hair treating agents of this embodiment, following method may be exemplified. That is, for example, alcohols, at least one selected from the group consisting of anionic surfactants, inorganic acids and inorganic alkaline agents and, if necessary, various ingredients such as additives are mixed and stirred under reduced pressure and/or heating, if necessary, until the mixtures are completely dissoluved. The reduced pressure may be, for example, 400–600 mm Hg. The heating temperatures is desirably lower than the decomposition temperature of the mixture, for example, lower than 95° C. The adding order of each ingredient is not limited. For example, all ingredients may be added at a time. Or, after it is confirmed that the previously added ingredients are mixed homogeneously, following ingredients are added.

In another preparation methods of the compositions for blending in hair treating agents, for example, alcohols and another various oiliness ingredients (e.g. nonionic surfactants, parabens etc.) are mixed, heated and homogeneously dissolved. This homogeneously dissolved mixture is added to heated water with constant stirring and emulsified, and then cooled.

Then, at least one kind selected from the groups consisting of anionic surfactants, inorganic acids and inorganic alkaline agents are added with constant stirring to the above-mentioned cooled emulsion and mixed homogeneously to prepare the composition for blending in hair treating agent. The heating temperature is desirably lower than the decomposition temperatures of the mixture, for example, lower than 95° C.

The hair treating agents of the present invention contain the above-mentioned compositions for blending in hair treating agents of the present invention. Hair conditioners, hair colorings, waving agents, finishing agents, additives that increase the feeling effects or depilatories are illustrated below as the hair treating agents.

Hair conditioners of the present invention include 2-bath (or 2-agents) type of treatments. 2-bath type of treatment consists of Liquid 1 and Liquid 2.

Liquid 1 of 2-bath type of treatment of the present invention contains compositions for blending in hair conditioners of the present invention. Further, in the Liquid 1 of the present invention, alcohols, preservatives and water etc. may be contained as additives. (In the present invention, Liquid 1 of 2-bath type of treatment of the present invention alone is also included in the hair conditioners of the present invention). As alcohos, ethanol and 1,3-butylene glycol may be exemplified. As preservative, parabens may be exemplified.

As the substantial methods to prepare Liquid 1 of 2-bath type of treatment of the present invention, following method may be exemplified. That is, for example, composition for blending in hair conditioner and water are mixed homogeneously to prepare aqueous composition. On the other hand, alcohols and preservatives are mixed homogeneously to prepare oiliness composition. Next, the oiliness composition is added to the aqueous composition as stirring to prepare the Liquid 1.

In the Liquid 2 of 2-bath type of treatment of the present invention, alcohols, cationic surfactants, nonionic surfactants, preservatives, organic acids, silicones (Si compounds) and water etc. may be contained.

Higher alcohols (behenyl alcohol etc.) and glycols (1,3-butylene glycol etc.) may be exemplified as alcohols. As cationic surfactants, stearyl trimethyl ammonium chloride etc. may be exemplified. As nonionic surfactants, polyoxyethylene (e.g. 10–30 EO) sorbitan monooleate may be exemplified.

As preservatives, parabens (e.g. methyl parahydroxybenzoate, propyl parahydroxybenzoate) may be exemplified. As organic acids, lactic acid may be exemplified. As silicones, amino-modified silicones, and methyl polysiloxane (e.g. 10–30 cs.) may be exemplified.

In the formulations of the Liquid 2 of 2-bath type of treatment, the content of alcohols may be 5–30 wt. %. The content of cationic surfactants may be 1–5 wt. %. The content of nonionic surfactants may be 0.1–1 wt. %. The content of preservatives may be 0.05–1 wt. %. The content of organic acids may be 0.01–1 wt. %. The content of silicones may be 10–30 wt. %.

The preparing methods of the Liquid 2 of 2-bath type of treatment are not limited. For example, alcohols, cationic surfactants, nonionic surfactants and preservatives are mixed, heated and dissolve homogeneously. To this mixture, organic acids aqueous solution, that have been previously heated, is added and emulsified. After the emulsion is cooled, silicones is added to the cooled emulsion and then mixed homogeneously to prepare the Liquid 2 of 2-bath type of treatment.

As hair colorings of the present invention, acidic hair coloring materials may be exemplified. The acidic hair coloring materials may contain alcohols, dyes, acids and water besides the present compositions for blending in hair colorings. As alcohols, ethanol, benzyl alcohol and glycerin may be exemplified. As dyes, tar colorants (e.g. Red No. 2, Orange No. 205, Yellow No. 4, Green No. 3 and No. 204, Violet No. 401, Black No. 401) may be exemplified. As acid, organic acids (e.g. lactic acid, glycolic acid, tartaric acid, citric acid.) may be exemplified. As inorganic acids, hydrochloric acid may be exemplified.

In formulations of the acidic hair coloring materials, the contents of the compositions for blending in hair colorings are, for example, from 20 to 90 wt. %.

As the substantial methods to prepare the acidic hair coloring materials, following method may be exemplified. That is, for example, alcohols, dyes and organic acids are added to the composition for blending in hair coloring in order, and then mixed homogeneously to prepare the acidic hair coloring materials.

As another hair colorings of the present invention, oxidizing hair coloring agents may be exemplified. The oxidizing hair coloring agents are composed of No. 1 agents and No. 2 agents (In the present invention, No. 1 agents alone and No. 2 agents alone are also comprised in the hair colorings of the present invention). No. 1 agents of the oxidizing hair coloring agents of the present invention may contain dye intermediates, alkaline agents, antioxidants, sequestering agents and water besides the compositions for blending in hair colorings of the present invention.

As dye intermediates, for example, phenylene diamines (e.g. ortho-, meta-, para-phenylene diamine), phenols (e.g. ortho-, meta-, para-aminophenol, nitrophenols.) and aminocresols may be exemplified. As alkaline agents, ammonia solution and MEA (Monoethanolamine) may be exemplified. As antioxidants, the compounds, that are used to the ordinary oxidizing hair coloring agents, such as sodium sulfite, ammonium thioglycolate, ascorbic acid and cysteine may be exemplified. As the sequestering agents, EDTA may be exemplified.

In the formulations of No. 1 agents of oxidizing hair coloring agents, the contents of the compositions for blending in hair colorings are, for example, from 10 to 35 wt.

As the substantial methods to prepare No. 1 agents of oxidizing hair coloring agents, following method may be exemplified. That is, for example, dye intermediates and antioxidants are poured into heated water to prepare aqueous solution, then the composition for blending in hair coloring, that has been heated and dissolved homogeneously, is added to the aqueous solution and mixed. After cooling, additives such as alkaline agents and sequestering agents may be added to the aqueous solution by constant stirring. The heating temperature of water and the composition for blending in hair coloring is desirably lower than decomposition temperatures of the ingredients, for example, lower than 95° C.

No. 2 agents of oxidizing hair coloring agents of the present invention may contain oxidizing agents, sequestering agents, pH adjustors and water may be contained besides the compositions for blending in hair colorings of the present invention. As oxidizing agents, hydrogen peroxide may be exemplified. As sequestering agents, e.g. 1-hydroxyethane-1,1-diphosphonic acid may be exemplified. As pH adjustors, phosphoric acid salts (for example, dibasic sodium phosphate) may be exemplified.

In formulations of No. 2 agents of oxidizing hair coloring agents, the compositions for blending in hair colorings may be contained, for example, from 1 to 15 wt. %.

As the substantial methods to prepare No. 2 agents of oxidizing hair coloring agents, following method may be exemplified. That is, for example, the composition for blending in hair coloring of the present invention, that has been heated and dissolved homogeneously, is added to heated water, and then stirred and emulsified. After cooled down, additives such as sequestering agents, pH adjustors and oxidizing agents may be added. The heating temperature of water and the composition for blending in hair coloring is desirably lower than the decomposition temperatures of the ingredients, for example, lower than 95° C.

The oxidizing hair coloring agents of the present invention contain at least one selected from the group consisting of No. 1 agents of oxidizing hair coloring agents of the present invention and No. 2 agents of oxidizing hair coloring agents of the present invention. For example, in the oxidizing hair coloring agents of the present invention, the hair colorings consisting of No. 1 agents of oxidizing hair coloring agents of the present invention and No. 2 agents of oxidizing hair coloring agents of the present invention, the hair colorings consisting of No. 1 agents of oxidizing hair coloring agents of the present invention and No. 2 agents of oxidizing hair coloring agents except the above-mentioned ones, and the hair colorings consisting of No. 1 agents of oxidizing hair coloring agents except the above-mentioned ones and No. 2 agents of oxidizing hair coloring agents of the present invention are included.

As "No. 1 agents of oxidizing hair coloring agents except the above-mentioned ones" and "No. 2 agents of oxidizing hair coloring agents except the above-mentioned ones", No. 1 agents and No. 2 agents which are generally used for the usual hair colorings may be exemplified.

As another hair treating agents of the present invention, decolorizing agents may be exemplified. The decolorizing agents are generally composed of No. 1 agents and No. 2 agents (the decolorizing agents, No. 1 agents alone and No. 2 agents alone are comprised in the hair colorings of the present invention).

No. 1 agents of the decolorizing agents of the present invention may contain antioxidants, alkaline agents, sequestering agents and water besides the compositions for blending in hair colorings of the present invention.

As antioxidants, the compounds, that are used to the ordinary oxidizing hair coloring agents, such as sodium sulfite, ammonium thioglycolate, ascorbic acid and cysteine may be exemplified. As alkaline agents, e.g. MEA and ammonia may be exemplified, and as sequestering agents, EDTA and hydroxyethane diphosphonic acid may be exemplified.

In formulations of No. 1 agents of decolorizing agents, the contents of the compositions for blending in hair colorings are, for example, from 10 to 35 wt. %.

As the substantial method to prepare No. 1 agents of decolorizing agents, following method may be exemplified. That is, for example, antioxidants and sequestering agents are added to heated water to prepare aqueous solution. Next, the composition for blending in hair coloring of the present invention, that has been heated and dissolved homogeneously, is added to the heated aqueous solution, and then mixed. After cooled down, additives such as alkaline agents may be added as stirring. The heating temperature of water and the composition for blending in hair coloring is desirably lower than the decomposition temperatures of the ingredients, for example, lower than 90° C.

No. 2 agents of decolorizing agents of the present invention may contain sequestering agents, pH adjustors, oxidizing agents and water may be contained besides the compositions for blending in hair colorings of the present invention. As sequestering agents, e.g. 1-hydroxyethane-1, 1-diphosphonic acid may be exemplified. As pH adjustors, phosphoric acid salts (for example, dibasic sodium phosphate) may be exemplified. As oxidizing agents, hydrogen peroxide may be exemplified.

In formulations of No. 2 agents of decolorizing agents, the compositions for blending in hair colorings may be contained, for example, from 1 to 15 wt. %.

As the substantial method to prepare No. 2 agents of decolorizing agents, following method may be exemplified. That is, for example, the composition for blending in hair coloring of the present invention, that has been heated and dissolved homogeneously, is added to heated water, and then stirred and emulsified. After cooled down as stirring, additives such as sequestering agents, pH adjustors and oxidizing agents may be added. The heating temperature of water and the compositions for blending in hair colorings is desirably lower than the decomposition temperatures of the ingredients, for example, lower than 90° C.

The decolorizing agents of the present invention contain at least one selected from the group consisting of No. 1 agents of decolorizing agents of the present invention and No. 2 agents of decolorizing agents of the present invention. For example, in the decolorizing agents of the present invention, the decolorizing agents consisting of No. 1 agents of decolorizing agents of the present invention and No. 2 agents of decolorizing agents of the present invention, the decolorizing agents consisting of No. 1 agents of decolorizing agents of the present invention and No. 2 agents of decolorizing agents except the above-mentioned ones, and the decolorizing agents consisting of No. 1 agents of decolorizing agents except the above-mentioned ones and No. 2 agents of decolorizing agents of the present invention are included.

As "No. 1 agents of decolorizing agents except the above-mentioned ones" and "No. 2 agents of decolorizing agents except the above-mentioned ones", No. 1 agents and No. 2 agents which are generally used for the usual decolorizing agents may be exemplified.

Waving agents of the present invention may be composed of No. 1 agents and No. 2 agents (In the present invention, both No. 1 agents alone and No. 2 agents alone are also comprised in the waving agents of the present invention). No. 1 agents of the waving agents of the present invention may contain reducing agents, alkaline agents, antibacterial agents and water besides the compositions for blending in waving agents of the present invention.

One or more kinds of the compositions for blending in waving agents may be used. As reducing agents, thioglycolic acid, cysteine or salts [ammonium salt, monoethanolamine (MEA) salt, hydrochloric acd salts etc.] of them may be exemplified. As alkaline agents, ammonia, amines (MEA, isopropanolamine, etc.), ammonium salts (ammonium bicarbonate etc.) and basic amino acid may be exemplified. As antibacterial agents, sodium dehydroacetate may be exemplified.

In formulations of No. 1 agents of the waving agents of the present invention, the contents of the compositions for blending in waving agents may be, for example, from 0.1 to 35 wt. %.

As the substantial method to prepare No. 1 agents of the present waving agents, following method may be exemplified. That is, for example, the composition for blending in waving agent, that has been heated and dissolved homogeneously, is added to heated water, stirred and emulsified. Then, viscous liquid is prepared by cooling. Next, reducing agents and alkaline agents may be added to the viscous liquid as stirring at room temperature, and mixed homogeneously as stirring. The contents of the compositions for blending in waving agents in viscous liquids may be, for example, from 1 to 20 wt. %.

As another method to prepare No. 1 agent of the present waving agent, following method may be exemplified. That is, for example, the composition for blending in waving agent, reducing agent, alkaline agent and water are added, and then mixed as stirring under heating, if necessary, to prepare No. 1 agent of the present waving agent.

In No. 2 agents of the waving agents of the present invention, oxidizing agents, surfactant and water etc. may be contained besides the compositions for blending in waving agents of the present invention. One or more kinds of the compositions for blending in waving agents may be used. As oxidizing agents, salts of bromic acid (e.g. sodium bromide) or hydrogen peroxide may be exemplified. As surfactants, lauryl trimethyl ammonium halide (lauryl trimethyl ammonium chloride, lauryl trimethyl ammonium bromide etc.) may be exemplified.

In formulations of No. 2 agents of the waving agents, the contents of the compositions for blending in waving agents are, for example, from 1 to 50 wt. %.

Instead of the above-mentioned No. 2 agents of the waving agents of the present invention, No. 2 agents of the waving agents, that are ordinaly used in waving agents, may be used. As such No. 2 agents of the waving agents, the mixture prepared by dissolving oxidizing agents (e.g. sodium bromide) and surfactants (lauryl trimethyl ammonium chloride, lauryl trimethyl ammonium bromide etc.) homogeneously in water may be exemplified.

As the method to prepare No. 2 agents of the waving agents, following method may be exemplified. That is, for example, water and oxidizing agents are mixed and heated to prepare aqueous solution, then the composition for blending in waving agent, that has been heated and dissolved homogeneously, is added to the aqueous solution and emulsified by stirring. After cooled down, No. 2 agent of the waving agent of the present invention are obtained.

As another method to prepare No. 2 agents of the waving agents, following method may be exemplified. That is, for example, the composition for blending in waving agent, oxidizing agent and water are added and mixed as stirring under heating, if necessary, to prepare No. 2 agent of the waving agent.

The waving agents of the present invention contain at least one selected from the group consisting of No. 1 agents of waving agents of the present invention and No. 2 agents of waving agents of the present invention. For example, the waving agents of the present invention is one consisting of No. 1 agents of waving agents of the present invention and No. 2 agents of waving agents of the present invention, one consisting of No. 1 agents of waving agents of the present invention and No. 2 agents of waving agents except the above-mentioned ones, and another one consisting of No. 1 agents of waving agents except the above-mentioned ones and No. 2 agents of waving agents of the present invention.

As "No. 1 agents of waving agents except the above-mentioned ones" and "No. 2 agents of waving agents except the above-mentioned ones", the No. 1 and No. 2 agents, which are ordinary used in the conventional waving agents, may be exemplified respectively. Concretely, as No. 2 agents of waving agents except the above-mentioned ones, the mixture prepared by dissolving oxidizing agents and surfactants homogeneously in water may be exemplified.

The finishing agents of the present invention contain the compositions for blending in finishing agents, and generally further contain water. Further, as additives such as esters, alcohols, sequestering agents, bases and preservatives may, if necessary, be added.

As esters, higher fatty esters (e.g. isopropyl myristate) may be exemplified. As alcohols, isopropyl alcohol (IPA), polypropylene glycol and glycerin may be exemplified. As the sequestering agents, e.g. disodium edetate may be exemplified. As bases, sodium hydroxide and MEA may be exemplified. As preservative, parabens may be exemplified.

In formulations of the finishing agents of the present invention, the contents of the compositions for blending in finishing agents are, for example, from 20 to 60 wt. %.

As the substantial method to prepare the finishing agents of the present invention, following method may be exemplified. That is, for example, each ingredient is added in order under heating, if necessary, to prepare the finishing agents. All ingredients may be added in such order as each ingredient can be dissolved homogeneously. Concretely, the composition for blending in finishing agent, esters, alcohols, bases, preservatives and water are added in order as stirring and mixed homogeneously to prepare the finishing agents.

Additives that increase the feeling effects is such one as may be blended to hair treating agents such as waving agents, and as can give luster to hair after appliance, and further as can increase the sense of touch. The compositions for blending in additives that increase the feeling effects of the present invention may be used solely as additives that increase the feeling effects.

The contents of additives that increase the feeling effects of the present invention are 10–25 wt. % of total weights of hair treating agents containing the additives that increase the feeling effects, when the additives that increase the feeling effects are blended to hair treating agents such as waving agents.

The depilatories of the present invention contain the compositions for blending in depilatories, and may further contain depilatori's assistant, reducing agent, alkaline agent and water. As depilatori's assistant, urea may be exemplified. As reducing agent, calcium thioglycolate may be exemplified. As alkaline agent, sodium hydroxide may be exemplified.

In the formulations of the depilatories of the present invention, the contents of the compositions for blending in depilatories are, for example, from 1 to 20 wt. %. The pH of the depilatories may be, for example, 12–13, desirably 12.2–12.8.

As the substantial method to prepare depilatories, following method may be exemplified. That is, for example, the composition for blending in depilatorie, that has been heated and dissolved homogeneously, is added to heated water and mixed as stirring and emulsified. After cooling, additives such as depilatorie's assistant, reducing agent, alkaline agent may be added and mixed homogeneously to prepare the depilatories.

The Third Embodiment

In this embodiment, cationic surfactants besides alcohols are contained in the compositions for blending in hair treating agents of the present invention.

As alcohols, for example, polyhydric alcohols, lower and higher alcohols may be exemplified. Concretely, one or two compounds selected from the group consisting of propylene glycol, glycerin (concentrated glycerin etc.), sorbit, D-mannitol, ethanol, myristyl alcohol, cetanol and behenyl alcohol may be exemplified.

For example, in compositions for blending in hair conditioners, and in compositions for blending in finishing agents, cetanol may be contained.

Further, in the compositions for blending in hair treating agents of the present invention, cationic surfactants are contained. As cationic surfactants, di-higher alkyl dimethyl ammonium halide, higher alkyl trimethyl ammonium halide, higher alkyl pyridinium halide, higher alkyl trimethyl ammonium saccarinate may be exemplified.

Concretely, one or two compounds selected from the groups consisting of distearyl dimethyl ammonium chloride, dicocoyl dimethyl ammonium chloride, lauryl trimethyl ammonium bromide, cetyl trimethyl ammonium chloride, cetyl trimethyl ammonium bromide, stearyl trimethyl ammonium chloride, behenyl trimethyl ammonium chloride, lauryl pyridinium chloride and cetyl trimethyl ammonium saccarinate may be exemplified.

For example, in compositions for blending in hair conditioners, cetyl trimethyl ammonium chloride may be contained. For example, in compositions for blending in hair conditioners and in compositions for blending in finishing agents, stearyl trimethyl ammonium chloride and/or behenyl trimethyl ammonium chloride may be contained.

Further, in the compositions for blending in hair treating agents of the present invention, any kind of additives may be contained in accordance with the kind and the purposes of hair treating agents. For example, in the compositions for blending in hair treating agents of the present invention, one to four ingredients selected from the group consisting of amphoteric surfactant, fats and oils, hydrocarbons, waxes, acids, sequestering agents, parabens, polymers and water may be contained.

For example, in compositions for blending in waving agents, lauryl dimethylaminoacetic acid betaine or 2-alkyl N-carboxymethyl N-hydroxyethyl imidazolinium betaine may be contained as amphoteric surfactant. In compositions for blending in hair conditioners, for example, hydrogenated oil (hydrogenated palm oil fatty acid triglyceride, hydrogenated tallow acid triglyceride, hydrogenated rice oil fatty acid triglyceride etc.), olive oil, sasanqua oil, lanolin or hard lanolin may be contained as fats and oils.

In compositions for blending in hair conditioners, in compositions for blending in finishing agents, for example, paraffin or liquid petrolatum may be contained as hydrocarbons. In compositions for blending in hair conditioners, for example, candelilla wax may be contained as waxes. In compositions for blending in hair conditioners and in compositions for blending in waving agents, for example, citric acid, phosphoric acid or partially neutralized salts of them (e.g. disodium phosphate) may be contained as acids.

In compositions for blending in waving agents, for example, disodium edetate or pentasodium diethylenetriamine pentaacetate may be contained as sequestering agents. In compositions for blending in hair conditioners, for example, methyl parahydroxybenzoate and propyl parahydroxybenzoate may be contained as parabens.

In compositions for blending in hair conditioners, for example, carboxyvinylpolymer (average molecular weight, e.g. 500,000–2 million) may be contained as polymers. In compositions for blending in hair conditioners and in compositions for blending in waving agents, for example, water may be contained.

In the formulations of the compositions for blending in hair treating agents of the present invention, when the respective contents of alcohols and cationic surfactants are D and E (wt %), D and E desirably satisfy the ranges of $0.5 \leqq D \leqq 85$, $1 \leqq E \leqq 30$ and $D+E \leqq 100$.

For example, in a case of the compositions for blending in hair conditioners, D and E may be $1 \leqq D \leqq 80$, $1 \leqq E \leqq 30$ and $D+E \leqq 100$.

In a case of compositions for blending in waving agents, D and E may be $0.5 \leqq D \leqq 10$, $1 \leqq E \leqq 20$.

In a case of compositions for blending in finishing agents, D and E may be $45 \leqq D \leqq 85$, $5 \leqq E \leqq 20$ and $D+E \leqq 100$.

As the substantial method to prepare the compositions for blending in hair treating agents of this embodiment, following method may be exemplified. That is, for example, alcohols, cationic surfactants, and, if necessary, various ingredients such as additives are mixed and stirred under reduced pressure and/or heating, if necessary, until the mixtures is completely dissoluved. The heating temperature is desirably lower than the decomposition temperature of the mixture, for example, lower than 90° C. The reduced pressure may be, for example, 400–600 mm Hg. The adding order of each ingredient is not limited. For example, all ingredients may be added at a time. Or, each ingredient may be added in order.

The hair treating agents of the present invention contain the above-mentioned compositions for blending in hair treating agents of the present invention. Hair conditioners, waving agents and finishing agents are illustrated below as the hair treating agents.

The hair conditioners of the present invention contain above-mentioned compositions for blending in hair conditioners. One or more kinds of the compositions for blending in hair conditioners may be used.

Further, in the hair conditioners of the present invention, preservatives, perfumes, silicones (Si compounds), polybasic acid, additive compositions, additives that increases the feeling effects, alcohols and water may be contained.

As preservatives, parabens such as methylparaben and propylparaben may be exemplified. As perfumes, any kinds of perfumes, which are generally used to the hair conditioners, may be exemplified. As silicones, methyl polysiloxane, highly polymerized methyl polysiloxane and decamethyl cyclopentasiloxane may be exemplified.

As polybasic acid, malic acid may be exemplified. Mixture of mixed silicone, higher alcohol, esters, nonionic surfactant and cationic surfactant may be exemplified as additive compositio. As additive that increases the feeling effects, mink oil may be exemplified. As alcohols, ethanol may be exemplified.

In the formulations of the hair conditioners of the present invention, the contents of the compositions for blending in hair conditioners are, for example, from 5 to 30 wt. %.

The preparing method of the hair conditioners of the present invention is not limited. For example, the composition for blending in hair conditioner and additives, if necessary, such as silicones, preservatives, additive that increases the feeling effects and alcohols are mixed and dissoluved homogeneously under heating. Next, this heated dissoluved material and heated water are mixed as stirring, and then emulsified. After the emulsion is cooled as stirring, perfume and, if necessary, polybasic acid are added to prepare the hair conditioner.

In another preparing method of the hair conditioners of the present invention, for example, heated additive composition and heated water are mixed as stirring to prepare emulsion. After this emulsion is cooled down as stirring, the composition for blending in hair conditioner and perfume are added to the cooled emulsion to prepare the hair conditioner of the present invention.

As waving agents of the present invention, waving agent that are composed of No. 1 agents and No. 2 agents may be exemplified (In the present invention, both No. 1 agents alone and No. 2 agents alone are also comprised in the hair treating agents of the present invention). No. 1 agents of the waving agents of the present invention may contain reducing agents, alkaline agents and water besides the compositions for blending in waving agents of the present invention.

As reducing agents, thioglycolic acid, cysteine or salts (ammonium salt, MEA salt, hydrochloric acd salts etc.) of them may be exemplified. As alkaline agents, ammonia, amines (MEA, isopropanolamine, etc.), ammonium salts (ammonium bicarbonate etc.) and basic amino acid may be exemplified.

In formulations of No. 1 agents of the waving agents of the present invention, the contents of the compositions for blending in waving agents may be, for example, from 1 to 20 wt. %.

As the substantial method to prepare No. 1 agents of the waving agents, following method may be exemplified. That is, for example, reducing agents, alkaline agents and the composition for blending in waving agent are added in order to water and then stirred homogeneously to prepare No. 1 agents of the waving agents.

In No. 2 agents of the waving agents of the present invention, oxidizing agents, sequestering agents and water etc. may be contained besides the compositions for blending in waving agents of the present invention. As oxidizing agents, bromic acid salts or hydrogen peroxide may be exemplified. As sequestering agents, e.g. edetic acid salts and hydroxyethane diphosphoric acid may be exemplified.

In formulations of No. 2 agents of the waving agents of the present invention, the contents of the compositions for blending in waving agents are, for example, from 1 to 15 wt. %.

As the substantial method to prepare No. 2 agents of the waving agents, following method may be exemplified. That is, for example, oxidizing agents, sequestering agents and the composition for blending in waving agent are added in order to water and then stirred homogeneously to prepare No. 2 agents of the waving agents.

The waving agents of the present invention contain at least one selected from the group consisting of No. 1 agents of waving agents of the present invention and No. 2 agents of waving agents of the present invention. For example, the waving agents of the present invention is one consisting of No. 1 agents of waving agents of the present invention and No. 2 agents of waving agents of the present invention, one consisting of No. 1 agents of waving agents of the present invention and No. 2 agents of waving agents except the above-mentioned ones, and another one consisting of No. 1 agents of waving agents except the above-mentioned ones and No. 2 agents of waving agents of the present invention.

As "No. 1 agents of waving agents except the above-mentioned ones" and "No. 2 agents of waving agents except the above-mentioned ones", the No. 1 and No. 2 agents, which are ordinary used in the conventional waving agents, may be exemplified respectively. Concretely, as No. 2 agents of waving agents except the above-mentioned ones, the mixture prepared by dissolving oxidizing agents and cationic surfactants homogeneously in water may be exemplified.

The finishing agents of the present invention contain the compositions for blending in finishing agents, and generally further contain water. Further, silicones, fats and oils, hydrocarbons, preservatives, UV absorbents, alcohols and perfumes may be added as additives.

Concretely, the compounds that are exemplified in hair conditioner may be mentioned as silicones, preservatives and alcohols respectly. As fats and oils, jojoba oil may be exemplified. As hydrocarbons, squalane may be exemplified. As UV absorbents, oxybenzone may be exemplified. As perfumes, any kinds of perfumes, which are generally used to the finishing agents, may be exemplified.

In formulations of the finishing agents of the present invention, the contents of the compositions for blending in finishing agents are, for example, from 5 to 25 wt. %.

The preparation method of the finishing agent of the present invention may be the same as hair conditioner.

The Fourth Embodiment

In this embodiment, cationic surfactants and nonionic surfactants besides alcohols are contained in the compositions for blending in hair treating agents of the present invention.

As alcohols, for example, lower and higher alcohols, natural alcohols and polyhydric alcohols (e.g. glycols, glycerins, sorbitanes etc.) may be exemplified.

Concretely, one, two, or four compounds selected from the groups consisting of ethanol, isopropanol, lauryl alcohol, myristyl alcohol, cetanol, oleyl alcohol, arachyl alcohol, behenyl alcohol, cetostearyl alcohol, propylene glycol, 1,3-butylene glycol, 3-methyl-1,3-butandiol, diethylene glycol monoethyl ether, glycerin (conc.glycerin etc.) and sorbitol may be exemplified as alcohols.

For example, in compositions for blending in hair conditioners and in compositions for blending in waving agents, cetanol may be contained. In compositions for blending in waving agents, propylene glycol may be contained. In compositions for blending in finishing agents, in compositions for blending in deodorizing rinse liquids and in compositions for blending in intermediate treating agents for permanents, for example, glycerin may be contained.

Further, in the compositions for blending in hair treating agents of the present invention, cationic surfactants are contained. As cationic surfactants, dialkyl (or alkenyl) dimethyl ammonium salts, dipolyoxyethylene alkyl (or alkenyl) methyl ammonium salts, alkyl (or alkenyl) dimethyl benzyl ammonium salts, alkyl (or alkenyl) trimethyl ammonium salts and alkyl pyridinium salts may be exemplified.

Concretely, one to three compounds selected from the groups consisting of distearyl dimethyl ammonium chloride, dipolyoxyethylene (e.g. 2–10 EO) oleyl methyl ammonium chloride, stearyl dimethyl benzyl ammonium chloride, benzalkonium chloride, lauryl trimethyl ammonium chloride, cetyl trimethyl ammonium chloride, cetyl trimethyl ammonium bromide, stearyl trimethyl ammonium chloride, stearyl trimethyl ammonium bromide, behenyl trimethyl ammonium chloride, cethyl trimethyl ammonium saccarinate and cetyl pyridinium chloride may be exemplified.

For example, in compositions for blending in hair conditioners, in compositions for blending in finishing agents and in compositions for blending in intermediate treating agents for permanents, dipolyoxyethylene oleyl methyl ammonium chloride may be contained. In compositions for blending in hair conditioners and in compositions for blending in waving agents, for example, lauryl trimethyl ammonium chloride or cetyl trimethyl ammonium bromide may be contained.

In compositions for blending in hair conditioners, in compositions for blending in waving agents and in compositions for blending in deodorizing rinse liquids, for example, cetyl trimethyl ammonium chloride may be contained. In compositions for blending in hair conditioners, in compositions for blending in waving agents and in compositions for blending in finishing agents, for example, stearyl trimethyl ammonium chloride may be contained.

Further, in the compositions for blending in hair treating agents of the present invention, nonionic surfactants are contained. As nonionic surfactants, for example, polyoxyethylene alkyl (or alkenyl) ethers, polyoxyethylene derivatives prepared from natural fatty acids, esters prepared from polyhydric alcohols (e.g. glycols, sorbitanes etc.) and higher fatty acids and fatty acid alkylolamides may be exemplified. EO addition polymerization degrees of above-mentioned “polyoxyethylene” may be, for example, 2 to 70 mole.

Concretely, one to three compounds selected from the groups consisting of polyoxyethylene lauryl ether, polyoxyethylene cetyl ether, polyoxyethylene oleyl ether, polyoxyethylene nonylphenyl ether, polyoxyethylene hydrogenated castor oil, polyoxyethylene almond oil, polyoxyethylene lanolin, polyethylene glycol monostearate, polyoxyethylene sorbitan monooleate, lauric acid diethanolamide, stearic acid diethanolamide, coconut fatty acid diethanolamide and sorbitan monolaurate may be exemplified.

For example, in compositions for blending in hair conditioners, in compositions for blending in waving agents, in compositions for blending in finishing agents and in compositions for blending in deodorizing rinse liquids, polyoxyethylene lauryl ether may be contained. In compositions for blending in waving agents, for example, polyoxyethylene cetyl ether may be contained. In compositions for blending in hair conditioners and in compositions for blending in waving agents, for example, polyoxyethylene oleyl ether may be contained.

In compositions for blending in hair conditioners, in compositions for blending in waving agents, in compositions for blending in deodorizing rinse liquids and in compositions for blending in intermediate treating agents for permanents, for example, polyoxyethylene nonylphenyl ether may be contained. In compositions for blending in hair conditioners, for example, polyoxyethylene lanolin and/or polyethylene glycol monostearate may be contained.

Further, in the compositions for blending in hair treating agents of the present invention, any kind of additives may be contained in accordance with the kind and the purposes of hair treating agents. For example, in the compositions for blending in hair treating agents of the present invention, one to five ingredients selected from the group consisting of fats and oils, acids, alkalis, hydrocarbons, parabens, polymers, silicones (Si compounds), sequestering agents, antibacterial agents, inorganic salts and water may be contained.

For example, in compositions for blending in hair conditioners and in compositions for blending in waving agents, fats and oils and/or sequestering agents may be contained. In compositions for blending in hair conditioners, in compositions for blending in waving agents, in compositions for blending in deodorizing rinse liquids and in compositions for blending in intermediate treating agents for permanents, for example, acids may be contained. In compositions for blending in waving agents, for example, alkalis may be contained. In compositions for blending in hair conditioners, in compositions for blending in waving agents and in compositions for blending in finishing agents, for example, hydrocarbons may be contained.

In compositions for blending in hair conditioners and in compositions for blending in finishing agents, for example, polymers may be contained. In compositions for blending in waving agents and in compositions for blending in finishing agents, for example, silicones may be contained. In compositions for blending in finishing agents, for example, antibacterial agents may be contained. In compositions for blending in deodorizing rinse liquids and in compositions for blending in intermediate treating agents for permanents, for example, inorganic salts may be contained. In compositions for blending in hair conditioners, in compositions for blending in waving agents, in compositions for blending in finishing agents, in compositions for blending in deodorizing rinse liquids and in compositions for blending in intermediate treating agents for permanents, water may be contained.

As fats and oils, one or two compounds selected from the group consisting of hydrogenated oil (hydrogenated palm oil fatty acid triglyceride, hydrogenated tallow fatty acid triglyceride etc.), jojoba oil, castor oil, safflower oil and lanolin may be exemplified concretely. As acids, one or two compounds selected from the groups consisting of lactic acid, isostearic acid, oleic acid, sorbic acid, phosphoric acid and dibasic sodium phosphate may be exemplified concretely.

As alkali, sodium hydroxide may be exemplified concretely. As hydrocarbons, liquid petrolatum or light liquid isoparaffin may be exemplified concretely. As parabens, methyl parahydroxybenzoate and/or propyl parahydroxybenzoate may be exemplified concretely. As polymers, N-methacryloyl oxyethyl N,N-dimethyl ammonium-α-N-methyl carboxy betaine-butyl methacrylate copolymer or poly N,N'-dimethyl-3,5-methylene-piperidinium chloride may be exemplified concretely.

As silicones, dimethylsiloxane.methylstearoxysiloxane copolymer, dimethylsiloxane.methyl (polyoxyethylene) siloxane (5–300 EO) copolymer or methyl polysiloxane may be exemplified concretely. As sequestering agents, disodium edetate may be exemplified concretely. As antibacterial agents, phenoxyethanol may be exemplified concretely. As inorganic salts, zinc sulfate and/or magnesium sulfate may be exemplified concretely.

In the formulations of the compositions for blending in hair treating agents of the present invention, when the respective contents of alcohols, cationic surfactants and nonionic surfactants are F, G and H (wt %), F, G and H desirably satisfy the ranges of $0.1 \leqq F \leqq 85$, $0.01 \leqq G \leqq 45$, $0.1 \leqq H \leqq 60$ and $F+G+H \leqq 100$.

For example, in a case of the compositions for blending in hair conditioners, F, G and H may be $0.1 \leqq F \leqq 85$, $1 \leqq G \leqq 45$, $1 \leqq H \leqq 45$ and $F+G+H \leqq 100$.

In a case of the compositions for blending in waving agents, F, G and H may be, for example, $0.1 \leqq F \leqq 50$, $1 \leqq G \leqq 20$, $1 \leqq H \leqq 60$ and $F+G+H \leqq 100$.

In a case of the compositions for blending in finishing agents, F, G and H may be, for example, $1 \leqq F \leqq 30$, $0.01 \leqq G \leqq 30$, $1 \leqq H \leqq 10$ and $F+G+H \leqq 100$.

In a case of the compositions for blending in deodorizing rinse liquids and in a case of compositions for blending in intermediate treating agents for permanents, F. G and H may be, for example, $1 \leqq F \leqq 10$, $1 \leqq G \leqq 10$, $0.1 \leqq H \leqq 5$ and $F+G+H \leqq 100$.

As the substantial method to prepare the compositions for blending in hair treating agents of this embodiment, following method may be exemplified. That is, for example, alcohols, cationic surfactants, nonionic surfactants and, if necessary, various ingredients such as additives are mixed and stirred under heating until the mixtures are completely dissoluved. The heating temperature is desirably lower than the decomposition temperature of the mixture, for example, lower than 100° C. The adding order of each ingredient is not limited.

As another preparing method of the composition for blending in hair treating agent of the present invention, for example, alcohols, nonionic surfactants and various oiliness ingredients (e.g. fats and oils, hydrocarbons) are mixed and dissoluved homogeneously under heating. Next, this homogeneously dissoluved mixture is added to heated water as stirring to prepare emulsion. Then, this emulsion is cooled.

On the other hand, cationic surfactants and water are mixed as stirring under heating and dissoluved homogeneously, and then cooled. Then, this homogeneously dissoluved mixture is added as stirring to the above-mentioned cooled emulsion, and then mixed homogeneously to prepare the compositions for blending in hair treating agents. The heating temperature is desirably lower than the decomposition temperatures of the mixture, for example, lower than 100° C.

The hair treating agents of the present invention contain the above-mentioned compositions for blending in hair treating agents of the present invention. Hair conditioners, waving agents, finishing agents, deodorizing rinse liquids and intermediate treating agents for permanents are illustrated below as the hair treating agents.

Hair conditioners of the present invention include 1-bath type of hair conditioners. The 1-bath type of hair conditioners contain above-mentioned compositions for blending in hair conditioners. One or more kinds of the compositions for blending in hair conditioners may be used.

Further, in the 1-bath type of the hair conditioners of the present invention, preservatives, perfumes, sequestering agents, polypeptide aqueous solutions (PPT) may be contained as additives.

As preservatives, parabens such as methylparaben and propylparaben may be exemplified. As perfumes, any kinds of perfumes, which are generally used to the hair conditioners, may be exemplified. As sequestering agents, disodium edetate may be exemplified In the formulations of the 1-bath type of the hair conditioners of the present invention, the contents of the compositions for blending in hair conditioners are, for example, from 5 to 30 wt. %.

The preparing method of the 1-bath type of he hair conditioners of the present invention is not limited. For example, sequestering agents is, if necessary, added to water and heated. On the other hand, preservatives is, if necessary, added to the composition for blending in hair conditioner, and heated, and then dissoluved homogeneously.

Next, this homogeneously dissoluved mixture is added to the above-mentioned heated water (or aqueous solution) as stirring to prepare emulsion. After this emulsion is cooled, perfume and PPT etc. are added to prepare the 1-bath type of the hair conditioner. The heating temperatures of water and the composition for blending in hair conditioner is desirably lower than the decomposition temperatures of the ingredients, for example, lower than 95° C.

As another hair conditioners of the present invention, is included 2-bath (or 2-agents) type of treatments. 2-bath type of treatment consists of Liquid 1 and Liquid 2. Liquid 1 of 2-bath type of treatment of the present invention may contain, for example, alcohols, preservatives, gum substances, PPT and water etc. as additives. As alcohos, ethanol and glycols (e.g. 1,3-butylene glycol) may be exemplified. As preservative, parabens may be exemplified. As gum substances, carrageenan may be exemplified.

In the formulations of the Liquid 1 of 2-bath type of treatment, the content of alcohols may be 5–30 wt. %. The content of preservatives may be 0.05–1 wt. %. The content of gum substances may be 0.1–5 wt. %. The content of PPT may be 0.5–5 wt. %.

As the substantial method to prepare Liquid 1 of 2-bath type of treatment of the present invention, following method may be exemplified. That is, for example, alcohols, preservatives, gum substances, PPT and water are mixed and dissoluved homogeneously to prepare Liquid 1 of 2-bath type of treatment. The adding order of each ingredient is not limited.

Liquid 2 of 2-bath type of treatment of the present invention contains composition for blending in hair conditioner of the present invention. Further, in the Liquid 2 of the present invention, preservatives, perfumes and silicones etc. may be contained as additives. Such compounds that are exemplified in Liquid 1 of 2-bath type of treatment, may be mentioned as preservatives and perfumes respectively. As silicones, (highly polymerized) dimethyl polysiloxane and decamethyl cyclopentasiloxane may be exemplified.

The contents of the compositions for blending in hair conditioners in the Liquid 2 of 2-bath type of treatments and preparing methods of Liquid 2 of 2-bath type of treatments may be the same as the case of the above-mentioned 1-bath type of hair conditioners.

Waving agents of the present invention may be composed of No. 1 agents and No. 2 agents (In the present invention, both No. 1 agents alone and No. 2 agents alone are also comprised in the hair treating agents of the present invention).

No. 1 agents of the waving agents of the present invention may contain reducing agents, alkaline agents and water besides the compositions for blending in waving agents of the present invention. As reducing agents, thioglycolic acid, cysteine or salts (ammonium salt, MEA salt, hydrochloric acd salts etc.) of them may be exemplified. Ammonia, amines (MEA, isopropanolamine, etc.), ammonium salts (ammonium bicarbonate etc.) and basic amino acid may be exemplified as alkaline agents,.

In formulations of No. 1 agents of the waving agents of the present invention, the contents of the compositions for blending in waving agents may be, for example, from 0.1 to 25 wt. %.

In No. 2 agents of the waving agents of the present invention, oxidizing agents, surfactant, organic and inorganic acids, sequestering agents and water etc. may be contained besides the compositions for blending in waving agents of the present invention. As oxidizing agents, bromic acid salts (e.g. sodium bromate) and hydrogen peroxide may be exemplified. As surfactants, lauryl trimethyl ammonium halide (lauryl trimethyl ammonium chloride, lauryl trimethyl ammonium bromide etc.) may be exemplified. As organic acid, citric acid and tartaric acid may be exemplified. As inorganic acid, phosphoric acid and dibasic sodium phosphate may be exemplified. As sequestering agents, e.g. disodium edetate and 1-hydroxyethane-1,1-diphosphonic acid may be exemplified.

In formulations of No. 2 agents of the waving agents, the contents of the compositions for blending in waving agents are, for example, from 0.1 to 25 wt. %.

As the method to prepare No. 1 agents of the waving agents of the present invention, following method may be exemplified. That is, for example, the composition for blending in waving agent, that have been heated and dissolved homogeneously, is added to heated water, stirred and emulsified. Then, viscous liquid is prepared by cooling. Next, reducing agents and alkaline agents may be added to the viscous liquid at room temperature, and mixed homogeneously as stirring to prepare No. 1 agent of the waving agent. The contents of the compositions for blending in waving agents in viscous liquid may be, for example, from 1 to 10 wt. %.

As the method to prepare No. 2 agents of the waving agents of the present invention, following method may be exemplified. That is, for example, the viscous liquid is prepared by similar manner to No. 1 agents of the waving agents. Next, oxidizing agents may be added to the viscous liquid at room temperature, and mixed homogeneously as stirring to prepare No. 2 agent of the waving agent. The contents of the compositions for blending in waving agents in viscous liquid may be, for example, from 1 to 10 wt. %.

As another method to prepare No. 1 agents of the present waving agents, following method may be exemplified. That is, for example, the composition for blending in waving agents, reducing agent, alkaline agent and water are added, and then mixed as stirring under heating, if necessary, to prepare No. 1 agents of the present waving agents.

As another method to prepare No. 2 agents of the waving agents, following method may be exemplified. That is, for example, the composition for blending in waving agent, oxidizing agents and water are added and mixed as stirring under heating, if necessary, to prepare No. 2 agent of the waving agent.

The waving agents of the present invention contain at least one selected from the group consisting of No. 1 agents of waving agents of the present invention and No. 2 agents of waving agents of the present invention. For example, the waving agents of the present invention is one consisting of No. 1 agents of waving agents of the present invention and No. 2 agents of waving agents of the present invention, one consisting of No. 1 agents of waving agents of the present invention and No. 2 agents of waving agents except the above-mentioned ones, and another one consisting of No. 1 agents of waving agents except the above-mentioned ones and No. 2 agents of waving agents of the present invention.

As “No. 1 agents of waving agents except the above-mentioned ones” and “No. 2 agents of waving agents except the above-mentioned ones”, the No. 1 and No. 2 agents, which are ordinary used in the conventional waving agents, may be exemplified respectively. Concretely, as No. 2 agents of waving agents except the above-mentioned ones, the mixture prepared by dissolving oxidizing agents and surfactants homogeneously in water may be exemplified.

The finishing agents of the present invention contain the compositions for blending in finishing agents, and generally further contain water. Further, additives such as alcohols, preservatives and such compounds as are illustrated in hair conditioner as additives may, if necessary, be added.

As alcohols, etanol may be exemplified. As preservative, parabens may be exemplified.

In formulations of the finishing agents of the present invention, the contents of the compositions for blending in finishing agents are, for example, from 1 to 35 wt. %.

As the substantial method to prepare the finishing agents of the present invention, following method may be exemplified. That is, for example, alcohols, preservatives and water are added in order as stirring, and then mixed homogeneously under heating, if necessary, to prepare the finishing agents.

Deodorizing rinse liquids of the present invention is such one as can remove the unpleasant odor that occur when permanents are applied. Further, the deodorizing rinse liquids of the present invention are such ones as have deodorizing effects when the deodorizing rinse liquids are used in finishing rinses.

Deodorizing rinse liquids of the present invention containes the compositions for blending in deodorizing rinse liquids. Further, the deodorizing rinse liquids may contain polymer, nonionic surfactant, alcohols, preservatives, sequestering agents, acids, perfume, aromatic material dispersants.

As polymers, for example, dimethyl diallyl ammonium chloride-acrylamide copolymer may be exemplified. As nonionic surfactants, polyoxyethylene castor oil may be exemplified concretely. As alcohols, for example, 1,3-butylene glycol may be exemplified. As preservative, parabens may be exemplified. As sequestering agents, e.g. disodium edetate may be exemplified. As acids, for example, dibasic sodium phosphate and lactic acid may be exemplified. As perfumes, for example, any kinds of perfumes, which are generally used to the deodorizing rinse liquids, may be exemplified. As aromatic material dispersants, polyoxyethylene nonylphenyl ether may be exemplified.

In the formulations of the deodorizing rinse liquids of the present invention, the contents of the compositions for blending in deodorizing rinse liquids are, for example, from 1 to 35 wt. %.

As the substantial method to prepare the deodorizing rinse liquids of the present invention, following method may be exemplified. That is, for example, after the composition for blending in deodorizing rinse liquid, polymers, nonionic surfactants, alcohols, preservatives, sequestering agents and acids are mixed as stirring homogeneously under heating, if necessary, perfume and aromatic material dispersants are further added and mixed homogeneously to prepare the deodorizing rinse liquid.

The intermediate treating agents for permanents of the present invention is used in the middle of applying permanents. The intermediate treating agents for permanents of the present invention is such one as can increase the wave-setting effectiveness, and further as can show the conditioning effects that can make hair care easy.

The content of the compositions for blending in intermediate treating agents for permanents and the preparation method of the intermediate treating agents for permanents may be similar to aromatic material dispersants.

EXAMPLE

Example of the First Embodiment

The first embodiment of the present invention is illustrated more concretely according to the following Examples. (Preparation of the Compositions for Blending in Hair Treating Agents)

Examples 1–8, 11, 13–16 and 20

The amount (kg) shown in Table 1–4 of each ingredient was heated to the temperature shown in Table 1 and 3, and then dissolved homogeneously by mixing and stirring. Thus, the compositions for blending in hair treating agents (Examples 1–8, 11, 13–16 and 20) of the present invention were prepared.

Example 9

Each ingredient 22, 24, 2 and 1 were added to the ingredient 51 (58.8 kg), which had been heated to the temperature shown in Table 1, and stirred to prepare homogeneously dissoluved mixture. After this homogeneously dissoluved mixture was cooled below 45° C., remaining ingredients were added in order while confirming the dissolution, and then mixed homogeneously. Thus, the composition for blending in hair treating agent of the present invention was prepared. The numbers indicating each ingredient, the ingredients and contents (kg) are shown in Table 1 and 2.

Example 10

Each ingredient 33 and 30 were added to the ingredient 1, which had been heated to the temperature shown in Table 1, and stirred to prepare homogeneously dissoluved mixture. And then, ingredient 44, 51, 9 and 46 were added in order to the afore-mentioned dissoluved mixture. On adding each ingredient, the following ingredient was added after it was confirmed that the previously added ingredients had been dissoluved homogeneously. Thus, the composition for blending in hair treating agent of the present invention was prepared. The numbers indicating each ingredient, the ingredients and contents (kg) are shown in Table 1 and 2.

Example 12

Each ingredient 27 and 51 were mixed and heated to the temperature shown in Table 3 to prepare solution. On the other hand, each ingredient 10, 1 and 35 were mixed as stirring to prepare homogeneous mixture. This homogeneous mixture was added to the afore-mentioned solution, and dissolved homogeneously to prepare the composition for blending in hair treating agent of the present invention. The numbers indicating each ingredient, the ingredients and contents (kg) are shown in Table 3 and 4.

Example 17

Each ingredient except ingredient 51 was stirred to prepare homogeneous mixture. Ingredient 51 was added as stirring to the afore-mentioned homogeneous mixture, and mixed homogeneously to prepare the composition for blending in hair treating agents of the present invention. The numbers indicating each ingredient, the ingredients and contents (kg) are shown in Table 3 and 4.

Example 18

Mixture of ingredient 1 and 2, mixture of ingredient 44 and 51 (14 kg), mixture of ingredient 11, 46 and 51 (6 kg) and mixture of ingredient 48 and 51 were added in order to ingredient 26. On adding each ingredient, the following ingredient was added after it was confirmed that the previously added ingredients had been dissoluved homogeneously. Thus, the composition for blending in hair treating agent of the present invention was prepared. The numbers indicating each ingredient, the ingredients and contents (kg) are shown in Table 3 and 4.

Example 19

Solution, which comprised ingredient 46, 47 and 1, was added to the ingredient 51, and dispersed by mixing homogeneously. And then, ingredient 25 was added to the mixture, and mixed homogeneously as stirring under reduced pressure (500 mmHg). Thus, the composition for blending in hair treating agent of the present invention was prepared. The numbers indicating each ingredient, the ingredients and contents (kg) are shown in Table 3 and 4.

Example 21

Each ingredient 36–38 was mixed homogeneously as stirring. Next, to this mixture, homogeneous mixture of ingredient 1 and 50 was added, and mixed homogeneously as stirring. Thus, the composition for blending in hair treating agent of the present invention was prepared. The numbers indicating each ingredient, the ingredients and contents (kg) are shown in Table 3 and 4.

Example 22

Each ingredient 51 and 31 were added in order to mixture of the ingredient 9 and 46, which had been heated to the temperature shown in Table 3, and dissoluved homogeneously. After this homogeneously dissoluved mixture was cooled below 45° C., ingredient 49 was added and mixed homogeneously. Thus, the composition for blending in hair treating agent of the present invention was prepared. The numbers indicating each ingredient, the ingredients and contents (kg) are shown in Table 3 and 4.

TABLE 1

| | Example | | | | | | | | | | |
|---|---|---|---|---|---|---|---|---|---|---|---|
| | 1 | 2 | 3 | 4 | 5 | 6 | 7 | 8 | 9 | 10 | 11 |
| heating temperature (° C.) | 70~80 | 50~60 | 70 | 70~80 | 50 | 50~60 | — | 55~65 | 80~90 | — | 50 |
| ingredient (kg) | | | | | | | | | | | |
| 1 ethanol | 2 | — | — | — | — | — | — | 32 | 3 | 38 | — |
| 2 isopropanol | — | — | — | — | — | — | — | — | 3 | — | — |
| 3 hexyldecanol | — | — | — | — | — | — | — | — | — | — | — |
| 4 cetanol | — | — | 72 | — | — | — | — | — | — | — | — |
| 5 oleyl alcohol | — | — | — | 23 | — | — | — | — | — | — | — |
| 6 benzyl alcohol | — | — | — | — | — | 15 | — | 20 | 15 | — | — |
| 7 phenoxyisopropanol | — | — | — | — | — | — | 49 | — | — | — | — |
| 8 propylene glycol | — | — | — | 2 | 30 | — | — | — | — | — | — |
| 9 1,3-butylene glycol | — | 75 | — | — | — | 5 | 14 | — | 3 | 20 | — |
| 10 dipropylene glycol | — | — | — | — | — | — | — | — | — | — | — |
| 11 diethylene glycol monoethyl ether | — | — | — | — | — | — | — | — | — | — | — |
| 12 polyoxypropylene diglyceryl ether | — | — | — | — | — | — | — | — | — | — | 15[4)] |
| 13 D-mannitol | 4 | — | — | — | — | — | — | — | — | — | — |
| 14 polyoxyethylene lauryl ether | — | — | 26[1)] | — | — | 0.5[2)] | — | — | — | — | — |
| 15 polyoxyethylene isostearyl ether | — | — | — | — | — | — | — | — | — | — | — |
| 16 polyoxyethylene oleyl ether | — | — | — | 2[5)] | — | — | — | — | — | — | — |
| 17 polyoxyethylene behenyl ether | — | — | — | — | — | — | — | — | — | — | — |
| 18 polyoxyethylene nonylphenyl ether | — | — | — | 73[6)] | 70[7)] | — | — | — | 2[8)] | — | — |
| 19 polyoxyethylene lanolin | — | — | — | — | — | — | — | 8[9)] | — | — | — |
| 20 polyoxyethylene polyoxypropylene glycol | — | — | — | — | — | — | — | — | — | — | 77[3)] |
| 21 coconut fatty acid diethanolamid | — | — | — | — | — | — | — | — | 0.5[10)] | — | — |
| 22 hydroxyethyl cellulose | — | — | — | — | — | — | — | — | 2 | — | — |
| 23 polyethylene glycol | — | — | — | — | — | — | — | — | 2 | — | — |
| 24 propylene glycol alginate | — | — | — | — | — | — | — | — | 2 | — | — |
| 25 carboxyvinylpolymer | — | — | — | — | — | — | — | — | — | — | — |
| 26 polyacrylic acid | — | — | — | — | — | — | — | — | — | — | — |
| 27 polyvinylpyrrolidone | — | — | — | — | — | 5 | — | — | — | — | — |

[1)–10)] in Table 1 indicate,
[1)] 12 kg (4EO) + 14 kg (23 EO),
[2)] 23EO,
[3)] 16EO, 17PO,
[4)] 9PO,
[5)] 4EO,
[6)] 8EO,
[7)] 11EO,
[8)] 15EO,
[9)] 70EO
[10)] Degree of viscosity of 2% aqueous solution, 5,000–10,000 cps.

TABLE 2

| | Example | | | | | | | | | | |
|---|---|---|---|---|---|---|---|---|---|---|---|
| | 1 | 2 | 3 | 4 | 5 | 6 | 7 | 8 | 9 | 10 | 11 |
| ingredient (kg) | | | | | | | | | | | |
| 28 vinyl methyl ether · ethyl maleate copolymer | — | 25[4)] | — | — | — | — | — | — | — | — | — |
| 29 vinyl methyl ether · butyl maleate copolymer | — | — | — | — | — | — | — | — | — | — | — |
| 30 vinyl acetate · crotonic acid copolymer | — | — | — | — | — | — | — | — | — | 5[2)] | — |
| 31 carrageenan | — | — | — | — | — | — | — | — | — | — | — |
| 32 polyvinylpyrrolidone N, N-dimethyl aminoethyl methacrylic acid copolymer diethyl sulfate | — | — | — | — | — | — | — | — | — | — | — |
| 33 octylamide acrylate · hydroxypropyl acrylate · butylaminoethyl methacrylate copolymer | — | — | — | — | — | — | — | — | — | 5[3)] | — |
| 34 dimethyl diallyl ammonium chloride · acrylamide copolymer | 2.5[1)] | — | — | — | — | — | — | — | — | — | — |
| 35 N-methacryloyl ethyl-N,N-dimethyl ammonium α-N-methyl carboxybetaine · alkyl methacrylate copolymer | — | — | — | — | — | — | — | — | — | — | — |

TABLE 2-continued

| | Example | | | | | | | | | | |
|---|---|---|---|---|---|---|---|---|---|---|---|
| | 1 | 2 | 3 | 4 | 5 | 6 | 7 | 8 | 9 | 10 | 11 |
| 36 decamethyl cyclopentasiloxane | — | — | — | — | — | — | — | — | — | — | — |
| 37 methyl polysiloxane | — | — | — | — | — | — | — | — | — | — | — |
| 38 methylphenyl polysiloxane | — | — | — | — | — | — | — | — | — | — | — |
| 39 polyoxyethylene · methyl polysiloxane copolymer | — | — | — | — | — | — | — | — | — | — | 8 |
| 40 stearic acid | — | — | 2 | — | — | — | — | — | — | — | — |
| 41 tartaric acid | — | — | — | — | — | — | — | — | 8 | — | — |
| 42 trimethylglycine | 40 | — | — | — | — | — | — | — | — | — | — |
| 43 triethanolamine | — | — | — | — | — | — | — | — | — | — | — |
| 44 2-amino-2-methyl1propanol | — | — | — | — | — | — | — | — | — | 15 | — |
| 45 N-methy-2-pyrrolidone | — | — | — | — | — | 25 | 37 | 32 | — | — | — |
| 46 methyl parahydroxybenzoate | 1 | — | — | — | — | — | — | — | — | 1 | — |
| 47 propyl parahydroxybenzoate | — | — | — | — | — | — | — | — | — | — | — |
| 48 disodium edetate | — | — | — | — | — | — | — | — | — | — | — |
| 49 hydrolyzed animal protein | — | — | — | — | — | — | — | — | — | — | — |
| 50 oxybenzone | — | — | — | — | — | — | — | — | — | — | — |
| 51 water | 514 | — | — | — | — | 495 | — | 8 | 82 | 304 | — |

1)–4) in Table 2 indicate,
1) Content 8 wt. %,
2) Content 50 wt. %, Degree of viscosity of reduced product 0.3 (in acetone solution, 30° C.), Oxidation equivalent amount 1.16 meq/g,
3) Content 30 wt. %, Glass-transition temperature 120° C., Degree of viscosity of reduced product 0.4 (in ethanol solution, 25° C.), Oxidation equivalent amount 2.05 meq/g,
4) 50 wt. % of ethanol contained.

TABLE 3

| | Example | | | | | | | | | | |
|---|---|---|---|---|---|---|---|---|---|---|---|
| | 12 | 13 | 14 | 15 | 16 | 17 | 18 | 19 | 20 | 21 | 22 |
| heating temperature (° C.) | 50 | 50 | 80 | 80 | — | — | — | — | 20 | — | 80 |
| ingredient (kg) | | | | | | | | | | | |
| 1 ethanol | 5 | 27 | — | — | 704 | 514 | 16 | 2 | — | 795 | — |
| 2 isopropanol | — | — | — | — | — | — | 7 | — | — | — | — |
| 3 hexyldecanol | — | — | 40 | 33 | — | — | — | — | — | — | — |
| 4 cetanol | — | — | — | — | — | — | — | — | — | — | — |
| 5 oleyl alcohol | — | — | — | — | — | — | — | — | — | — | — |
| 6 benzyl alcohol | — | — | — | — | — | — | — | — | — | — | — |
| 7 phenoxyisopropanol | — | — | — | — | — | — | — | — | — | — | — |
| 8 propylene glycol | — | — | — | — | — | — | — | — | 23 | — | — |
| 9 1,3-butylene glycol | — | 16 | — | — | — | 2 | — | — | — | — | 10 |
| 10 dipropylene glycol | 125 | — | — | — | — | — | — | — | — | — | — |
| 11 diethylene glycol monoethyl ether | — | — | — | — | — | — | 8 | — | — | — | — |
| 12 polyoxypropylene diglyceryl ether | — | — | — | — | 0.6[1)] | 2.4[2)] | — | — | — | — | — |
| 13 D-mannitol | — | — | — | — | — | — | — | — | — | — | — |
| 14 polyoxyethylene lauryl ether | — | — | — | — | — | — | — | — | — | — | — |
| 15 polyoxyethylene isostearyl ether | — | — | — | 67[4)] | — | — | — | — | — | — | — |
| 16 polyoxyethylene oleyl ether | — | — | — | — | — | — | — | — | 64[5)] | — | — |
| 17 polyoxyethylene behenyl ether | — | — | 60[3)] | — | — | — | — | — | — | — | — |
| 18 polyoxyethylene nonylphenyl ether | — | — | — | — | — | — | — | — | — | — | — |
| 19 polyoxyethylene lanolin | — | — | — | — | — | — | — | — | 5[6)] | — | — |
| 20 polyoxyethylene polyoxypropylene glycol | — | — | — | — | — | — | — | — | — | — | — |
| 21 coconut fatty acid diethanolamid | — | — | — | — | — | — | — | — | — | — | — |
| 22 hydroxyethyl cellulose | — | — | — | — | — | — | — | — | — | — | — |
| 23 polyethylene glycol | — | — | — | — | — | — | — | — | — | — | — |
| 24 propylene glycol alginate | — | — | — | — | — | — | — | — | — | — | — |
| 25 carboxyvinylpolymer | — | — | — | — | — | — | — | 17 | — | — | — |
| 26 polyacrylic acid | — | — | — | — | — | — | 8[7)] | — | — | — | — |
| 27 polyvinylpyrrolidone | 13 | 1 | — | — | — | — | — | — | — | — | — |

1)–7) in Table 3 indicate,
1) 9PO,
2) 9PO,
3) 10EO:20EO = 1:1 (weight ratio),
4) 10EO:25EO = 1:1 (weight ratio),
5) 7EO,
6) 20EO,
7) Degree of viscosity of 20% aqueous solution, 3,000–7,000 cps.

TABLE 4

| ingredient (kg) | Example 12 | 13 | 14 | 15 | 16 | 17 | 18 | 19 | 20 | 21 | 22 |
|---|---|---|---|---|---|---|---|---|---|---|---|
| 28 vinyl methyl ether · ethyl maleate copolymer | — | — | — | — | — | — | — | — | — | — | — |
| 29 vinyl methyl ether · butyl maleate copolymer | — | — | — | — | 18[6)] | 36[2)] | — | — | — | — | — |
| 30 vinyl acetate · crotonic acid copolymer | — | — | — | — | — | — | — | — | — | — | — |
| 31 carrageenan | — | — | — | — | — | — | — | — | — | — | 4[4)] |
| 32 polyvinylpyrrolidone N, N-dimethyl aminoethyl methacrylic acid copolymer diethyl sulfate | — | 24[5)] | — | — | — | — | — | — | — | — | — |
| 33 octylamide acrylate · hydroxypropyl acrylate · butylaminoethyl methacrylate copolymer | — | — | — | — | — | — | — | — | — | — | — |
| 34 dimethyl diallyl ammonium chloride · acrylamide copolymer | — | — | — | — | — | — | — | — | — | — | — |
| 35 N-methacryloyl ethyl-N,N-dimethyl ammonium α-N-methyl carboxybetaine · alkyl methacrylate copolymer | 50[1)] | — | — | — | — | — | — | — | — | — | — |
| 36 decamethyl cyclopentasiloxane | — | — | — | — | — | — | — | — | — | 63 | — |
| 37 methyl polysiloxane | — | — | — | — | — | — | — | — | — | 24[3)] | — |
| 38 methylphenyl polysiloxane | — | — | — | — | — | — | — | — | — | 5[7)] | — |
| 39 polyoxyethylene · methyl polysiloxane copolymer | — | 1 | — | — | 4 | 1.6[8)] | — | — | — | — | — |
| 40 stearic acid | — | — | — | — | — | — | — | — | — | — | — |
| 41 tartaric acid | — | — | — | — | — | — | — | — | — | — | — |
| 42 trimethylglycine | — | — | — | — | — | — | — | — | — | — | — |
| 43 triethanolamine | — | — | — | — | 6 | — | — | — | — | — | — |
| 44 2-amino-2-methyl1propanol | — | — | — | — | — | 16 | 7 | — | — | — | — |
| 45 N-methy-2-pyrrolidone | — | — | — | — | — | — | — | — | — | — | — |
| 46 methyl parahydroxybenzoate | — | — | — | — | — | — | 1 | 1 | — | — | 1 |
| 47 propyl parahydroxybenzoate | — | — | — | — | — | — | — | 1 | — | — | — |
| 48 disodium edetate | — | — | — | — | — | — | 1 | — | — | — | — |
| 49 hydrolyzed animal protein | — | — | — | — | — | — | — | — | — | — | 5 |
| 50 oxybenzone | — | — | — | — | — | — | — | — | — | 5 | — |
| 51 water | 312 | 31 | — | — | 10 | 5 | 538 | 961 | 8 | — | 809 |

[1)]–[8)] in Table 4 indicate,
[1)]Content 30 wt. %, Degree of viscosity 200–400 cos,
[2)]50 wt. % of IPA contained,
[3)]8 kg (3,000 cs.) + 16 kg (5 cs),
[4)]30 wt. % of xanthan gum contained,
[5)]60 wt. % of water + 20 wt. % of ethanol contained,
[6)]50 wt. % of ethanol contained,
[7)]14 cs,
[8)]HLB 14.5.

(Preparation of Hair Conditioners)

Examples 23

Cetanol (5 kg), glyceryl monostearate (1 kg), and cethyl trimethyl ammonium chloride (3 kg) were mixed, and then dissolved homogeneously by heating to 80–85° C. After 1 kg of the composition for blending in hair conditioner (Example 2) was added and dispersed in this homogeneously dissolved mixture, the composition for blending in hair conditioner, 80 kg of initial water that had been heated to 80–85° C. was added as stirring to the dispersion, and then mixed homogeneously. Next, the homogeneous mixture was cooled down to 45° C., purified water (add water) was added so as to adjust the total weight to be 100 kg. Thus, the hair conditioner of the present invention was prepared.

(Preparation of Oxidizing Hair Coloring Agents)

Example 24 and 25

Preparation of No. 1 Agents of Oxidizing Hair Coloring Agents

After propylene glycol and initial water were heated to the temperature shown in Table 1 and dissolved homogeneously, dye intermediates (p-phenylene diamine 1.2 kg+, m-aminophenol 0.4 kg+o-aminophenol 0.4 kg+resorcinol 1 kg) was added and dissolved homogeneously.

After the composition for blending in hair coloring (Example 4) (or mixture of this composition and isopropanol) was added to this homogeneous dissoluved material and mixed as stirring, the mixture was cooled to 45° C. Next, ATG, EDTA and ammonia aqueous solution was added, and further purified water (add water) was added so as to adjust the total weight to be 100 kg. Thus No. 1 agent was prepared. The ingredients and contents (kg) are shown in Table 5.

Preparation of No. 2 Agents of Oxidizing Hair Coloring Agents 6 wt. % of hydrogen peroxide was used as No. 2 agents of oxidizing hair coloring agents.

(Preparation of Decolorizing Agents)

Example 26

Preparation of No. 1 Agent of Decolorizing Agent

Propylene glycol and initial water were mixed and heated to the temperature shown in Table 5. After mixture of the composition for blending in hair coloring (Example 4) and ethanol were added to this homogeneous dissoluved material and mixed as stirring, the mixture was cooled as stirring to 35° C. Next, alkaline agent was added, and further water (add water) was added so as to adjust the total weight to be 100 kg. Thus No. 1 agent of decolorizing agent (transparent gelatinizer) was prepared. The ingredients and contents (kg) are shown in Table 5.

Preparation of No. 2 Agent of Decolorizing Agent 6 wt. % of hydrogen peroxide was used as No. 2 agent of decolorizing agents.

Example 27

Preparation of No. 1 Agents of Decolorizing Agents

No. 1 agent of decolorizing agents was prepared in the same manner as Example 24 except that dye intermediates was not used. The ingredients and contents (kg) are shown in Table 5.

Preparation of No. 2 Agent of Decolorizing Agents 6 wt. % of hydrogen peroxide was used as No. 2 agent of decolorizing agent.

TABLE 5

| | Example | | | |
|---|---|---|---|---|
| | 24 | 25 | 26 | 27 |
| heating temperature (° C.) | 80~90 | 80~85 | 80~85 | 80~90 |
| cooling temperature (° C.) | 35 | 35 | 35 | 35 |
| ingredient (kg) | | | | |
| composition blended in hair coloring | Example 4 65 | Example 4 65 | Example 4 65 | Example 4 65 |
| dye intermediate | 3 | 3 | — | — |
| ethanol | — | — | 7 | — |
| isopropanol | — | 7 | — | — |
| propylene glycol | 15 | 8 | 8 | 15 |
| 50% ATG | 5 | proper amount | — | 5 |
| EDTA·2Na | 3 | proper amount | — | 3 |
| ammonia solution | 6 | proper amount | proper amount | 6 |
| initial purified water | 7 | 7 | 7 | 7 |

(Preparation of Waving Agents)

Example 28

Preparation of No. 1 Agents of Waving Agents 70 kg of initial water and 0.02 kg of monoethanolamine were heated to 80–85° C., and then mixed as stirring. After 5 kg of the composition for blending in waving agent (Example 3) was added to this aqueous solution and mixed as stirring homogeneously, the mixture was cooled to 35° C. Next, 13 kg of 50% ATG and proper amount of strong ammonia aqueous solution were added to the cooled mixture. And then water (add water) was further added so as to adjust the total weight to be 100 kg, and mixed homogeneously. Thus No. 1 agent of waving agents was prepared.

Preparation of No. 2 Agent of Waving Agents 1 kg of lauryl trimethyl ammonum chloride, 8 kg of sodium bromate and water were mixed homogeneously to prepare 100 kg of aqueous solution of No. 2 agent of waving agents.

(Preparation of Finishing Agents)

Example 29–31

Each ingredient shown in Table 6 was mixed as stirring at room temperature. Thus, the finishing agents (Examples 29–31) of the present invention were prepared. The ingredients and contents (kg) are shown in Table 6.

Example 32 and 33

Each ingredient shown in Table 6 except 10% sodium hydroxide was mixed as stirring. Next, 10% sodium hydroxide was added as stirring to this mixture, and then mixed homogeneously. Thus, the finishing agents of the present invention were prepared. The ingredients and contents (kg) are shown in Table 6.

TABLE 6

| | Example | | | | |
|---|---|---|---|---|---|
| | 29 | 30 | 31 | 32 | 33 |
| ingredient (kg) | | | | | |
| composition blended in finishing agent | Example 1 20 | Example 1 20 | Example 10 10 | Example 19 15 | Example 19 20 |
| additive composition | — | 052) | — | 30[3)] | 30[3)] |
| silicones[1)] | 5 | 5 | — | — | — |
| parabens | 15 | 15 | — | 1 | 1 |
| ethanol | 5 | 5 | 20 | — | — |
| polyoxyethylene nonylphenyl ether | — | — | — | 5 | 5 |
| vegitable extract | — | — | — | proper amount | proper amount |

TABLE 6-continued

| | Example | | | | |
|---|---|---|---|---|---|
| | 29 | 30 | 31 | 32 | 33 |
| oxybenzone. | — | — | — | 1 | 1 |
| perfume | — | — | — | proper amount | proper amount |
| 10% sodium hydroxide | — | — | — | 1 | 13 |
| jojoba oil | — | — | — | — | 5 |
| squalane | — | — | — | — | 5 |
| water | remaining volume | remaining volume | remaining volume | remaining volume | remaining volume |
| total amount | 100 | 100 | 100 | 100 | 100 |

1)–3) in Table 6 indicate,
1)trade name, "SILICON KF351A" (Shinetsu co.),
2)Ingredient (wt. %); 2-alkyl N-carboxymethyl N-hydroxyethyl imidazolinium betaine (13), cocamidopropyl betaine (17), polyoxyethylene (25EO) lauryl ether (0.5), 85% phosphoric acid (0.2), water (69.3),
3)Ingredient (wt. %); decamethyl cyclopentasiloxane (89), highly polymerized dimethyl polysiloxane (9), dimethyl polysiloxane (2).

Example 34

Initial water and AMP were added as stirring in order to additive composition[1], and then mixed homogeneously. Next, the composition for blending in finishing agents (Example 11) was added to this homogeneous mixture, and then homogeneous mixture comprising the composition for blending in finishing agent (Example 10), parabens and perfume were added. Finaly, water (add water) was further added so as to adjust the total weight to be 100 kg, and mixed homogeneously. Thus, the finishing agent of the present invention was prepared. The ingredients and contents (kg) are shown in Table 7.

Example 35

After carrageenan was dispersed in the composition for blending in finishing agents (Example 11), this dispersion was soluved in initial water. Next, additive composition[1] was added, and then AMP was added gradually to prepare viscous liquid. On the other hand, the composition for blending in finishing agent (Example 10), parabens, perfume and N-methyl-2-pyrrolidone were mixed as stirring to prepare homogeneous mixture. This homogeneous mixture was added to the above-mentioned viscous liquid, and further colorant was added. Finaly, water (add water) was further added so as to adjust the total weight to be 100 kg, and mixed homogeneously. Thus, the finishing agent of the present invention was prepared. The ingredients and contents (kg) are shown in Table 7.

Example 36

The composition for blending in finishing agents (Example 15) and additive composition[3] were mixed and heated to 80–85° C. to prepare the homogeneous dissoluved material. On the other hand, xanthan gum, parabens and initial water were mixed and heated as stirring to 80–85° C. to prepare the homogeneous aqueous composition. Next, the above-mentioned homogeneous aqueous composition was added as stirring to the afore-mentioned homogeneous dissoluved material, and emulsified.

After the emulsion was cooled as stirring to 45° C., the composition for blending in finishing agent (Example 12) was added, and further water (add water) was added so as to adjust the total weight to be 100 kg, and mixed homogeneously. Thus, the finishing agent of the present invention was prepared. The ingredients and contents (kg) are shown in Table 7.

Example 37

The composition for blending in finishing agent (Example 19) and initial water were mixed and heated to 60° C. to prepare the homogeneously dissoluved material. On the other hand, ethanol and parabens were mixed as stirring to prepare the homogeneous mixture 1. Further, additive composition[3], polyoxyethylene (2 EO) stearyl ether and polyoxyethylene (10 EO) glycol monostearate were mixed and heated to 60° C. to prepare the homogeneous mixture 11.

The above-mentioned homogeneous mixture I and II were added as stirring in order while confirming the dispersion to the afore-mentioned homogeneously dissoluved material, and then neutralized by adding sodium hydroxide. Next, perfume was added, and finally water (add water) was added so as to adjust the total weight to be 100 kg, and mixed homogeneously. Thus, the finishing agent of the present invention was prepared. The ingredients and contents (kg) are shown in Table 7.

TABLE 7

| | Example | | | |
|---|---|---|---|---|
| | 34 | 35 | 36 | 37 |
| heating temperature (° C.) | — | — | 80~85 | 60 |
| cooling temperature (° C.) | — | — | 45 | 40 |
| ingredient (kg) | | | | |
| composition blended in finishing agent | Example 10 6 | Example 10 6 | Example 12 3 | Example 19 5 |
| | Example 11 13 | Example 11 13 | Example 15 6 | |
| additive composition | 20[1)] | 20[1)] | 20[3)] | 30[3)] |
| ethanol | — | — | — | 5 |
| Nmethyl2pyrrolidone, | — | 10 | — | — |
| AMP | 2 | 2 | — | — |

TABLE 7-continued

| | Example | | | |
|---|---|---|---|---|
| | 34 | 35 | 36 | 37 |
| parabens | 15 | 1 | 1 | 1 |
| perfume | proper amount | proper amount | — | proper amount |
| color | — | 0.05[2)] | — | — |
| carrageenan | — | 5 | — | — |
| xanthan gum | — | — | 5 | — |
| polyoxyethylene stearyl ether | — | — | — | 5 |
| polyoxyethylene glycol monostearate | — | — | — | 5 |
| 10% sodium hydroxide | — | — | — | 33 |
| initial water | 20 | 40 | 45 | 20 |

[1)-3)] in Table 7 indicate,
[1)]Ingredient (wt. %); carboxyvinylpolymer (5), 85 wt. % phosphoric acid (3), 1-hydroxyethane-1, 1-diphosphonic acid (0.1), dibasic sodium phosphate (0.1), water (91.8),
[2)]Blown; Black No.401 (0.01 kg) + Violet No.401 (0.01 kg) + Orange No.205 (0.03 kg),
[3)]the same additive composition as Example 33.

(Preparation of Additive that Increases the Feeling Effects)

Example 38

Without adding any additives, the composition for blending in additive that increases the feeling effects (Example 1) was used alone as additive that increases the feeling effects (Example 38). Concretely, 5 kg of the additive that increases the feeling effects (Example 38) was added to 95 kg of No. 1 agent of the waving agent (Example 28), and then stirred homogeneously to prepare new No. 1 agent of the waving agent.

Next, hair treatings were carried out to 50 monitors with the above-mentioned new No. 1 agent of the waving agent and No. 2 agent of the waving agent (Example 28) by the following methods, and then the organoleptic tests about hair treating effects of the hair treating agents were carried out. The results of organoleptic tests were summarized in Table 8.

(Preparation of Aromatic Material Dispersants)

Example 39

5 kg of the composition for blending in aromatic material dispersant (Example 5) and 1 kg of perfume were stirred at room temperature to prepare the homogeneous mixture. Next, water (add water), that had been heated to 80° C., was added to the homogeneous mixture so as to adjust the total weight to be 100 kg. And aromatic material was added and dispersed homogeneously to prepare the aromatic material dispersant of the present invention.

Solubilization or dispersion of aromatic material was confirmed by visual inspection when 5 kg of the above-mentioned aromatic material dispersant (Example 39) was added respectively to 95 kg of the afore-mentioned No. 1 agent of the waving agent (Example 28) and 95 kg of the afore-mentioned No. 2 agent of the waving agent (Example 28).

(Preparation of Refreshers)

Example 40

11 kg of the composition for blending in refresher (Example 7), 17 kg of additive composition[1)], 5 kg of polyoxyethylene (50 EO) oleyl ether and 0.15 kg of parabens were mixed and heated to 80° C., and then stirred to prepare the homogeneously dissoluved material. On the other hand, 2.5 kg of sodium sulfite, 0.3 kg of sodium bisulfite and proper amount of water were mixed and heated to 80° C. to prepare aqueous solution. Next, the above-mentioned aqueous solution was added as stirring to the afore-mentioned homogeneously dissoluved material, and emulsified. Finally, water (add water) was added so as to adjust the total weight to be 100 kg, and mixed homogeneously. Thus, the refresher of the present invention was prepared.

1) Ingredient (wt. %); hard lanolin fatty acid (30), cetanol (18), isopropyl myristate (6), paraffin (3), polyoxyethylene (5 EO) cetyl ether (18), 70 wt. % cetyl trimethyl ammonium chloride (25).

(Preparation of Intermediate Treating Agents for Permanents)

Example 41

Without adding any additives, the compositions for blending in intermediate treating agent for permanents (Example 20) was used solely as intermediate treating agent for permanents (Example 41). Concretely, 10 kg of the intermediate treating agent for permanents (Example 41) was added respectively to 100 kg of the afore-mentioned No. 1 agent of the waving agent (Example 28) and 100 kg of the afore-mentioned No. 2 agent of the waving agent (Example 28), and then mixed as stirring homogeneously at room temperature to prepare new waving agent. It was confirmed by visual inspection that the waving agents had chaged from fluid state to gel stage.

And then, the organoleptic tests of this new waving agent were carried out as follows. The results of organoleptic tests were summarized in Table 8.

(Preparation of Acidic Hair Coloring Materials)

Example 42

After 2 kg of hydroxyethyl cellulose was added to 40 kg of water, that had been heated to 90° C., and then dissolved homogeneously as stirring, 25 kg of the composition for blending in hair coloring (Example 8) was added as stirring and mixed homogeneously. Next, aqueous solution comprising of 2.5 kg of dibasic sodium phosphate, 85% phosphoric acid, 2 kg of tartaric acid and 10 kg of water was added and mixed homogeneously. Further, mixture of colorants [Black No. 401 (0.12 kg)+Violet No. 401 (0.15 kg)+Orange No. 205 (0.3 kg)] and 10 kg of water was added and mixed homogeneously. After this mixture was cooled to 45° C., water (add water) was added so as to adjust the total weight to be 100 kg. Thus, the acidic hair coloring material of the present invention was prepared.

(Preparation of Refreshers)

Example 43

20 kg of the composition for blending in refresher (Example 6) and 25 kg of additive composition[1)] were mixed and heated to the temperature about 70° C., and then mixed homogeneously. This mixture was added as stirring to 45 kg of water, that had been heated to 70° C., and then emulsified. After this emulsion was cooled to 45° C., aqueous solution comprising of 2 kg of sodium bisulfite and 4 kg of water and aqueous solution comprising of 1.2 kg of 80% MEA and 2 kg of water were added as stirring in order and mixed homogeneously. Finally, water (add water) was added so as to adjust the total weight to be 100 kg, and mixed homogeneously. Thus, the refresher of the present invention was prepared.

1) Ingredient (wt. %); cetanol (60), paraffin (5), isopropyl myristate (10), butyl stearate (5), polyoxyethylene (23 EO)

lauryl ether (0.5), 70 wt. % cetyl trimethyl ammonium chloride (15).

(The Organoleptic Tests about Hair Treating Effects of the Hair Treating Agents)

Hair treating were carried out to 50 monitors by the following methods. And the results of the organoleptic tests about hair treating effects (i.e. feel when used) of the hair treating agents were obtained. The results of organoleptic tests were summarized in Table 8.

The Method for Hair Treating with Hair Conditioners

After ordinary shampoo, a specimen of hair conditioners (Examples 23) was applied to hair and spread by combing, and then rinsed and dried using a dryer.

The Method for Hair Treating with Hair Colorings

No. 1 agent and No. 2 agent of the hair coloring (Example 24–27) was mixed (the wt. % ratio of No. 1 agents to No. 2 agents was 1:1). This mixture was applied to hair and left for 30 minutes at room temperature. Then, the hair was rinsed and dried using a dryer.

The Method for Hair Treating with Waving Agents

No. 1 agent of the waving agent (Example 28, or the new waving agents prepared in Example 38 and 41) was applied to hair and spread by combing, and the hair was wound to a rod and left for 7 minutes at room temperature. Then No. 2 agent was applied by an applicator and left for 7 minutes. After the rod was removed, the hair was rinsed and dried using a dryer.

The Method for Hair Treating with Finishing Agents

The finishing agent (Example 29–37) was applied to hair and spread.

The Method for Hair Treating with Refreshers

The refresher (Example 40) was applied to the hair that had been dyed with acidic hair coloring materials. After the hair was left at 45° C. for 15 minutes, the hair was rinsed and dried using a dryer.

As clearly understood from the results of the above-mentioned Examples, the compositions for blending in hair treating agents of the present embodiment are prepared by selecting and combining adequately the ingredients which are cheap and easy to purchase so as to display an excellent hair treating effect. Therefore, the compositions for blending in hair treating agents of the present invention can be produced by lower cost and easily.

Since the hair treating agents of the present embodiment are prepared using above-mentioned compositions for blending in hair treating agents of the present invention, the cost for production are low, further, have excellent feels when used such as moist feel, rustle feeling, wet feel, luster, smooth feel, soft feel, suppleness, bounce, smoothness, less damage, no hardness and no squeak, feel, smooth combing, and have excellent functionalities such as easy appliance, well spread of hair treating agents, thickening ability and gelling ability of hair colorings, decolorizing ability of decolorizing agents, setting ability of finishing agents and dispersibility and dissolving ability to aromatic materials and azulenes etc. Further, in the preparation process of hair treating agentsince it is possible by using the compositions for blending in a hair treating agents of the present invention to blend various kinds of ingredients comprising alcohols etc. at a time, the production process may be remarkably simplified.

Example of the Second Embodiment

The second embodiment of the present invention is illustrated more concretely according to the following Examples.

(Preparation of the Compositions for Blending in Hair Treating Agents)

Examples 44

After each ingredient 43, 1, 57 and 12 was dispersed in ingredient 59 at room temperature, each ingredient 21, 47

TABLE 8

| feel when used | hair treating agent (Example) | | | | | | | | | | | | | | | | | | |
|---|---|---|---|---|---|---|---|---|---|---|---|---|---|---|---|---|---|---|---|
| and functionality | 23 | 24 | 25 | 26 | 27 | 28 | 29 | 30 | 31 | 32 | 33 | 34 | 35 | 36 | 37 | 38 | 39 | 40 | 41 |
| moist feel | ◎ | Δ | Δ | Δ | Δ | ◎ | ◎ | ◎ | Δ | Δ | Δ | Δ | Δ | Δ | Δ | ◎ | — | ◎ | — |
| rustle feeling | ○ | ○ | ○ | ○ | ○ | Δ | Δ | Δ | ◎ | ◎ | ◎ | ◎ | ◎ | ◎ | ◎ | ◎ | — | Δ | — |
| wet feel | Δ | Δ | Δ | Δ | Δ | Δ | Δ | Δ | Δ | Δ | Δ | ◎ | ◎ | Δ | Δ | ○ | — | Δ | — |
| luster | Δ | — | — | — | — | Δ | Δ | Δ | ○ | ◎ | ◎ | ◎ | ◎ | ○ | ◎ | Δ | — | Δ | — |
| smooth feel | Δ | ○ | ○ | ○ | ○ | Δ | ○ | ○ | — | ◎ | ◎ | ◎ | ◎ | ◎ | ◎ | Δ | — | Δ | — |
| soft feel | Δ | Δ | Δ | Δ | Δ | Δ | ○ | ○ | — | Δ | Δ | Δ | Δ | ◎ | Δ | ◎ | — | ○ | — |
| suppleness | ○ | ○ | ○ | ○ | ○ | ○ | ○ | ○ | — | ○ | ○ | Δ | Δ | ◎ | Δ | ○ | — | ◎ | — |
| bounce | ◎ | — | — | — | — | Δ | ◎ | ◎ | ◎ | Δ | Δ | Δ | Δ | ◎ | Δ | Δ | — | Δ | — |
| smoothness | ○ | Δ | Δ | Δ | Δ | ◎ | ◎ | ◎ | Δ | Δ | Δ | Δ | Δ | Δ | Δ | Δ | — | Δ | — |
| less damage | ◎ | Δ | Δ | Δ | Δ | ○ | ◎ | ◎ | Δ | ◎ | ◎ | ◎ | ◎ | ◎ | ◎ | ◎ | — | Δ | — |
| no hardness and no squeak | — | — | — | — | — | — | — | — | ◎ | — | — | — | — | — | — | — | — | Δ | — |
| improved feel | ○ | Δ | Δ | Δ | Δ | ○ | ○ | ○ | — | ○ | ○ | ○ | ○ | ○ | ○ | ◎ | — | — | — |
| smooth combing | ○ | Δ | Δ | Δ | Δ | ○ | ◎ | ◎ | ○ | ◎ | ◎ | ◎ | ◎ | ◎ | ◎ | — | — | ○ | — |
| easy appliance | — | ◎ | ◎ | ◎ | ◎ | — | — | — | — | ◎ | ◎ | ◎ | ◎ | ◎ | ◎ | — | — | ○ | — |
| thickning ability and gelling ability of hair colorings | — | ◎ | ◎ | ◎ | ◎ | — | — | — | — | — | — | — | — | — | — | — | — | — | ◎ |
| decolorizing ability of decolorizing agents | — | — | — | ◎ | ◎ | — | — | — | — | — | — | — | — | — | — | — | — | — | — |
| dyeing ability | — | Δ | Δ | Δ | Δ | — | — | — | — | — | — | — | — | — | — | — | — | — | — |
| well spread of finishing agent | — | — | — | — | — | — | — | — | — | ◎ | ◎ | ◎ | ◎ | ◎ | ◎ | — | — | — | — |
| setting ability | — | — | — | — | — | — | — | — | ◎ | ○ | ○ | ◎ | ◎ | ◎ | ◎ | — | — | — | — |
| removability of dye | — | — | — | — | — | — | — | — | — | — | — | — | — | — | — | — | — | ◎ | — |
| dispersibility and dissolving ability to aromatic materials and azulenes | — | — | — | — | — | — | — | — | — | — | — | — | — | — | — | — | ◎ | — | — |

In Table 8,
◎ indicates "Very good",
○ indicates "good" and
Δ indicates "normal".

and 54 was added in order. On adding each ingredient, the following ingredient was added after it was confirmed that the previously added ingredients had been dissoluved homogeneously. Thus, the composition for blending in hair treating agent of the present invention was prepared. The numbers indicating each ingredient, the ingredients and contents (kg) are shown in Table 9 and 10.

Examples 45

Each ingredient 4, 13, 59, 25 and 22 was added in order at the temperature shown in Table 9. On adding each ingredient, the following ingredient was added after it was confirmed that the previously added ingredients had been dissoluved homogeneously. Thus, the composition for blending in hair treating agent of the present invention was prepared. The numbers indicating each ingredient, the ingredients and contents (kg) are shown in Table 9 and 10.

Examples 46

Each ingredient 4, 13, 59, 25, 22 and 3 was added in order to prepare the composition for blending in hair treating agent of the present invention in the same manner as Example 45.

Examples 47

Each ingredient 4, 3, 13, 59 and 23 was added in order to prepare the composition for blending in hair treating agent of the present invention by the same preparation method as Example 45.

Examples 48

Each ingredient 4, 13, and 59 was added in order to prepare the composition for blending in hair treating agents of the present invention by the same preparation method as Example 45.

Examples 49

Each ingredient 4, 23, 26, 15, 59, 29 and 32 was added in order to prepare the composition for blending in hair treating agents of the present invention by the same preparation method as Example 45.

Examples 50

Each ingredient 4, 23, 29, 15 and 59 was added in order to prepare the composition for blending in hair treating agents of the present invention by the same preparation method as Example 45.

Examples 51

Each ingredient 4, 3, 33, 32, 25, 23, 22, 35, 40, 13 and 59 was added in order to prepare the composition for blending in hair treating agents of the present invention by the same preparation method as Example 45.

Examples 52

Each ingredient 4, 3, 33, 32, 25, 23, 22, 35, 37, 39, 16 and 59 was added in order to prepare the composition for blending in hair treating agents of the present invention by the same preparation method as Example 45.

Examples 53

Each ingredient 4, 5, 13, 59, 25 and 22 was added in order to prepare the composition for blending in hair treating agents of the present invention by the same preparation method as Example 45.

Examples 54

Each ingredient 8, 4, 13, 14, 25, 22, 3, 38 and 6 was added in order to prepare the composition for blending in hair treating agents of the present invention by the same preparation method as Example 45.

Examples 55

Each ingredient 5, 4, 7, 13, 59, 25, 44, 22 and 3 was added in order to prepare the composition for blending in hair treating agents of the present invention by the same preparation method as Example 45.

Examples 56

Each ingredient 34, 4, 3, 13, 23 and 10 was added in order to prepare the composition for blending in hair treating agents of the present invention by the same preparation method as Example 45.

Examples 57

Each ingredient 8, 3, 41, 16, 59, 23, 25 and 24 was added in order to prepare the composition for blending in hair treating agents of the present invention by the same preparation method as Example 45.

Examples 58

After ingredient 59 was heated to 80° C., ingredient 22 and 29 were added to this, and then dissolved homogeneously as stirring. Next, ingredient 17 and 50 were added, and then mixed homogeneously. After cooled to 45° C. as stirring, ingredient 52 and 49 were added in order, and then mixed homogeneously to prepare the composition for blending in hair treating agent of the present invention.

Examples 59

Each ingredient 25, 57, 12 and 55 was heated to the temperature shown in Table 13 to prepare homogeneously dissolved material. On the other hand, ingredient 53 and 59 (45.9 kg) were heated to the temperature shown in Table 13 to prepare aqueous solution. Next, the homogeneously dissoluved heated material was added as stirring to the above-mentioned heated aqueous solution, and then mixed and cooled below 45° C.

To this cooled mixture, each ingredient 36, 51 and 19 was added in order while confirming the dissolution. Finally, water (add water) was further added so as to adjust the total weight to be 100 kg, and mixed homogeneously. Thus, the composition for blending in hair treating agent of the present invention was prepared. The numbers indicating each ingredient, the ingredients and contents (kg) are shown in Table 13 and 14.

Example 60

Ingredient 59 (48.78 kg) and 42 were mixed as stirring at 40–50° C. to prepare the homogeneous mixture I.

Ingredient 53, 20 and 59 (2.4 kg) were mixed as stirring at 85° C. to prepare the homogeneous mixture II.

Ingredient 11, 27, 56, 57 and 59 (3.66 kg) were mixed as stirring at 85° C. to prepare the homogeneous mixture III.

The above-mentioned homogeneous mixture II and III were added in order to the afore-mentioned homogeneous mixture I, and dissoluved as stirring. On adding each mixture II and II, the following mixture was added after it was confirmed that the previously added mixture had been dissoluved homogeneously. Finally, water (add water) was further added so as to adjust the total weight to be 100 kg, and mixed homogeneously. Thus, the composition for blending in hair treating agent of the present invention was prepared. The numbers indicating each ingredient, the ingredients and contents (kg) are shown in Table 13 and 14.

Examples 61

Each ingredient 4, 23, 13 and 59 (0.22 kg) was heated to the temperature shown in Table 13 to prepare homogeneously dissolved material. On the other hand, ingredient 59 (88.58 L) was heated to the temperature shown in Table 13. Next, the heated homogeneous dissoluved material was added as stirring to the above-mentioned heated water, and then mixed, emulsified and cooled below 48–49° C.

To this cooled mixture, each ingredient 56 and 57 was added in order while confirming the dissolution. Finally, water (add water) was further added so as to adjust the total weight to be 100 kg, and mixed homogeneously. Thus, the composition for blending in hair treating agent of the present invention was prepared. The numbers indicating each ingredient, the ingredients and contents (kg) are shown in Table 13 and 14.

Examples 62

After ingredient 29 was heated to the temperature shown in Table 13, and then dissolved homogeneously, ingredient 58 (13.33 kg) was added gradually to prepare dissolved material. After homogeneous mixture of ingredient 1, 9 and 58 was added to the dissolved material, ingredient 48 and 59 were added, and finally ingredient 19 was added, and mixed homogeneously. Thus, the composition for blending in hair treating agents of the present invention was prepared. The numbers indicating each ingredient, the ingredients and contents (kg) are shown in Table 13 and 14.

Examples 63

Each ingredient 59, 48, 19, 46, 9 and 58 was added in order to prepare the composition for blending in hair treating agents of the present invention in the same manner as Example 45.

Examples 64

After each ingredient 43, 1, 12 and 59 (59.43 kg) was mixed homogeneously as stirring at room temperature, ingredient 21 and 59 (5.14 kg) were added. Next, this mixture was mixed as stirring at room temperature and under 400 mmHg. And then, ingredient 47 and 59 (2.86 kg) were added, and then mixed as stirring under 400 mmHg. Thus, the composition for blending in hair treating agent of the present invention was prepared. The numbers indicating each ingredient, the ingredients and contents (kg) are shown in Table 13 and 14.

Example 65

Ingredient 59, 19 and 48 were mixed as stirring at room temperature to prepare the homogeneous mixture I.

Ingredient 9, 1 and 58 were mixed as stirring at room temperature to prepare the homogeneous mixture II.

The above-mentioned homogeneous mixture II was added to the afore-mentioned homogeneous mixture I, and then mixed homogeneously as stirring. Next, ingredient 45 was added, and then stirred under 500 mmHg and at room temperature, and then mixed homogeneously. Thus, the composition for blending in hair treating agent of the present invention was prepared. The numbers indicating each ingredient, the ingredients and contents (kg) are shown in Table 15 and 16.

Example 66

To ingredient 59 (47.62 kg), each ingredient 19, 57, 2, 11 and 45 was added in order while confirming the dissolution. After this mixture was stirred under 500 mmHg, ingredient 59 (10.95 kg) and 12 were added. Finally, water (add water) was further added so as to adjust the total weight to be 100 kg, and mixed homogeneously. Thus, the composition for blending in hair treating agent of the present invention was prepared. The numbers indicating each ingredient, the ingredients and contents (kg) are shown in Table 15 and 16.

Example 67

Dissolved mixture of ingredient 43 and 12, dissolved mixture of ingredient 1 and 57, ingredient 59 (73 kg), dissolved mixture of ingredient 21 and 59 (4.045 kg), dissolved mixture of ingredient 47 and 59 (3.05 kg) and dissolved mixture of ingredient 54 and 59 (1.48 kg) were added in order while confirming the dissolution. Thus, the composition for blending in hair treating agent of the present invention was prepared. The numbers indicating each ingredient, the ingredients and contents (kg) are shown in Table 15 and 16.

Example 68

All ingredients were mixed as stirring. Thus, the composition for blending in hair treating agent of the present invention was prepared. The numbers indicating each ingredient, the ingredients and contents (kg) are shown in Table 15 and 16.

TABLE 9

| | Example | | | | | | |
|---|---|---|---|---|---|---|---|
| | 44 | 45 | 46 | 47 | 48 | 49 | 50 |
| heating temperature (° C.) | — | 70 | 70 | 70 | 70 | 75 | 70~75 |
| ingredient (kg) | | | | | | | |
| 1 ethanol | 10 | — | — | — | — | — | — |
| 2 isopropanol | — | — | — | — | — | — | — |
| 3 lauryl alcohol | — | — | 8 | 7 | — | — | — |
| 4 cetanol | — | 69 | 63.3 | 48.5 | 53.3 | 1 | 5 |
| 5 stearyl alcohol | — | — | — | — | — | — | — |
| 6 oleyl alcohol | — | — | — | — | — | — | — |
| 7 behenyl alcohol | — | — | — | — | — | — | — |
| 8 cetostearyl alcohol | — | — | — | — | — | — | — |
| 9 benzyl alcohol | — | — | — | — | — | — | — |
| 10 propylene glycol | — | — | — | — | — | — | — |
| 11 1,3-butylene glycol | — | — | — | — | — | — | — |
| 12 concentrated glycerin | 2 | — | — | — | — | — | — |
| 13 sodium lauryl sulfate | — | 6 | 6 | 5.5 | 5.5 | — | — |
| 14 triethanolamine lauryl sulfate | — | — | — | — | — | — | — |
| 15 sodium cetyl sulfate | — | — | — | — | — | 3.2 | 7 |
| 16 sodium N-myristoyl methyl taurate | — | — | — | — | — | — | — |
| 17 triethanolamine polyoxyethylene lauryl ether sulfate | — | — | — | — | — | — | — |
| 18 polyoxethylene oleylether phosphate | — | — | — | — | — | — | — |
| 19 phosphoric acid | — | — | — | — | — | — | — |
| 20 dibasic sodium phosphate | — | — | — | — | — | — | — |
| 21 sodium hydroxide | 0.3 | — | — | — | — | — | — |

TABLE 10

| | Example | | | | | | |
|---|---|---|---|---|---|---|---|
| | 44 | 45 | 46 | 47 | 48 | 49 | 50 |
| ingredient (kg) | | | | | | | |
| 22 polyoxyethylene lauryl ether[1)] | — | 10 | 9 | — | — | — | — |
| 23 polyoxyethylene cetyl ether | — | — | — | 34.5[2)] | 36.5[3)] | 76.2[4)] | 52.3[5)] |
| 24 polyoxyethylene stearyl ether | — | — | — | — | — | — | — |
| 25 polyoxyethylene oleyl ether | — | 15[6)] | 13[7)] | — | — | — | — |
| 26 polyoxyethylene nonylphenyl ether | — | — | — | — | — | 1[8)] | — |
| 27 polyoxyethylene castor oil | — | — | — | — | — | — | — |
| 28 polyoxyethylene hydrogenated castor oil | — | — | — | — | — | — | — |
| 29 polyoxyethylene lanolin | — | — | — | — | — | 10[9)] | 31[10)] |
| 30 polyoxyethylene cocoalkyl amine | — | — | — | — | — | — | — |
| 31 polyoxyethylene · polyoxy-propylene cetyl ether | — | — | — | — | — | — | — |
| 32 polyoxyethylene · polyoxy-propylene lanolin | — | — | — | — | — | 5[11)] | — |
| 33 oleic acid diethanolamide | — | — | — | — | — | — | — |
| 34 stearic acid diethanolamide | — | — | — | — | — | — | — |
| 35 polyoxyethylene sorbitol tetraoleate | — | — | — | — | — | — | — |
| 36 cocodimethyl amine oxide | — | — | — | — | — | — | — |
| 37 meadowfoam oil | — | — | — | — | — | — | — |
| 38 olive oil | — | — | — | — | — | — | — |
| 39 shea butter | — | — | — | — | — | — | — |
| 40 mink wax | — | — | — | — | — | — | — |
| 41 liquid petrolatum | — | — | — | — | — | — | — |
| 42 dimethyl diallyl ammonium chloride · acrylamide copolymer | — | — | — | — | — | — | — |
| 43 hydroxyethyl cellulose | 2.6 | — | — | — | — | — | — |
| 44 polypropylene glycol | — | — | — | — | — | — | — |
| 45 carboxyvinylpolymer | — | — | — | — | — | — | — |
| 46 polyoxypropylene methylglucoside ether | — | — | — | — | — | — | — |
| 47 glycolic acid | 0.7 | — | — | — | — | — | — |
| 48 tartaric acid | — | — | — | — | — | — | — |
| 49 triethanolamine | — | — | — | — | — | — | — |
| 50 2-alkyl N-carboxymethyl N-hydroxyethyl imidazolinium betaine | — | — | — | — | — | — | — |
| 51 cocoyl amide propyldimethyl glycine | — | — | — | — | — | — | — |
| 52 1-hydroxyethane-1, 1-diphosphonic acid | — | — | — | — | — | — | — |
| 53 disodium edetate | — | — | — | — | — | — | — |
| 54 hydrolysed animal protein | 5 | — | — | — | — | — | — |
| 55 orange oil | — | — | — | — | — | — | — |
| 56 (iso)propyl parahydroxybenzoate | — | — | — | — | — | — | — |
| 57 methyl parahydroxybenzoate | 0.1 | — | — | — | — | — | — |
| 58 N-methyl-2-pyrrolidone. | — | — | — | — | — | — | — |
| 59 water | 79.4 | — | 0.7 | 4.5 | 4.7 | 1.8 | 4.7 |

[1)–11)] in Table 10 indicate,
[1)]23EO,
[2)]5.87 kg (30EO) + 28.63 kg (40EO),
[3)]5.76 kg (30EO) + 28.74 kg (40EO),
[4)]2.74 kg (2EO) + 72.29 kg (5EO) + 1.17 kg (20EO),
[5)]8.72 kg (2EO) + 42.21 kg (6EO) + 2.29 kg,
[6)]50EO,
[7)]50EO,
[8)]8EO,
[9)]20EO,
[10)]20EO,
[11)]50EO, 12PO.

TABLE 11

| | Example | | | | | | |
|---|---|---|---|---|---|---|---|
| | 51 | 52 | 53 | 54 | 55 | 56 | 57 |
| heating temperature (° C.) | 75 | 75 | 70 | 70 | 70 | 75 | 70 |
| ingredient (kg) | | | | | | | |
| 1 ethanol | — | — | — | — | — | — | — |
| 2 isopropanol | — | — | — | — | — | — | — |
| 3 lauryl alcohol | 5 | 5 | — | 3 | 3 | 1.5 | 3 |
| 4 cetanol | 24 | 25 | 58.4 | 30 | 55.7 | 15 | — |
| 5 stearyl alcohol | — | — | 26 | — | 15 | — | — |
| 6 oleyl alcohol | — | — | — | 1 | — | — | — |
| 7 behenyl alcohol | — | — | — | — | 5 | — | — |
| 8 cetostearyl alcohol | — | — | — | 40 | — | — | 39 |
| 9 benzyl alcohol | — | — | — | — | — | — | — |
| 10 propylene glycol | — | — | — | — | — | 36.7 | — |
| 11 1,3-butylene glycol | — | — | — | — | — | — | — |
| 12 concentrated glycerin | — | — | — | — | — | — | — |
| 13 sodium lauryl sulfate | 13[1)] | — | 3 | 7 | 3 | 1.5 | — |
| 14 triethanolamine lauryl sulfate | — | — | — | 4[2)] | — | — | — |
| 15 sodium cetyl sulfate | — | — | — | — | — | — | — |
| 16 sodium N-myristoyl methyl taurate | — | 11 | — | — | — | — | 3 |
| 17 triethanolamine polyoxyethylene lauryl ether sulfate | — | — | — | — | — | — | — |
| 18 polyoxethylene oleylether phosphate | — | — | — | — | — | — | — |
| 19 phosphoric acid | — | — | — | — | — | — | — |
| 20 dibasic sodium phosphate | — | — | — | — | — | — | — |
| 21 sodium hydroxide | — | — | 0.6 | — | 0.3 | 1.3 | — |

[1)] and [2)] in Table 11 indicate,
[1)]Content, 43 wt %,
[2)]Content, 40 wt %.

TABLE 12

| | Example | | | | | | |
|---|---|---|---|---|---|---|---|
| | 51 | 52 | 53 | 54 | 55 | 56 | 57 |
| ingredient (kg) | | | | | | | |
| 22 polyoxyethylene lauryl ether[1)] | 7 | 7 | 5 | 6 | 5 | — | — |
| 23 polyoxyethylene cetyl ether | 7[2)] | 7[2)] | — | — | — | 14[3)] | 30[4)] |
| 24 polyoxyethylene stearyl ether | — | — | — | — | — | — | 5[5)] |
| 25 polyoxyethylene oleyl ether[6)] | 10 | 10 | 7 | 8 | 7 | — | 5 |
| 26 polyoxyethylene nonylphenyl ether | — | — | — | — | — | — | — |
| 27 polyoxyethylene castor oil | — | — | — | — | — | — | — |
| 28 polyoxyethylene hydrogenated castor oil | — | — | — | — | — | — | — |
| 29 polyoxyethylene lanolin | — | — | — | — | — | — | — |
| 30 polyoxyethylene cocoalkyl amine | — | — | — | — | — | — | — |
| 31 polyoxyethylene · polyoxypropylene cetyl ether | — | — | — | — | — | — | — |
| 32 polyoxyethylene · polyoxpropylene lanolin[7)] | 7 | 7 | — | — | — | — | — |
| 33 oleic acid diethanolamide | 14 | 14 | — | — | — | — | — |
| 34 stearic acid diethanolamide | — | — | — | — | — | 30 | — |
| 35 polyoxyethylene sorbitol tetraoleate[8] | 1.5 | 1 | — | — | — | — | — |
| 36 cocodimethyl amine oxide | — | — | — | — | — | — | — |
| 37 meadowfoam oil | — | 1.5 | — | — | — | — | — |
| 38 oliveoil | — | — | — | 1 | — | — | — |
| 39 shea butter | — | 1.5 | — | — | — | — | — |
| 40 mink wax | 1.5 | — | — | — | — | — | — |
| 41 liquid petrolatum | — | — | — | — | — | — | 9 |
| 42 dimethyl diallyl ammonium chloride · acrylamide copolymer | — | — | — | — | — | — | — |
| 43 hydroxyethyl cellulose | — | — | — | — | — | — | — |
| 44 polypropylene glycol | — | — | — | — | 6 | — | — |

TABLE 12-continued

| | Example | | | | | | |
|---|---|---|---|---|---|---|---|
| | 51 | 52 | 53 | 54 | 55 | 56 | 57 |
| 45 carboxyvinylpolymer | — | — | — | — | — | — | — |
| 46 polyoxypropylene methylglucoside ether | — | — | — | — | — | — | — |
| 47 glycolic acid | — | — | — | — | — | — | — |
| 48 tartaric acid | — | — | — | — | — | — | — |
| 49 triethanolamine | — | — | — | — | — | — | — |
| 50 2-alkyl N-carboxymethyl N-hydxoxyethyl imidazolinium betaine | — | — | — | — | — | — | — |
| 51 cocyl amide propyldimethyl glycine | — | — | — | — | — | — | — |
| 52 1-hydroxyethane-1, 1-diphosphonic acid | — | — | — | — | — | — | — |
| 53 disodium edetate | — | — | — | — | — | — | — |
| 54 hydrolysed animal protein | — | — | — | — | — | — | — |
| 55 orange oil | — | — | — | — | — | — | — |
| 56 (iso)propyl parahydroxybenzoate | — | — | — | — | — | — | — |
| 57 methyl parahydroxybenzoate | — | — | — | — | — | — | — |
| 58 N-methyl-2-pyrrolidone | — | — | — | — | — | — | — |
| 59 water | 10 | 10 | — | — | — | — | 6 |

[1)–8)] in Table 12 indicate,
[1)]3EO,
[2)]6EO,
[3)]1.55 kg (30EO) + 12.45 kg (40EO),
[4)]20.91 kg (20EO) + 9.09 kg (40EO),
[5)]6EO,
[6)]50EO,
[7)]50EO, 12PO,
[8)]60EO.

TABLE 13

| | Example | | | | | | |
|---|---|---|---|---|---|---|---|
| | 58 | 59 | 60 | 61 | 62 | 63 | 64 |
| heating temperature (° C.) | 80 | 65~70 | 50 | 83~85 | 70 | — | — |
| ingredient (kg) | | | | | | | |
| 1 ethanol | — | — | — | — | 26 | — | 20 |
| 2 isopropanol | 3 | — | — | — | — | — | — |
| 3 lauryl alcohol | — | — | — | — | — | — | — |
| 4 cetanol | — | — | — | 2.9 | — | — | — |
| 5 stearyl alcohol | — | — | — | — | — | — | — |
| 6 oleyl alcohol | — | — | — | — | — | — | — |
| 7 behenyl alcohol | — | — | — | — | — | — | — |
| 8 cetostearyl alcohol | — | — | — | — | — | — | — |
| 9 benzyl alcohol | — | — | — | — | 17 | 20 | — |
| 10 propylene glycol | — | — | — | — | — | — | — |
| 11 1,3-butylene glyccol | — | — | 3 | — | — | — | — |
| 12 concentrated glycerin | — | 2 | — | — | — | — | 4 |
| 13 sodium lauryl sulfate | — | — | — | 0.3 | — | — | — |
| 14 triethanolamine lauryl sulfate | — | — | — | — | — | — | — |
| 15 sodium cetyl sulfate | — | — | — | — | — | — | — |
| 16 sodium N-myristoyl methyl taurate | — | — | — | — | — | — | — |
| 17 triethanolamine polyoxyethylene lauryl ether sulfate | 54[1)] | — | — | — | — | — | — |
| 18 polyoxethylene oleylether phosphate | — | — | — | — | — | — | — |
| 19 phosphoric acid[2)] | — | 0.2 | — | — | 6.5 | 8 | — |
| 20 dibasic sodium phosphate | — | — | 0.2 | — | — | — | — |
| 21 sodium hydroxide | — | — | — | — | — | — | 0.6 |

[1)] and [2)] in Table 13 indicate,
[1)]3EO, Content 43 wt %,
[2)]Content 85 wt %.

TABLE 14

| ingredient (kg) | Example 58 | 59 | 60 | 61 | 62 | 63 | 64 |
|---|---|---|---|---|---|---|---|
| 22 polyoxyethylene lauryl ether | 1[1] | — | — | — | — | — | — |
| 23 polyoxyethylene cetyl ether | — | — | — | 1.6[2] | — | — | — |
| 24 polyoxyethylene stearyl ether | — | — | — | — | — | — | — |
| 25 polyoxyethylene oleyl ether | — | 5[3] | — | — | — | — | — |
| 26 polyoxyethylene nonylphenyl ether | — | — | — | — | — | — | — |
| 27 polyoxyethylene castor oil | — | — | 1[4] | — | — | — | — |
| 28 polyoxyethylene hydrogenated castor oil | — | — | — | — | — | — | — |
| 29 polyoxyethylene lanolin | 1[5] | — | — | — | 7 | — | — |
| 30 polyoxyethylene cocoalkyl amine | — | — | — | — | — | — | — |
| 31 polyoxyethylene · polyoxypropylene cetyl ether | — | — | — | — | — | — | — |
| 32 polyoxyethylene · polyoxpropylene lanolin | — | — | — | — | — | — | — |
| 33 oleic acid diethanolamide | — | — | — | — | — | — | — |
| 34 stearic acid diethanolamide | — | — | — | — | — | — | — |
| 35 polyoxyethylene sorbitol tetraoleate | — | — | — | — | — | — | — |
| 36 cocodimethyl amine oxide | — | 20[6] | — | — | — | — | — |
| 37 meadowfoam oil | — | — | — | — | — | — | — |
| 38 olive oil | — | — | — | — | — | — | — |
| 39 shea butter | — | — | — | — | — | — | — |
| 40 mink wax | — | — | — | — | — | — | — |
| 41 liquid petrolatum | — | — | — | — | — | — | — |
| 42 dimethyl diallyl ammonium chloride · acrylamide copolymer | — | — | 35 | — | — | — | — |
| 43 hydroxyethyl cellulose | — | — | — | — | — | — | 5 |
| 44 polypropylene glycol | — | — | — | — | — | — | — |
| 45 carboxyvinylpolymer | — | — | — | — | — | — | — |
| 46 polyoxypropylene methylglucoside ether | — | — | — | — | — | 20 | — |
| 47 glycolic acid | — | — | — | — | — | — | 2[7] |
| 48 tartaric acid | — | — | — | — | 6.5 | 8 | — |
| 49 triethanolamine | 2.1 | — | — | — | — | — | — |
| 50 2-alkyl N-carboxymethyl N-hydroxyethyl imidazolinium betaine | 15[8] | — | — | — | — | — | — |
| 51 cocoyl amide propyldimethyl glycine | — | 20[9] | — | — | — | — | — |
| 52 1-hydroxyethane-1, 1-diphosphonic acid | 2[11] | — | — | — | — | — | — |
| 53 disodium edetate | — | 0.1 | 0.1 | — | — | — | — |
| 54 hydrolysed animal protein | — | — | — | — | — | — | — |
| 55 orange oil | — | 3 | — | — | — | — | — |
| 56 (iso)propyl parahydroxybenzoate | — | — | 0.05[10] | 0.1 | — | — | — |
| 57 methyl parahydroxybenzoate | — | 0.1 | 0.1 | 0.1 | — | — | — |
| 58 N-methyl-2-pyrrolidone | — | — | — | — | 27 | 38 | — |
| 59 water | 21.9 | 49.6 | 60.55 | 95 | 10 | 6 | 68.4 |

[1]–[11] in Table 14 indicate,
[1]23EO,
[2]0.3 kg (30EO) + 1.3 kg (40EO),
[3]2.2 kg (10EO) + 2.8 kg (20EO),
[4]40EO,
[5]70EO,
[6]Content, 30 wt %.
[7]Content, 70 wt %.
[8]Content, 50 wt %.
[9]Content, 30 wt %.
[10]isopropyl parahydroxybenzoate
[11]Content, 60 wt %.

TABLE 15

| | Example | | | |
|---|---|---|---|---|
| | 65 | 66 | 67 | 68 |
| heating temperature (° C.) | — | — | — | 90 |
| ingredient (kg) | | | | |
| 1 ethanol | 19 | — | 10 | — |
| 2 isopropanol | — | 0.2 | — | — |
| 3 lauryl alcohol | — | — | — | — |
| 4 cetanol | — | — | — | — |
| 5 stearyl alcohol | — | — | — | — |
| 6 oleyl alcohol | — | — | — | — |
| 7 behenyl alcohol | — | — | — | — |
| 8 cetostearyl alcohol | — | — | — | — |
| 9 benzyl alcohol | 6 | — | — | — |
| 10 propylene glycol | — | — | — | 14.5 |
| 11 1,3-butylene glycol | — | 1 | — | — |
| 12 concentrated glycerin | — | 40 | 2 | 11.6 |
| 13 sodium lauryl sulfate | — | — | — | — |
| 14 triethanolamine lauryl sulfate | — | — | — | — |
| 15 sodium cetyl sulfate | — | — | — | — |
| 16 sodium N-myristoyl methyl taurate | — | — | — | — |
| 17 triethanolamine polyoxyethylene lauryl ether sulfate | — | — | — | — |
| 18 polyoxethylene oleylether phosphate | — | — | — | 12.1[2)] |
| 19 phosphoric acid[1)] | 2.5 | 0.2 | — | — |
| 20 dibasic sodium phosphate | — | — | — | — |
| 20 sodium hydroxide | — | — | 0.285 | — |

[1)] and [2)] in Table 15 indicate,
[1)]Content, 85 wt %,
[2)]3EO.

TABLE 16

| | Example | | | |
|---|---|---|---|---|
| | 65 | 66 | 67 | 68 |
| ingredient (kg) | | | | |
| 22 polyoxyethylene lauryl ether | — | — | — | — |
| 23 polyoxyethylene cetyl ether | — | — | — | — |
| 24 polyoxyethylene stearyl ether | — | — | — | — |
| 25 polyoxyethylene oleyl ether | — | — | — | — |
| 26 polyoxyethylene nonylphenyl ether | — | — | — | — |
| 27 polyoxyethylene castor oil | — | — | — | — |
| 28 polyoxyethylene hydrogenated castor oil | — | — | — | 36.2[1)] |
| 29 polyoxyethylene lanolin | — | — | — | — |
| 30 polyoxyethylene cocoalkyl amine | — | — | — | 1.2[2)] |
| 31 polyoxyethylene · polyoxypropylene cetyl ether | — | — | — | 24.1[3)] |
| 32 polyoxyethylene · polyoxpropylene lanolin | — | — | — | — |
| 33 oleic acid diethanolamide | — | — | — | — |
| 34 stearic acid diethanolamide | — | — | — | — |
| 35 polyoxyethylene sorbitol tetraoleate | — | — | — | — |
| 36 cocodimethyl amine oxide | — | — | — | — |
| 37 meadowfoam oil | — | — | — | — |
| 38 olive oil | — | — | — | — |
| 39 shea butter | — | — | — | — |
| 40 mink wax | — | — | — | — |
| 41 liquid petrolatum | — | — | — | — |
| 42 dimethyl diallyl ammonium chloride · acrylamide copolymer | — | — | — | — |
| 43 hydroxyethyl cellulose | — | — | 2.57 | — |
| 44 polypropylene glycol | — | — | — | — |
| 45 carboxyvinylpolymer | 5 | 1.5 | — | — |
| 46 polyoxypropylene methylglucoside ether | — | — | — | — |
| 47 glycolic acid | — | — | 1[4)] | — |
| 48 tartaric acid | 2.5 | — | — | — |
| 49 triethanolamine | — | — | — | — |
| 50 2-alkyl N-carboxymethyl N-hydroxyethyl imidazolinium betaine | — | — | — | — |

TABLE 16-continued

| | Example | | | |
|---|---|---|---|---|
| | 65 | 66 | 67 | 68 |
| 51 cocoyl amide propyldimethyl glycine | — | — | — | — |
| 52 1-hydroxyethane-1,1-diphosphonic acid | — | — | — | — |
| 53 disodium edetate | — | — | — | — |
| 54 hydrolysed animal protein | — | — | 5 | — |
| 55 orange oil | — | — | — | — |
| 56 (iso)propyl parahydroxybenzoate | — | — | — | 0.1 |
| 57 methyl parahydroxybenzoate | — | 0.02 | 0.1 | 0.2 |
| 58 N-methyl-2-pyrrolidone | 25 | — | — | — |
| 59 water | 40 | 57.08 | 79.045 | — |

[1)-4)] in Table 16 indicate,
[1)]40EO,
[2)]4EO,
[3)]20EO, 4 PO,
[4)]Content, 70 wt. %.

(Preparation of 2-Bath Type of Treatments.)

Examples 69

Preparation of Liquid 1 of 2-Bath Type of Treatment 30 kg of the composition for blending in hair conditioner (Example 67) and 58.85 kg of water were mixed homogeneously to prepare composition I.

Further, 7 kg of 1,3-butylene glycol, 4 kg of ethanol and 0.15 kg of parabens were mixed homogeneously to prepare composition II.

The above-mentioned composition II was added to the above-mentioned composition I, and mixed homogeneously. Thus, the Liquid 1 of 2-bath type of treatment of the present invention was prepared.

Preparation of Liquid 2 of 2-Bath Type of Treatment 9.5 kg of behenyl alcohol, 2.8 kg of 60 wt. % stearyl trimethyl ammonium chloride, 0.2 kg of polyoxyethylene (20 EO) sorbitan monooleate, 2 kg of 1,3-butylene glycol and 0.15 kg of parabens were mixed homogeneously to prepare composition IV.

Lactic acid aqueous solution was prepared with 0.1 kg of 90% lactic acid and 4.9 kg of water.

Further, 3 kg of amino-modified silicone, 2.5 kg of highly polymerized methyl polysiloxane and 14.5 kg of methyl polysiloxane (20 cs) were mixed homogeneously to prepare composition V.

The above-mentioned composition IV and 90% lactic acid aqueous solution were heated to 80–85° C., mixed as stirring to prepare emulsion. After the emulsion was cooled to 45° C., the above-mentioned composition V was added. Finally, water (add water) was further added so as to adjust the total weight to be 100 kg, and mixed homogeneously. Thus, the Liquid 2 of 2-bath type of treatment of the present invention was prepared.

(Preparation of Acidic Hair Coloring Materials)

Example 70–78 and 80

The mixture of benzyl alcohol and ethanol were added to the composition for blending in hair coloring (Example 65) at room temperature, and mixed homogeneously. Next, glycolic acid and perfume, if necessary, were added. And then, dye aqueous solution, that had been prepared by dissoluving dyes (each A–I) in proper amount of water that had been heated above 80° C., was added, and mixed homogeneously. Finally, water (add water) was added so as to adjust the total weight to be 100 kg, and mixed homogeneously. Thus, the acidic hair coloring material of the present invention was prepared. The ingredients and contents (kg) of acidic hair coloring material are shown in Table 17 and 18. The formulation of the used dyes (each A–I.) is shown in Table 20 and 21.

Example 79

The acidic hair coloring material of the present invention was prepared in the same manner as Example 70–78 or 80 except that ethanol and benzyl alcohol were not used.

The ingredients and contents (kg) are shown in Table 18.

TABLE 17

| | Example | | | | | |
|---|---|---|---|---|---|---|
| ingredient(kg) | 70 | 71 | 72 | 73 | 74 | 75 |
| composition blended in hair coloring | Example 65 60 | Example 65 60 | Example 65 60 | Example 65 60 | Example 65 60 | Example 65 60 |
| ethanol | 10 | 10 | 10 | 10 | 10 | 10 |
| benzyl alcohol | 10 | 10 | 10 | 10 | 10 | 10 |
| dye | A | B | C | D | E | F |
| 70% glycolic acidaqueous solution | — | — | — | — | — | — |
| perfume | — | — | — | — | — | — |
| water | remaining volume | remaining volume | remaining volume | remaining volume | remaining volume | remaining volume |
| total amount | 100 | 100 | 100 | 100 | 100 | 100 |

TABLE 18

| | Example | | | | |
|---|---|---|---|---|---|
| ingredient(kg) | 76 | 77 | 78 | 79 | 80 |
| composition blended in hair coloring | Example 65 60 | Example 65 60 | Example 65 60 | Example 65 80 | Example 65 70 |
| ethanol | 10 | 10 | 10 | — | 5 |
| benzyl alcohol | 10 | 10 | 8 | — | 5 |
| dye | G | H | proper amount | proper amount | I |
| 70% glycolic acidaqueous solution | — | — | 2 | — | — |
| perfume | — | — | proper amount | proper amount | proper amount |
| water | remaining volume | remaining volume | remaining volume | remaining volume | remaining volume |
| total amount | 100 | 100 | 100 | 100 | 100 |

Example 81

Each ingredients II–V was added in order to the homogeneously dissoluved ingredients I. On adding each ingredient II–V, the following ingredient was added after it was confirmed that the previously added ingredient had been dissoluved homogeneously. Ingredient V was prepared by dissoluving dye J in water that had been heated above 80° C. Finally, water (add water) was further added so as to adjust the total weight to be 100 kg. Thus, the acidic hair coloring material of the present invention was prepared. The formulation of each ingredient I–V is shown in Table 19. The formulation of the used dye J is shown in Table 21.

Example 82

Each ingredient II–VI was added in order to the homogeneously dissoluved ingredients I. On adding each ingredient II–VI, the following ingredient was added after it was confirmed that the previously added ingredient had been dissoluved homogeneously. Ingredient VI was prepared by dissoluving dye K in water that had been heated above 80° C. Finally, water (add water) was further added so as to adjust the total weight to be 100 kg. Thus, the acidic hair coloring material of the present invention was prepared. The formulation of each ingredient I–VI is shown in Table 19. The formulation of the used dye K is shown in Table 21.

TABLE 19

| | | Example | |
|---|---|---|---|
| | ingredient (kg) | 81 | 82 |
| I | composition blended in hair coloring | — | Example 64 35 |
| | hydroxyethyl cellulose | 2 | — |
| | water | 40 | 10 |
| II | ethanol | 5 | — |
| | 25% sodium polyacrylate | — | 12 |
| III | composition blended in hair coloring | Example 62 30 | — |
| | glycerin | — | 2 |
| IV | 35% hydrochloric acid | 0.02 | — |
| | benzyl alcohol | — | 10 |

TABLE 19-continued

| | ingredient (kg) | Example 81 | Example 82 |
|---|---|---|---|
| V | ethanol | — | 10 |
| | dye | J | — |
| | water | 20 | — |
| VI | dye | — | K |
| | water | — | 20 |

TABLE 20

| ingredient(kg) | dye A | B | C | D | E | F |
|---|---|---|---|---|---|---|
| Red No. 2 | — | — | — | — | — | — |
| Orange No. 205 | 0.27 | 0.4 | 0.45 | 0.25 | — | 0.6 |
| Yellow No. 4 | — | — | — | 0.12 | 0.5 | — |
| Green No. 3 | — | — | — | — | — | — |
| Green No. 204 | — | — | — | — | 0.05 | 0.05 |
| Violet No. 401 | 0.17 | 0.15 | 0.25 | 0.1 | — | — |
| Black No. 401 | 0.2 | 0.15 | 0.05 | 0.05 | — | — |

TABLE 21

| ingredient(kg) | dye G | H | I | J | K |
|---|---|---|---|---|---|
| Red No. 2 | 0.1 | — | — | — | — |
| Orange No. 205 | — | — | 0.4 | 0.6 | 0.3 |
| Yellow No. 4 | — | — | — | — | — |
| Green No. 3 | — | 0.5 | — | — | — |
| Green No. 204 | — | 0.05 | — | — | — |
| Violet No. 401 | 0.4 | — | 0.1 | 0.3 | 0.1 |
| Black No. 401 | — | — | 0.1 | 0.24 | 0.1 |

(Preparation of Oxidizing Hair Coloring Agents.)

Example 83

Preparation of No. 1 Agent of Oxidizing Hair Coloring Agents

Proper amount of dye intermediates (Mixture of resorcinol, p-phenylene diamine, m-aminophenol and p-aminophenol.) and proper amount of antioxidant were added to 60 kg of the initial water, that had been heated to 80–85° C., and then prepared aqueous solution by stirring.

After 20 kg of the composition for blending in hair coloring (Example 56) was dissolved homogeneously at 80–85° C., this composition was added to the afore-mentioned heated aqueous solution, and then emulsified as stirring. After this emulsion was cooled to 45° C., proper amount of monoethanolamine and 0.17 kg of 60% hydroxyethane diphosphonic acid were added. Finally, purified water was added so as to adjust the total weight to be 100 kg. Thus No. 1 agent of oxidizing hair coloring agent was prepared.

Preparation of No. 2 Agent of Oxidizing Hair Coloring Agents

After 10 kg of the composition for blending in hair coloring (Example 56) was dissolved homogeneously at 80–85° C., this composition was added to the initial water, that had been heated to 80–85° C., and then emulsified as stirring. After this emulsion was cooled to 45° C. as stirring, 0.17 kg of 60% hydroxyethane diphosphonic acid, 0.26 kg of dibasic sodium phosphate (12 hydrate) and 16.9 kg of 35% hydrogen peroxide were added. Finally, water was added so as to adjust the total weight to be 100 kg. Thus No. 2 agent of oxidizing hair coloring agent was prepared.

(Preparation of Decolorizing Agents)

Example 84

Preparation of No. 1 Agents of Decolorizing Agents

Proper amount of antioxidant was added as stirring to 60 kg of the initial water, that had been heated to 80–85° C., to prepare aqueous solution. After 20 kg of the composition for blending in hair coloring (Example 56) was dissolved homogeneously at 80–85° C., this composition was added to the afore-mentioned aqueous solution, and then emulsified as stirring. After this emulsion was cooled to 45° C., proper amount of monoethanolamine and 0.17 kg of 60% hydroxyethane diphosphonic acid were added. Finally, water was added so as to adjust the total weight to be 100 kg. Thus No. 1 agent of decolorizing agent was prepared.

Preparation of No. 2 Agents of Decolorizing Agents

No. 2 agent of decolorizing agent was prepared in the same manner as Example 83.

(Preparation of Waving Agent)

Example 85–91

Preparation of Viscous Liquid (A–G.)

The composition for blending in waving agent (Example 45–47, 49, 51 or 52) was heated to the temperature shown in Table 22, and then homogeneously dissolved. Initial water (and, if necessary, sodium dehydroacetate.) was heated to the temperature shown in Table 22. The afore-mentioned heated homogeneously dissolved material was added as stirring to the heated initial water (or aqueous solution.), and then homogeneously mixed.

After this homogeneous mixture was cooled as stirring to the temperature shown in Table 22, water was added so as to adjust the total weight to be the amount shown in Table 22, and then mixed homogeneously. Thus, viscous liquids having various concentrations of the composition for blending in waving agent were prepared. The heating temperatures, the cooling temperatures, ingredients and the concentrations are shown in Table 22.

TABLE 22

| | viscous liquid A | B | C | D | E | F | G |
|---|---|---|---|---|---|---|---|
| heating temperature (° C.) | about 83~85 | about 83~85 | about 83~85 | about 83~85 | about 80~85 | about 83~85 | 80~85 |
| cooling temperature (° C.) | 46~48 | 46~48 | 46~48 | 46~48 | 42~46 | 47~49 | 47~49 |
| ingredient (kg) | | | | | | | |
| composition blended in waving agent | Example 45<br>25 | Example 46<br>30 | Example 46<br>25 | Example 47<br>25 | Example 49<br>25 | Example 51<br>15 | Example 52<br>15 |
| initial water | 450 | 450 | 450 | 450 | 450 | 80 | 80 |

TABLE 22-continued

| | viscous liquid | | | | | | |
|---|---|---|---|---|---|---|---|
| | A | B | C | D | E | F | G |
| sodium dehydroacetate | — | 0.5 | — | — | — | — | — |
| total amount | 500 | 500 | 500 | 500 | 500 | 100 | 100 |
| concentration of viscous liquid (wt. %) | 5 | 6 | 5 | 5 | 5 | 15 | 15 |

Preparation of No. 1 Agents of Waving Agents

50% ammonium thioglycolate (ATG) or cysteine, strong ammonia solution and, if necessary, monoethanolamine were added to the oviscous liquid btained above (each A–G) at room temperature. Further, water (add water) was added so as to adjust the total weight to be 100 kg, and then mixed homogeneously. Thus No. 1 agent of waving agent (Example 85–91) was prepared. The ingredients and contents (kg) are shown in Table 23.

TABLE 23

| No.1 agent of waving agent | Example | | | | | | |
|---|---|---|---|---|---|---|---|
| ingredient (kg) | 85 | 86 | 87 | 88 | 89 | 90 | 91 |
| viscous liquid | A<br>20 | B<br>20 | C<br>20 | D<br>20 | E<br>30 | F<br>30 | G<br>20 |
| 50% ATG | 13 | 13 | 13 | 13 | — | 13 | 13 |
| cystein | — | — | — | — | 4.5 | — | — |
| ammonia solution | proper amount | proper amount | proper amount | proper amount | 0.5[1)] | proper amount | proper amount |
| 80% monoethanolamine | — | — | — | — | 3.9 | — | — |
| water | remaining volume | remaining volume | remaining volume | remaining volume | remaining volume | remaining volume | remaining volume |
| total amount | 100 | 100 | 100 | 100 | 100 | 100 | 100 |

[1)]in Table 23 indicates 28 wt. % aqueous solution.

Preparation of No. 2 Agents of Waving Agents 1 kg of lauryl trimethyl ammonum chloride, 8 kg of sodium bromate and water was added to prepare 100 kg of aqueous solution. This aqueous solution was used as No. 2 agent of waving agent (Example 85 and 91).

Example 92 and 93

Preparation of No. 1 Agents of Waving Agents

The composition for blending in waving agent (Example 54 or 55), that had been heated to the temperature shown in Table 24 and dissolved homogeneously, was added to initial water, that had been heated to the temperature shown in Table 24, and then emulsified as stirring. After this emulsion was cooled to the temperature shown in Table 24, 50% ATG, MEA and, if necessary, the composition for blending in waving agent (Example 60) were added. Finally, water (add water) was added so as to adjust the total weight to be 100 kg. Thus, No. 1 agents of waving agent was prepared. Ingredients and contents (kg) are shown in Table 24.

Preparation of No. 2 Agents of Waving Agents

The composition for blending in waving agent (Example 54 or 55) was heated to the temperature shown in Table 24, and then dissolved homogeneously. Sodium bromate was added to initial water, and then heated to the temperature shown in Table 24 to prepare aqueous solution. Next, the above-mentioned homogeneously dissolved material was added to the aqueous solution, and then emulsified as stirring.

After this emulsion was cooled to the temperature shown in Table 24, the composition for blending in waving agent (Example 60), if necessary, was added. Finally, water (add water) was added so as to adjust the total weight to be 100 kg. Thus, No. 2 agent of waving agent was prepared. Ingredients and contents (kg) are shown in Table 24.

Example 94

Preparation of No. 1 Agents of Waving Agents

The composition for blending in waving agent (Example 58), 50% ATG, strong ammonia solution and such amount of water as the total weight of waving agent was adjusted to be 100 kg were mixed homogeneously by stirring at room temperature. Thus, No. 1 agent of waving agent was prepared. Ingredients and contents (kg) are shown in Table 24.

Preparation of No. 2 Agents of Waving Agents

The composition for blending in waving agent (Example 60), sodium bromate, lauryl trimethyl ammonum chloride and such amount of water as the total weight of waving agent was adjusted to be 100 kg were mixed homogeneously by stirring at room temperature. Thus, No. 2 agent of waving agent was prepared. Ingredients and contents (kg) are shown in Table 24.

Example 95

Preparation of No. 1 Agents of Waving Agents

No. 1 agent of waving agent was prepared in the same manner as Example 94 except that the composition for blending in waving agent (Example 59) was used instead of the composition for blending in waving agent (Example 58). Ingredients and contents (kg) are shown in Table 24.

Preparation of No. 2 Agents of Waving Agents 1 kg of lauryl trimethyl ammonum chloride, 8 kg of sodium bromate and water were added to prepare 100 kg of aqueous solution. This aqueous solution was used as No. 2 agent of waving agents.

TABLE 24

| | | Example | | | |
|---|---|---|---|---|---|
| | | 92 | 93 | 94 | 95 |
| No. 1 agent | heating temperature(° C.) | 80~85 | 83~87 | — | — |
| | cooling temperature(° C.) | 50~55 | 55 | — | — |
| | ingredient(kg) | | | | |
| | composition blended in waving agent | Example 54 17 Example 60 10 | Example 55 18 | Example 58 5 | Example 59 5 |
| | 50% ATG | 10 | 10 | 13 | 13 |
| | strong ammonia solution | — | — | proper amount | proper amount |
| | 80% monoethanolamine | 3 | 2.5 | — | — |
| | perfume | — | proper amount | — | — |
| | initial water | 42 | 50 | — | — |
| No. 2 agent | heating temperature(° C.) | 80~85 | 65~68 | — | — |
| | cooling temperature(° C.) | 53~55 | 55 | — | — |
| | ingredient(kg) | | | | |
| | composition blended in waving agent | Example 54 23 Example 60 10 | Example 55 26 | Example 60 10 | — |
| | sodium bromate | 4 | 8 | 8 | 8 |
| | lauryl trimethyl ammonium chloride | — | — | 1 | 1 |
| | initial water | 34 | 60 | — | — |

(Preparation of Finishing Agents.)

Examples 96

Each ingredient II–IV was added in order to the homogeneously dissolved ingredient I. On adding each ingredient, the following ingredient was added after it was confirmed that the previously added ingredients had been dissoluved homogeneously. Thus, the finishing agent of the present invention was prepared. The formulation of each ingredient I–VI are shown in Table 25.

Examples 97

After the ingredient III was added to the ingredient II, and then mixed by stirring at 90° C., the ingredient I, that had been heated to 90° C., was added and mixed by stirring homogeneously. On adding each ingredient, the following ingredient was added after it was confirmed that the previously added ingredients had been dissoluved homogeneously. After the mixture was cooled to 70° C., water (add water) was added so as to adjust the total weight to be 100 kg. Thus, the finishing agent of the present invention was prepared. The formulation of each ingredient I–III is shown in Table 25.

TABLE 25

| | | Example | |
|---|---|---|---|
| | ingredient (kg) | 96 | 97 |
| I | composition blended in finishing agent | Example 66 43 | Example 68 42 |
| | isopropyl myristate | — | 6 |
| | propylene gylcol | — | 2 |
| | water | 5 | — |
| II | glycerin | 50 | — |
| | sodium edetate | — | 0.1 |
| | water | — | 39 |

TABLE 25-continued

| | | Example | |
|---|---|---|---|
| | ingredient (kg) | 96 | 97 |
| III | 20% NaOH aqueous solution | 1 | — |
| | 80% monoethanolamine | — | 0.65 |
| | water | — | 10 |
| IV | IPA | 0.9 | — |
| | parabens | 0.1 | — |

(Preparation of Additive That Increases the Feeling Effects)

Example 98

The composition for blending in additive that increases the feeling effects (Example 60) itself was used alone as additive that increases the feeling effects (Example 60). Concretely, 10 kg of the additive that increases the feeling effects (Example 60) was added to 90 kg of the waving agent (Example 93), and then stirred homogeneously to prepare new waving agent.

Next, hair treatings were carried out to 50 monitors with the above-mentioned new waving agent by the following method, and then the organoleptic tests about hair treating effects were carried out. The results of organoleptic tests were summarized in Table 27.

(Preparation of Depilatories.)

Example 99

10 kg of the composition for blending in depilatory (Example 57), that had been heated to 80–85° C. and dissolved homogeneously, was added as stirring to 45 kg of initial water, that had been heated to 80–85° C., and then emulsified. After this emulsion was cooled to 55° C., 3 kg of urea, 6 kg of calcium thioglycolate and 20 kg of water were added, and then further cooled to 45° C. Next, 10 kg of 10% sodium hydroxide aqueous solution was added. Finally, water (add water) was added so as to adjust the total weight to be 100 kg. Thus, depilatory of the present invention was prepared.

(The Organoleptic Tests about Hair Treating Effects of the Hair Treating Agents)

Hair treatings were carried out to 50 monitors by the following methods. And the results of the organoleptic tests about hair treating effects (i.e. feel when used) of the hair treating agents were obtained. The results of organoleptic tests were summarized in Table 26 and 27.

The Method for Hair Treating with Hair Conditioners

After ordinary shampoo, the Liquid 1 of 2-bath type of treatment (Example 69) was applied to hair. Next, the Liquid 2 of 2-bath type of treatment (Examples 69) was applied to hair, and then rinsed, and finally dried using a dryer.

The Method for Hair Treating with Hair Colorings

In a Case of Acidic Hair Coloring Materials

The acidic hair coloring material (Example 70–82) was applied to hair and left for 15 minutes at 45° C. Then, the hair was rinsed and dried using a dryer.

In a Case of Oxidizing Hair Coloring Agents and Decolorizing Agents

No. 1 agents and No. 2 agents of the hair coloring (Example 83 or 84) was mixed (the wt. % ratio of No. 1 agent to No. 2 agent was 1:1). This mixture was applied to hair and left for 30 minutes at room temperature. Then, the hair was rinsed and dried using a dryer.

The Method for Hair Treating with Waving Agents

In a Case of Curling Type Permanent Wave

No. 1 agent of the waving agent (Example 85–91, 95) was applied to hair and spread by combing, and the hair was wound to a rod and left for 7 minutes at room temperature. Then No. 2 agent was applied by an applicator and left for 7 minutes. Repeatedly, No. 2 agent was applied by an applicator and left for 7 minutes. Next, the rod was removed, and the hair was rinsed and dried using a dryer.

In a Case of Straight Type Permanent Wave

No. 1 agent of the waving agent (Example 92–94) was applied to hair and spread by combing and the hair was formed to the straight shape. Then, the hair was left for 10 minutes. After that, No. 2 agents was applied to hair and spread by combing, further left for 10 minutes, and finally, rinsed and dried using a dryer.

The Method for Hair Treating with Finishing Agents

The finishing agent (Example 96, 97) was applied to hair and spread.

The Method for Hair Treating with Depilatories

The depilatory (Example 99) was applied to the skin, and left for 15 minutes. After the depilatory was removed with cotton, the skin was washed

TABLE 26

| feel when used | hair treating agent (Example) | | | | | | | | | | | | | | | |
|---|---|---|---|---|---|---|---|---|---|---|---|---|---|---|---|---|
| and functionality | 69 | 70 | 71 | 72 | 73 | 74 | 75 | 76 | 77 | 78 | 79 | 80 | 81 | 82 | 83 | 84 |
| slightly oily feel | Δ | Δ | Δ | Δ | Δ | Δ | Δ | Δ | Δ | Δ | Δ | Δ | Δ | Δ | Δ | Δ |
| smooth feel | ◎ | Δ | Δ | Δ | Δ | Δ | Δ | Δ | Δ | Δ | Δ | Δ | Δ | Δ | Δ | Δ |
| soft feel | ◎ | Δ | Δ | Δ | Δ | Δ | Δ | Δ | Δ | Δ | Δ | Δ | ○ | ○ | ○ | ○ |
| moist feel | ◎ | Δ | Δ | Δ | Δ | Δ | Δ | Δ | Δ | Δ | Δ | Δ | Δ | Δ | Δ | Δ |
| luster | ○ | Δ | Δ | Δ | Δ | Δ | Δ | Δ | Δ | Δ | Δ | Δ | Δ | Δ | Δ | Δ |
| pleasant sense of touch to the wave | — | — | — | — | — | — | — | — | — | — | — | — | — | — | — | — |
| adhesive | — | ◎ | ◎ | ◎ | ◎ | ◎ | ◎ | ◎ | ◎ | ◎ | ◎ | ◎ | ◎ | ◎ | ◎ | ◎ |
| well spread | — | ◎ | ◎ | ◎ | ◎ | ◎ | ◎ | ◎ | ◎ | ◎ | ◎ | ◎ | ◎ | ◎ | ◎ | ◎ |
| moisturizing ability of waving ability | — | — | — | — | — | — | — | — | — | — | — | — | — | — | — | — |
| no drip | — | ◎ | ◎ | ◎ | ◎ | ◎ | ◎ | ◎ | ◎ | ◎ | ◎ | ◎ | ◎ | ◎ | ◎ | ◎ |
| easy appliance | — | ◎ | ◎ | ◎ | ◎ | ◎ | ◎ | ◎ | ◎ | ◎ | ◎ | ◎ | ◎ | ◎ | ◎ | ◎ |
| retouching workability | — | ◎ | ◎ | ◎ | ◎ | ◎ | ◎ | ◎ | ◎ | ◎ | ◎ | ◎ | ◎ | ◎ | ◎ | ◎ |
| firmly rooted and no uneven wave formation | — | — | — | — | — | — | — | — | — | — | — | — | — | — | — | — |
| appliability of dye at r.t. | — | ○ | ○ | ○ | ○ | ○ | ○ | ○ | ○ | ○ | ◎ | ○ | Δ | Δ | Δ | Δ |
| less harsh smell of ammonia | — | — | — | — | — | — | — | — | — | — | — | — | — | — | — | — |
| quick wave formation | — | — | — | — | — | — | — | — | — | — | — | — | — | — | — | — |
| less unpleasant residual odors after permanent | — | — | — | — | — | — | — | — | — | — | — | — | — | — | — | — |
| silky touch and appearance | — | — | — | — | — | — | — | — | — | — | — | — | — | — | — | — |
| low irritation to the skin | — | — | — | — | — | — | — | — | — | — | — | — | — | — | — | — |

TABLE 27

| feel when used | hair treating agent (Example) | | | | | | | | | | | | | | |
|---|---|---|---|---|---|---|---|---|---|---|---|---|---|---|---|
| and functionality | 85 | 86 | 87 | 88 | 89 | 90 | 91 | 92 | 93 | 94 | 95 | 96 | 97 | 98 | 99 |
| slightly oily feel | ◎ | ◎ | ◎ | ○ | Δ | ◎ | ◎ | ◎ | ◎ | Δ | Δ | Δ | ◎ | ◎ | — |
| smooth feel | ○ | ◎ | ◎ | ○ | ◎ | ○ | ○ | ◎ | ◎ | ○ | ○ | Δ | Δ | ◎ | — |
| soft feel | Δ | ◎ | ◎ | ○ | Δ | ◎ | ◎ | ◎ | ○ | Δ | ○ | Δ | Δ | ◎ | — |
| moist feel | ○ | Δ | Δ | Δ | Δ | ◎ | ◎ | ◎ | ○ | Δ | Δ | Δ | Δ | ◎ | — |
| luster | Δ | Δ | Δ | Δ | Δ | ○ | ○ | Δ | Δ | Δ | Δ | ○ | ○ | Δ | — |
| pleasant sense of touch to the wave | ◎ | ◎ | ◎ | ◎ | ◎ | ◎ | ◎ | ◎ | ◎ | ○ | ○ | — | — | ◎ | — |
| adhesive | ○ | ○ | ○ | ○ | ○ | ○ | ○ | ○ | ◎ | Δ | Δ | — | — | ○ | ○ |
| well spread | ○ | ○ | ○ | ○ | ○ | ○ | ○ | ○ | ◎ | Δ | Δ | — | — | ○ | ○ |
| moisturizing ability of waving ability | ◎ | ◎ | ◎ | ◎ | ○ | ◎ | ◎ | ○ | ◎ | ○ | ○ | — | — | ○ | — |
| no drip | ○ | ○ | ○ | ○ | ○ | ○ | ○ | ○ | ○ | ○ | ○ | — | — | ○ | ◎ |

TABLE 27-continued

| feel when used and functionality | hair treating agent (Example) | | | | | | | | | | | | | | |
|---|---|---|---|---|---|---|---|---|---|---|---|---|---|---|---|
| | 85 | 86 | 87 | 88 | 89 | 90 | 91 | 92 | 93 | 94 | 95 | 96 | 97 | 98 | 99 |
| easy appliance | ○ | ○ | ○ | ○ | ○ | ○ | ○ | ○ | ○ | ○ | ○ | — | — | ○ | — |
| retouching workability | — | — | — | — | — | — | — | — | — | — | — | — | — | — | — |
| firmly rooted and no uneven wave formation | ◎ | ◎ | ◎ | ◎ | ◎ | ○ | ○ | Δ | Δ | ◎ | ◎ | — | — | — | — |
| appliability of dye at r.t. | — | — | — | — | — | — | — | — | — | — | — | — | — | — | — |
| less harsh smell of ammonia | ◎ | ◎ | ◎ | ◎ | ○ | ◎ | ◎ | ◎ | ◎ | ○ | ◎ | — | — | ◎ | — |
| quick wave formation | Δ | Δ | Δ | Δ | ○ | Δ | Δ | — | — | ◎ | ○ | — | — | — | — |
| less unpleasant residual odors after permanent | — | — | — | — | — | — | — | — | — | — | ◎ | — | — | — | — |
| silky touch and appearance | — | — | — | — | ◎ | — | — | — | — | — | — | — | — | — | — |
| low irritation to the skin | — | — | — | — | — | — | — | — | — | — | — | — | — | — | ◎ |

In Table 26 and 27,
◎ indicates "very good ",
○ indicates "good " and
Δ indicates "normal".

As clearly understood from the results of the above-mentioned Examples, the compositions for blending in hair treating agents of the present embodiment are prepared by selecting and combining adequately the ingredients which are cheap and easy to purchase so as to display an excellent hair treating effect. Therefore, the compositions for blending in hair treating agents of the present invention may be produced by lower cost and easily.

Since the hair treating agents of the present embodiment are prepared using above-mentioned compositions for blending in hair treating agents of the present invention, the costs for production are low, further, have excellent feels when used such as slightly oily feel, smooth feel, soft feel, moist feel, luster, pleasant sense of touch to the hair, and have excellent functionalities such as adhesive, well spread, moisturizing ability, no drip, easy appliance (applicability), easiness of retouching work (retouching workability), no uneven and firmly rooted wave formation, less harsh smell (of ammonia etc.), quick wave formation, less unpleasant residual oders after permanent, good appearance of treating agent (for example, high-class pearly appearance), low irritation to the skin etc. Further, in the preparation process of hair treating agentsince it is possible by using the compositions for blending in a hair treating agents of the present invention to blend alcohols and at least one selected from the groups consisting of anionic surfactants, inorganic acids and inorganic alkaline agents etc. at a time, the production process may be remarkably simplified.

Example of the Third Embodiment

The third embodiment of the present invention is illustrated more concretely according to the following Examples. (Preparation of the Compositions for Blending in Hair Treating Agents.)

Examples 100–110

The amount (kg) shown in Table 28 and 29 of each ingredient was poured into a vessel and mixed, and the mixture was heated to the temperature shown in Table 28 and 29, then stirred and dissolved completely. Thus, the compositions for blending in hair treating agents (Examples 100–110) of the present invention were prepared. The heating temperature (° C.), ingredients and contents (kg) are shown in Table 28 and 29.

Examples 111

Citric acid, carboxyvinylpolymer, methyl parahydroxybenzoate, propyl parahydroxybenzoate and ethanol were added to water as stirring in order, and then mixed homogeneously. Next, after this mixture was stirred under reduced pressure, cetyl trimethyl ammonium chloride was added to this mixture under normal pressure, and then mixed to prepare homogeneous mixture. The ingredients and contents (kg) are shown in Table 29.

TABLE 28

| | Example | | | | | |
|---|---|---|---|---|---|---|
| | 100 | 101 | 102 | 103 | 104 | 105 |
| heating temperature (° C.) | 80 | 80 | 80 | 80 | 85 | 80 |
| ingredient (kg) | | | | | | |
| propylene glycol | — | — | 27 | — | — | — |
| conc. glycerin | — | — | — | — | 43 | — |
| sorbit | — | — | — | — | — | — |
| D-mannitol | — | — | — | — | — | — |
| ethanol | — | — | — | — | — | — |
| myristyl alcohol | — | — | — | — | — | — |
| cetanol | 62 | 43 | 48 | 22 | 23 | 43 |
| behenyl alcohol | — | — | — | 9 | — | — |
| distearyl dimethyl ammonium chloride[1)] | — | — | — | — | — | — |
| dicocoyl dimethyl ammonium chloride[2)] | — | — | — | — | — | — |
| lauryl trimethyl ammonium bromide[3)] | — | 6 | — | — | — | 6 |
| cetyl trimethyl ammonium chloride | — | — | 19[4)] | 11[3)] | — | — |
| cetyl trimethyl ammonium bromide[4)] | — | 18 | — | — | — | 18 |
| stearyl trimethyl ammonium chloride[5)] | 23 | — | — | — | 7 | — |
| behenyl trimethyl ammonium chioride[6)] | 15 | — | — | — | 9 | — |
| lauryl pyridinium chloride[7)] | — | — | — | — | — | — |
| cethyl trimethyl ammonium saccarinate[8)] | — | — | — | — | — | — |
| lauryl dimethylaminoacetic acid betaine | — | — | — | — | — | — |
| 2-alkyl N-carboxymethyl N-hydroxyethyl imidazolinium betaine[10)] | — | — | — | — | — | — |
| hydrogenated oil[12)] | — | — | — | — | — | — |
| olive oil | — | 30 | — | — | — | — |
| sasanqua oil | — | — | — | — | — | 30 |
| lanolin | — | — | 6 | — | — | — |
| hard lanolin | — | — | — | 11 | — | — |
| paraffin | — | — | — | — | — | — |
| liquid petrolatum | — | — | — | 47 | 18 | — |
| candelilla wax | — | 3 | — | — | — | 3 |

TABLE 28-continued

| | Example | | | | | |
|---|---|---|---|---|---|---|
| | 100 | 101 | 102 | 103 | 104 | 105 |
| citric acid | — | — | — | — | — | — |
| phosphoric acid[13] | — | — | — | — | — | — |
| disodium phosphate | — | — | — | — | — | — |
| disodium edetate | — | — | — | — | — | — |
| pentasodium diethylenetriamine pentaacetate[11] | — | — | — | — | — | — |
| methyl parahydroxybenzoate | — | — | — | — | — | — |
| propyl parahydroxybenzoate | — | — | — | — | — | — |
| carboxyvinylpolymer | — | — | — | — | — | — |
| water | — | — | — | — | — | — |

TABLE 29

| | Example | | | | | |
|---|---|---|---|---|---|---|
| | 106 | 107 | 108 | 109 | 110 | 111 |
| heating temperature (° C.) | 80 | 80 | 85 | 60~70 | 55~60 | — |
| ingredient (kg) | | | | | | |
| propylene glycol | — | — | — | — | — | — |
| conc. glycerin | 28 | — | — | — | — | — |
| sorbit | — | — | — | — | 1[4] | — |
| D-mannitol | — | — | — | 1 | — | — |
| ethanol | — | — | — | — | — | 2 |
| myristyl alcohol | — | 20 | — | — | — | — |
| cetanol | 49 | — | 70 | — | — | — |
| behenyl alcohol | — | 40 | — | — | — | — |
| distearyl dimethyl ammonium chloride[1] | — | — | 5 | — | — | — |
| dicocoyl dimethyl ammonium chloride[2] | — | 2.5 | — | — | — | — |
| lauryl trimethyl ammonium bromide[3] | — | — | — | — | — | — |
| cetyl trimethyl ammonium chloride | — | — | — | — | — | 14[3] |
| cetyl trimethyl ammonium bromide[4] | — | — | — | — | — | — |
| stearyl trimethyl ammonium chloride[5] | 15 | — | 20 | — | — | — |
| behenyl trimethyl ammonium chloride[6] | 8 | 17.5 | — | — | — | — |
| lauryl pyridinium chloride[7] | — | — | — | 25 | — | — |
| cethyl trimethyl ammonium saccarinate[8] | — | — | — | — | 33 | — |
| lauryl dimethylaminoacetic acid betaine[9] | — | — | — | 19 | — | — |
| 2-alkyl N-carboxymethyl N-hydroxyethyl imidazolinium betaine[10] | — | — | — | — | 5 | — |
| hydrogenated oil[12] | — | 20[12] | — | — | — | — |
| olive oil | — | — | — | — | — | — |
| sasanqua oil | — | — | — | — | — | — |
| lanolin | — | — | — | — | — | — |
| hard lanolin | — | — | — | — | — | — |
| paraffin | — | — | 5 | — | — | — |
| liquid petrolatum | — | — | — | — | — | — |
| candelilla wax | — | — | — | — | — | — |
| citric acid | — | — | — | — | — | 2 |
| phosphoric acid[13] | — | — | — | 0.03[13] | — | — |
| disodium phosphate | — | — | — | — | 1 | — |
| disodium edetate | — | — | — | — | 0.3 | — |
| pentasodium diethylenetriamine pentaacetate[11] | — | — | — | 0.1 | — | — |
| methyl parahydroxybenzoate | — | — | — | — | — | 0.1 |
| propyl parahydroxybenzoate | — | — | — | — | — | 0.1 |
| carboxyvinylpolymer | — | — | — | — | — | 1.5 |
| water | — | — | — | 54.87 | 59.7 | 80.3 |

1)–13) in Table 28 and 29 indicate,
1) Content, 75 wt. %,
2) Content, 75 wt. %,
3) Content, 50 wt. %,
4) Content, 70 wt. %,
5) Content, 60 wt. %,
6) Content, 80 wt. %,
7) Content, 40 wt. %,
8) Content, 35 wt. %,
9) Content, 26 wt. %,
10) Content, 10 wt. %,
11) Content, 88 wt. %,
12) hydrogenated rice oil,
13) Content, 85 wt. %.

When some ingredient shown in the Tables is mixture with other ingredient, the content of said other ingredient shown in the column of the tables doesn't include the content of said other ingredient which is contained in the mixture. For example, when some cationic surfactant shown in the Tables is mixture with ethanol, the content of "ethanol" shown in the column of the tables doesn't include the content of ethanol which is contained in the mixture.

(Preparation of Hair Conditioners)

Examples 112, 113, 115–117

Initial purified water was heated to the temperature shown in the Table 30. On the other hand, the composition for blending in a hair conditioner obtained above (Example 102, 103, or 106) was heated to the temperature shown in the Table 30, and then dissolved homogeneously. To this, methyl polysiloxane, parabens, mink oil, additive composition and ethanol were added to prepare homogeneously dissolved material. The homogeneous dissolved material was added to the above-mentioned heated water with constant stirring and emulsified.

Then the emulsion was cooled down to the temperature shown in the Table 30 with constant stirring. Next, perfume and malic acid, if necessary, were added, and finaly water (add water) was added so as to adjust the total weight to be 100 kg and then mixed homogeneously. Thus, the hair conditioner of the present invention (Examples 112, 113, 115–117) was prepared. The heating temperature (° C.), the cooling temperature (° C.), ingredients and contents (kg) are shown in Table 30.

Examples 114

The composition for blending in a hair conditioner (Examples 104), methyl polysiloxane and parabens was heated to 80–85° C., and mixed as stirring to prepare homogeneously dissolved material. On the other hand, initial purified water was heated to 80–85° C. This heated water was added to the above-mentioned homogeneously dissolved material with constant stirring and emulsified.

Then the emulsion was cooled down 60° C. with constant stirring. Next, perfume was added, and finaly water (add water) was added so as to adjust the total weight to be 100 kg and then mixed homogeneously. Thus, the hair conditioner of the present invention was prepared. The heating temperature (° C.), the cooling temperature (C), ingredients and contents (kg) are shown in Table 30.

Examples 118

The additive composition, that had been heated to 80–85° C. and dissolved homogeneously, was added to the water, that had been heated to 80–85° C., with constant stirring and emulsified. Then the emulsion was cooled down below 40° C. with constant stirring. Next, the composition for blending in a hair conditioner (Examples 111) and perfume were added, and finaly water (add water) was added so as to adjust the total weight to be 100 kg and then mixed homogeneously. Thus, the hair conditioner of the present invention was prepared. The heating temperature (° C.), the cooling temperature (° C.), ingredients and contents (kg) are shown in Table 30.

TABLE 30

| | Example | | | | | | |
|---|---|---|---|---|---|---|---|
| | 112 | 113 | 114 | 115 | 116 | 117 | 118 |
| heating temperature (° C.) | 83~88 | 83~86 | 80~85 | 85~90 | 85~90 | 85~90 | 83~86 |
| cooling temperature (° C.) | 50 | 45 | 60 | 60 | 60 | 60 | 40 |
| ingredient(kg) | | | | | | | |
| composition blended in hair conditioner | Example 102 19 | Example 103 25 | Example 104 10 | Example 106 7 | Example 106 13 | Example 106 16 | Example 111 20 |
| parabens | — | 0.15 | 0.15 | 0.15 | 0.15 | — | — |
| perfume | proper amount | proper amount | proper amount | proper amount | proper amount | proper amount | proper amount |
| methyl polysiloxane | 0.6[1)] | — | 5 | 0.5[2)] | 2.4[3)] | — | — |
| malic acid | 0.1 | — | — | — | — | — | — |
| additive composition | — | — | — | — | — | 10[4)] | 10.2[5)] |
| mink oil | — | — | — | 0.5 | 0.5 | — | — |
| ethanol | — | — | — | — | — | 2 | — |
| initial water | 75 | 70 | 50 | 70 | 70 | 70 | 70 |

1)–5) in Table 30 are indicating,
1)mixture of 1000 cs (0.4 kg) and 100 cs (0.2 kg) ],
2)3000 cs,
3)mixture of 3000 cs (0.8 kg) and 20 cs (1.6 kg) ],
4)Ingredient (wt. %); decamethyl cyclopentasiloxane (89), highly polymerized dimethyl polysiloxane (9), dimethyl polysiloxane (2).
5)Ingredient (wt. %); stearyl alcohol (34.3), lipophilic glyceryl monostearate (34.3), polyoxyethylene (20EO) cetyl ether (14.7), 70 wt. % cetyl trimethyl ammonium chloride (16.7).

(Preparation of Waving Agents)

Example 119

Preparation of No. 1 Agents of Waving Agents 60 kg of initial water, 13 kg of 50 wt. % ammonium thioglycolate (ATG) aqueous solution, proper amount of strong ammonia solution and 5 kg of the composition for blending in a waving agent (Example 110) were added in order. Further, water (add water) was added so as to adjust the total weight to be 100 kg. Thus No. 1 agent of waving agent was prepared.

Preparation of No. 2 Agents of Waving Agents 60 kg of initial water, 8 kg of sodium bromate and 2 kg of the composition for blending in a waving agent (Example 109) were added in order. Further, water (add water) was added so as to adjust the total weight to be 100 kg. Thus, No. 2 agent of waving agent was prepared.

(Preparation of Finishing Agents)

Example 120

Initial purified water was heated to 80–85° C. On the other hand, additive composition and parabens were added to the composition for blending in a finishing agent (Example 104), and then this mixture was heated to 80–85° C. to prepare homogeneously dissolved material. The above-mentioned heated water was added to the above-mentioned homogeneously dissolved material with constant stirring and emulsified.

Then the emulsion was cooled down 60° C. with constant stirring. Next, perfume was added, and finaly water (add water) was added so as to adjust the total weight to be 100 kg and then mixed homogeneously. Thus, the finishing agents (so called "non rinsing treatments") of the present invention was prepared. The ingredients and contents (kg) are shown in Table 31.

Example 121

The composition for blending in a finishing agent (Examples 106), jojoba oil, squalane, parabens and oxybenzone were heated as stirring to 80–85° C. to prepare homogeneously dissolved material. Further, additive composition and ethanol were added to the homogeneously dissolved material, and then mixed as stirring to prepare homogeneous mixture. Initial purified water, that had been heated to 80–85° C., was added as stirring to prepare emulsion.

Then the emulsion was cooled down 60° C. with constant stirring. Next, perfume was added, and finaly water (add water) was added so as to adjust the total weight to be 100 kg and then mixed homogeneously. Thus, the finishing of the present invention was prepared. The ingredients and contents (kg) are shown in Table 31.

TABLE 31

| | Example | |
|---|---|---|
| ingredient (kg) | 120 | 121 |
| composition blended in finishing agent | Example 104 15 | Example 106 15 |

TABLE 31-continued

| ingredient (kg) | Example 120 | Example 121 |
|---|---|---|
| additive composition[1)] | 15 | 15 |
| parabens | 0.15 | 0.15 |
| perfume | proper amount | proper amount |
| jojoba oil | — | 0.5 |
| squalane | — | 0.5 |
| oxybenzone. | — | 0.1 |
| ethanol | — | 2 |
| initial water | 50 | 50 |

[1)]in Table 31 indicates the same additive composition as Example 117.

(The Organoleptic Tests about Hair Treating Effects of the Hair Treating Agents)

Hair treatings were carried out to 50 monitors by the following methods. And the results of the organoleptic tests about hair treating effects (i.e. feel when used) of the hair treating agents were obtained. The results of organoleptic tests were summarized in Table 32.

The Method for Hair Treating with Hair Conditioners

After ordinary shampoo, a specimen of each hair conditioner (Examples 112–118) was applied to hair and spread by combing, and then rinsed and dried using a dryer.

The Method for Hair Treating with Waving Agents

No. 1 agent of the waving agent (Example 119) was applied to hair and spread by combing, and the hair was wound to a rod and heated for 7 minutes at 45° C. Then No. 2 agent was applied by an applicator and left for 7 minutes. Repeatedly, No. 2 agents was applied by an applicator and left for 7 minutes. After the rod was removed, the hair was rinsed and dried using a dryer.

The Method for Hair Treating with Finishing Agents

The finishing agent (Example 120 and 121) was applied to hair and spread.

TABLE 32

| feel when used and functionality | hair treating agent (Example) 112 | 113 | 114 | 115 | 116 | 117 | 118 | 119 | 120 | 121 |
|---|---|---|---|---|---|---|---|---|---|---|
| supple | ⊚ | ⊚ | Δ | Δ | Δ | ○ | ⊚ | ○ | ⊚ | ⊚ |
| moist feel | ⊚ | Δ | ○ | ○ | ○ | ○ | Δ | ○ | Δ | Δ |
| smooth feel | Δ | ⊚ | ○ | ⊚ | ⊚ | ○ | ⊚ | ⊚ | ○ | ○ |
| rustle feeling | ○ | ○ | ○ | ⊚ | ⊚ | ○ | ○ | Δ | ○ | ○ |
| pleasant sense of touch to the hair | ○ | ⊚ | ○ | ○ | ○ | ○ | ○ | ⊚ | ○ | ○ |
| slippery feel | ○ | ○ | ○ | ⊚ | ⊚ | ○ | ⊚ | Δ | — | — |
| soft feel | ○ | Δ | Δ | Δ | Δ | Δ | ⊚ | Δ | Δ | Δ |
| no tangle and no twining | — | — | — | — | — | — | — | ⊚ | ⊚ | ⊚ |
| well spread and adhesiveness of waving agent | — | — | — | — | — | — | — | ⊚ | — | — |
| tight-knit wave | — | — | — | — | — | — | — | ⊚ | — | — |
| firmly rooted wave | — | — | — | — | — | — | — | ⊚ | — | — |

In Table 32,
⊚ indicates "very good",
○ indicates "good" and
Δ indicates "normal".

As clearly understood from the results of the above-mentioned Examples, the compositions for blending in hair treating agents of the present embodiment are prepared by selecting and combining adequately the ingredients which are cheap and easy to purchase so as to display excellent hair treating effects. Therefore, the compositions for blending in hair treating agents of the present invention can be produced by lower cost and easily.

Since the hair treating agents of the present embodiment are prepared using above-mentioned compositions for blending in hair treating agents of the present invention, the costs for production are low, further, have excellent feels when used such as suppleness, moist feel, smooth feel, rustle feeling, pleasant sense of touch to the hair, slippery feel, soft feel, no tangle and no twining, and have excellent functionalities such as spreadability and adhesiveness of waving agent, a tight-knit wave, firmly rooted wave formation etc. Further, in the preparation process of hair treating agentsince it is possible by using the compositions for blending in hair treating agents of the present invention to blend alcohols and cationic surfactants etc. at a time, the production process may be remarkably simplified.

Example of the Fourth Embodiment

The fourth embodiment of the present invention is illustrated more concretely according to the following Examples.

(Preparation of the Compositions for Blending in Hair Treating Agents)

Examples 122–130, 132–139, 144

The amount (kg) shown in Table 33–40 of each ingredient was poured into a vessel and mixed, and the mixture was heated to the temperature shown in Table 33, 35, 37 and 39, then stirred and dissolved completely. Thus, the compositions for blending in hair treating agents (Examples 122–130, 132–139, 144) of the present invention were prepared. The heating temperatures (° C.), ingredients and contents (kg) are shown in Table 33–40.

Examples 131

Lauryl trimethyl ammonium chloride, coconut fatty acid diethanolamide, poly N,N'-dimethyl-3,5-methylene-piperidinium chloride and water were heated to 70–80° C., and then mixed as stirring. After this mixture was cooled to 50° C., methyl parahydroxybenzoate, propyl parahydroxybenzoate and ethanol were added, and then mixed homogeneously. Thus, the composition for blending in hair treating agent of the present invention was prepared. The heating temperature (° C.), ingredients and contents (kg) are shown in Table 35 and 36.

Examples 140

Oleyl alcohol, polyoxyethylene oleyl ether[2.36 kg (7 EO)+0.69 kg (15 EO)+0.98 kg (20 EO)], jojoba oil and liquid petrolatum were mixed, and then heated to the temperature shown in Table 37 to prepare homogeneously dissolved material. The above-mentioned heated homogeneously dissolved material was added to 32.79 kg of water, that had been heated to the temperature shown in Table 37, with constant stirring and mixed. Then, 3.93 kg of ice was added, and then the mixture was cooled below 30° C. to prepare homogeneous mixture.

On the other hand, lauryl trimethyl ammonium chloride, cetyl trimethyl ammonum chloride and 11.8 kg of water were mixed. After this mixture was heated to 80–100° C., and then mixed as stirring, this mixture was cooled below 30° C. to prepare homogeneously dissolved material (I).

Further, polyoxyethylene oleyl ether[2.66 kg (30 EO)+1.34 kg (50 EO)]and 17.7 kg of water were mixed. After this mixture was heated to 80–100° C., and then mixed as stirring, this mixture was cooled below 30° C. to prepare homogeneously dissolved material (II).

The afore-mentioned homogeneously dissolved material (I) and (II) were added in order. Next, sorbic acid, phosphoric acid and sodium hydroxide were added. Finally, water (add water) was further added so as to adjust the total weight to be 100 kg, and mixed homogeneously. Thus, the composition for blending in hair treating agent of the present invention was prepared. The heating temperature (° C.), ingredients and contents (kg) are shown in Table 37 and 38.

Examples 141

According to the formulations shown in Table 37 and 38, homogeneous mixture was prepared in the same manner as Example 140 except that polyoxyethylene oleyl ether [3.88 kg (7 EO)+1.01 kg (15 EO)+1.72 kg (20 EO)], lanolin and 34.45 L of water were used respectively instead of polyoxyethylene oleyl ether[2.36 kg (7 EO)+0.69 kg (15 EO)+0.98 kg (20 EO)], jojoba oil, 32.79 kg of water and 3.93 kg of ice.

On the other hand, according to the formulations shown in Table 37 and 38, homogeneously dissolved material (I) was prepared in the same manner as Example 140 except that 19.69 kg of water was used instead of 11.8 kg of water.

The afore-mentioned homogeneously dissolved material (I) was added as stirring to the afore-mentioned homogeneous mixture. Next, sorbic acid, phosphoric acid and sodium hydroxide were added. Finally, water (add water) was further added so as to adjust the total weight to be 100 kg, and mixed homogeneously. Thus, the compositions for blending in hair treating agents of the present invention were prepared. The heating temperature (° C.), ingredients and contents (kg) are shown in Table 37 and 38.

Examples 142

Polyoxyethylene oleyl ether, safflower oil, oleic acid and liquid petrolatum were mixed, and then heated to the temperature shown in Table 37 to prepare homogeneously dissolved material. The above-mentioned heated homogeneously dissolved material was added to 36.07 kg of water, that had been heated to the temperature shown in Table 37, with constant stirring and emulsified. After the emulsion was cooled as stirring below 30° C., water (add water) was further added so as to adjust the total weight to be 61.48 kg to prepare emulsion (A).

On the other hand, aqueous solution (B) comprising 24.59 kg of water and cetyl pyridinium chloride was prepared. Also, aqueous solution (C) comprising 1.48 kg of water and dibasic sodium phosphate was prepared.

The above-mentioned aqueous solution (B) and (C) were added to the emulsion (A). Finally, water (add water) was further added so as to adjust the total weight to be 100 kg, and mixed homogeneously. Thus, the composition for blending in hair treating agent of the present invention was prepared. The heating temperature (° C.), ingredients and contents (kg) are shown in Table 37 and 38.

Examples 143

Lauryl trimethyl ammonum chloride, benzalkonium chloride, polyoxyethylene lauryl ether, polyoxyethylene nonylphenyl ether and lauric acid diethanolamide were mixed, and then heated to the temperature shown in Table 39 to prepare homogeneously dissolved material. Aqueous solution comprising 41.46 kg of water and disodium edetate was prepared, and then heated to the temperature shown in Table 39. The above-mentioned heated homogeneously dissolved material was added as stirring to the heated aqueous solution to prepare solution.

After this solution was cooled as stirring below 30° C., the pH was adjusted to 6–7 by adding isopropanol, dibasic sodium phosphate, if necessary, and water. Finally, water (add water) was further added so as to adjust the total weight to be 100 kg, and mixed homogeneously. Thus, the composition for blending in hair treating agent of the present invention was prepared. The ingredients and contents (kg) are shown in Table 39 and 40.

Examples 145

Methyl polysiloxane (100,000 cs.), polyoxyethylene lauryl ether [0.8 kg (2 EO)+0.6 kg (20 EO)], glycerin and 11.9 kg of water were mixed to prepare homogeneous emulsion A.

Methyl polysiloxane (350 cs), polyoxyethylene lauryl ether [0.6 kg (2 EO)+0.6 kg (20 EO)] and 12.6 kg of water were mixed to prepare homogeneous emulsion B.

Stearyl trimethyl ammonium chloride, diethylene glycol monoethyl ether and parabens were mixed to prepare homogeneous emulsion C.

Next, 43.25 kg of water, ingredient A, B and C were added in order. Thus, the composition for blending in hair treating agent of the present invention was prepared. The ingredients and contents (kg) are shown in Table 39 and 40.

Examples 146

Concentrated glycerin, cetyl trimethyl ammonum chloride, cethyl trimethyl ammonium saccarinate and polyoxyethylene nonylphenyl ether were added in order to 57.02 kg of water, that had been heated to the temperature shown in Table 39, and mixed as stirring, and then homogeneously dissolved. Next, lactic acid and zinc sulfate were added and mixed as stirring to prepare homogeneously dissolved material.

After the homogeneously dissolved material was cooled below 45° C., water (add water) was added so as to adjust the total weight to be 100 kg, and mixed homogeneously. Thus, the composition for blending in hair treating agent of the present invention was prepared. The ingredients and contents (kg) are shown in Table 39 and 40.

Examples 147

The composition for blending in hair treating agent of the present invention was prepared in the same manner as Example 146 except that polyoxyethylene lauryl ether was used instead of polyoxyethylene nonylphenyl ether. The heating temperature (° C.), ingredients and contents (kg) are shown in Table 39 and 40.

Examples 148

The composition for blending in hair treating agent of the present invention was prepared in the same manner as Example 146 except that dipolyoxyethylene oleyl methyl ammonium chloride was used instead of cetyl trimethyl ammonium chloride. The heating temperature (° C.), ingredients and contents (kg) are shown in Table 39 and 40.

Examples 149

According to the formulations shown in Table 39 and 40, the composition for blending in hair treating agent of the present invention was prepared in the same manner as Example 146 except that dipolyoxyethylene oleyl methyl ammonium chloride and magnesium sulfate was used respectedly instead of cetyl trimethyl ammonium chloride and zinc sulfate. The heating temperature (° C.), ingredients and contents (kg) are shown in Table 39 and 40.

TABLE 33

| | Example | | | | | | |
|---|---|---|---|---|---|---|---|
| | 122 | 123 | 124 | 125 | 126 | 127 | 128 |
| ingredient (° C.) | 80 | 80 | 80 | 85 | 80 | 80 | 80 |
| ingredient (kg) | | | | | | | |
| ethanol | — | — | — | — | — | — | — |
| isopropanol | — | — | — | — | — | — | — |
| lauryl alcohol | — | — | — | — | — | — | — |
| myristyl alcohol | — | 15 | — | — | — | — | — |
| cetanol | — | — | 44 | — | 54 | 52 | 44 |
| oleyl alcohol | — | — | — | — | — | — | — |
| arachyl alcohol | 11 | — | — | — | — | — | — |
| behenyl alcohol | 12 | 30 | — | 65 | — | — | — |
| cetostearyl alcohol | — | — | — | — | — | — | — |
| propylene glycol | — | — | — | — | — | — | — |
| 1.3-butylene glycol | 18 | — | — | 14 | — | — | — |
| 3-methyl-1,3-butandiol | 9 | — | — | — | — | — | — |
| diethylene glycol monoethyl ether | — | — | — | — | — | — | — |
| conc. glycerin | — | — | — | — | — | — | — |
| 70% sorbitol solution | — | — | — | — | — | — | — |
| distearyl dimethyl ammonium chloride | — | — | 18[1)] | — | — | — | — |
| dipolyoxyethylene oleyl methyl ammonium chloride | — | — | — | — | — | — | — |
| stearyl dimethyl benzyl ammonium chloride | — | — | — | — | — | — | 27[2)] |
| benzalkonium chloride | — | — | — | — | — | — | — |
| lauryl trimethyl ammonium chloride | — | — | — | — | — | — | — |
| cetyl trimethyl ammonium chloride | — | — | — | — | 38[3)] | — | — |
| cetyl trimethyl ammonium bromide[4)] | — | — | — | — | — | 40 | 14 |
| stearyl trimethyl ammonium chloride | — | — | — | 19.5[5)] | — | — | — |
| stearyl trimethyl ammonium bromide | 8[6)] | — | — | — | — | — | — |
| behenyl trimethyl ammonium chloride[7)] | — | 28 | 35 | — | — | — | — |
| cethyl trimethyl ammonium saccarinate. | — | — | — | — | — | — | — |
| cetyl pyridinium chloride | — | — | — | — | — | — | — |

[1)–7)] in Table 33 indicate,
[1)]Content, 75 wt. %,
[2)]Content, 90 wt. %,
[3)]Content, 70 wt. %,
[4)]Content, 70 wt. %,
[5)]Content, 60 wt. %,
[6)]Content, 70 wt. %,
[7)]Content, 80 wt. %.

TABLE 34

| | Example | | | | | | |
|---|---|---|---|---|---|---|---|
| | 122 | 123 | 124 | 125 | 126 | 127 | 128 |
| ingredient (kg) | | | | | | | |
| polyoxyethylene lauryl ether | — | — | — | — | — | — | — |
| polyoxyethylene cetyl ether | — | — | — | — | — | — | — |
| polyoxyethylene oleyl ether | 30[1)] | — | — | — | — | — | — |
| polyoxyethylene nonylphenyl ether | — | — | 3[2)] | — | — | — | — |
| polyoxyethylene hydrogenated castor oil | — | 2[3)] | — | — | — | — | — |
| polyoxyethylene almond oil | 12[4)] | — | — | — | — | — | — |

TABLE 34-continued

| | Example | | | | | | |
|---|---|---|---|---|---|---|---|
| | 122 | 123 | 124 | 125 | 126 | 127 | 128 |
| polyoxyethylene lanolin[5)] | — | — | — | — | 3 | 3 | 1.98 |
| polyethylene glycol monostearate[6)] | — | — | — | — | 5 | 5 | 4 |
| polyoxyethylene sorbitan monooleate | — | — | — | 1.5[7)] | — | — | — |
| sorbitan monolaurate | — | — | — | — | — | — | — |
| lauric acid diethanolamide | — | — | — | — | — | — | — |
| stearic acid diethanolamide | — | — | — | — | — | — | — |
| coconut fatty acid diethanolamide. | — | — | — | — | — | — | — |
| hydrogenated oil | — | 5 | — | — | — | — | — |
| jojoba oil | — | — | — | — | — | — | — |
| castor oil | — | 20 | — | — | — | — | — |
| safflower oil | — | — | — | — | — | — | — |
| lanolin | — | — | — | — | — | — | 3 |
| lactic acid | — | — | — | — | — | — | — |
| isostearic acid | — | — | — | — | — | — | — |
| oleic acidr | — | — | — | — | — | — | — |
| sorbic acid | — | — | — | — | — | — | — |
| phosphoric acid. | — | — | — | — | — | — | — |
| dibasic sodium phosphate | — | — | — | — | — | — | — |
| sodium hydroxide | — | — | — | — | — | — | — |
| liquid petrolatum | — | — | — | — | — | — | 6 |
| light liquid isoparaffin | — | — | — | — | — | — | — |
| methyl parahydroxybenzoate | — | — | — | — | — | — | — |
| propyl parahydroxybenzoate | — | — | — | — | — | — | — |
| N-methacryloyl ethyl- N,N-dimethyl ammonium α-N-methyl carboxybetaine · butyl methacrylate copolymer | — | — | — | — | — | — | — |
| poly N,N'-dimethyl-3,5-methylene-piperidinium chloride | — | — | — | — | — | — | — |
| dimethylsiloxane · methylstearoxysiloxane copolymer | — | — | — | — | — | — | — |
| dimethylsiloxane · methyl(polyoxyethylene) siloxane copolymer | — | — | — | — | — | — | — |
| methyl polysiloxane | — | — | — | — | — | — | — |
| disodium edetate | — | — | — | — | — | — | 0.02 |
| phenoxyethanol. | — | — | — | — | — | — | — |
| zinc sulfate | — | — | — | — | — | — | — |
| magnesium sulfate. | — | — | — | — | — | — | — |
| water | — | — | — | — | — | — | — |

1)–7) in Table 34 indicate,
1)7EO,
2)3EO,
3)25EO,
4)60EO,
5)20EO,
6)10EO,
7)20EO.

TABLE 35

| | Example | | | | | | |
|---|---|---|---|---|---|---|---|
| | 129 | 130 | 131 | 132 | 133 | 134 | 135 |
| ingredient (° C.) | 80 | 80 | 70~80 | 80 | 80~85 | 82–85 | 80 |
| ingredient (kg) | | | | | | | |
| ethanol | — | — | 0.4 | — | — | — | — |
| isopropanol | — | — | — | — | — | — | — |
| lauryl alcohol | — | — | — | — | — | — | — |
| myristyl alcohol | — | — | — | — | 18.63 | — | — |
| cetanol | 36 | 29 | — | — | 18.63 | 54.46 | 19 |
| oleyl alcohol | — | — | — | — | — | — | — |
| arachyl alcohol | — | — | — | — | — | — | — |
| behenyl alcohol | — | — | — | — | — | — | — |
| cetostearyl alcohol | — | — | — | — | — | — | — |
| propylene glycol | — | — | — | — | — | — | 9.5 |
| 1,3-butylene glycol | — | — | — | — | — | — | — |
| 3-methyl-1,3-butandiol | — | — | — | — | — | — | — |
| diethylene glycol monoethyl ether | — | — | — | — | — | — | — |
| conc. glycerin | — | — | — | — | — | — | — |
| 70% sorbitol solution | — | — | — | 2 | — | — | — |
| distearyl dimethyl ammonium chloride | — | — | — | — | — | — | — |

TABLE 35-continued

| | Example | | | | | | |
|---|---|---|---|---|---|---|---|
| | 129 | 130 | 131 | 132 | 133 | 134 | 135 |
| dipolyoxyethylene oleyl methyl ammonium chloride | — | — | — | 20[1)] | — | — | — |
| stearyl dimethyl benzyl ammonium chloride[2)] | 14 | 2 | — | — | — | — | — |
| benzalkonium chloride | — | — | — | — | — | — | — |
| lauryl trimethyl ammonum chloride | — | — | 13[3)] | — | — | — | — |
| cetyl trimethyl ammonium chloride[4)] | 21 | — | — | 15 | 14.9 | 39.6 | 22 |
| cetyl trimethyl ammonium bromide | — | 37[5)] | — | — | — | — | — |
| stearyl trimethyl ammonium chloride | — | — | — | — | 18.63[6)] | — | — |
| stearyl trimethyl ammonium bromide | — | — | — | — | — | — | — |
| behenyl trimethyl ammonium chloride | — | — | — | — | — | — | — |
| cethyl trimethyl ammonium saccarinate | — | — | — | — | — | — | — |
| cetyl pyridinium chloride | — | — | — | — | — | — | — |

[1)–6)] in Table 35 indicate,
[1)]Content 75 wt. %, 2EO
[2)]Content, 90 wt. %,
[3)]Content, 30 wt. %,
[4)]Content, 70 wt. %,
[5)]Content, 70 wt. %,
[6)]Content, 60 wt. %.

TABLE 36

| | Example | | | | | | |
|---|---|---|---|---|---|---|---|
| | 129 | 130 | 131 | 132 | 133 | 134 | 135 |
| ingredient (kg) | | | | | | | |
| polyoxyethylene lauryl ether | — | 2[1)] | — | — | 1.24[2)] | — | — |
| polyoxyethylene cetyl ether | — | — | — | — | — | — | 12[3)] |
| polyoxyethylene oleyl ether | — | — | — | — | — | — | 4[4)] |
| polyoxyethylene nonylphenyl ether | — | — | — | — | — | — | — |
| polyoxyethylene hydrogenated castor oil | — | — | — | 8[5)] | — | — | — |
| polyoxyethylene almond oil | — | — | — | — | — | — | — |
| polyoxyethylene lanolin | — | — | — | — | — | 2.97[6)] | — |
| polyethylene glycol monostearate[7)] | 2 | — | — | — | — | 2.97 | — |
| polyoxyethylene sorbitan monooleate | — | — | — | — | — | — | — |
| sorbitan monolaurate | — | — | — | — | — | — | — |
| lauric acid diethanolamide | — | — | — | — | — | — | — |
| stearic acid diethanolamide | — | — | — | — | — | — | 32 |
| coconut fatty acid diethanolamide | — | — | 4 | 29 | — | — | — |
| hydrogenated oil | — | — | — | — | — | — | — |
| jojoba oil | — | — | — | — | — | — | — |
| castor oil | — | — | — | — | — | — | — |
| safflower oil | — | — | — | — | — | — | — |
| lanolin | 8 | 12 | — | — | 12.42 | — | — |
| lactic acid | — | — | — | — | — | — | 1.5[9)] |
| isostearic acid | 14 | — | — | — | — | — | — |
| oleic acidr | — | — | — | — | — | — | — |
| sorbic acid | — | — | — | — | — | — | — |
| phosphoric acid | — | — | — | 0.7[10)] | — | — | — |
| dibasic sodium phosphate | — | — | — | — | — | — | — |
| sodium hydroxide | — | — | — | — | — | — | — |
| liquid petrolatum | 5 | 17.98 | — | — | 15.53 | — | — |
| light liquid isoparaffin | — | — | — | — | — | — | — |
| methyl parahydroxybenzoate | — | — | 0.02 | — | — | — | — |
| propyl parahydroxybenzoate | — | — | 0.03 | — | — | — | — |
| N-methacryloyl ethyl-N,N-dimethyl ammonium $\alpha$-N-methyl carboxybetaine · butyl methacrylate copolymer | — | — | — | — | — | — | — |
| poly N,N'-dimethy-3,5-methylene.piperidinium chloride | — | — | 2[8)] | — | — | — | — |
| dimethylsiloxane · methylstearoxysiloxane copolymer | — | — | — | — | — | — | — |
| dimethylsiloxane · methyl(polyoxyethylene) siloxane copolymer | — | — | — | — | — | — | — |
| methyl polysiloxane | — | — | — | — | — | — | — |
| disodium edetate | — | 0.02 | — | — | — | — | — |
| phenoxyethanol. | — | — | — | — | — | — | — |
| zinc sulfate | — | — | — | — | — | — | — |

TABLE 36-continued

| | Example | | | | | | |
|---|---|---|---|---|---|---|---|
| | 129 | 130 | 131 | 132 | 133 | 134 | 135 |
| magnesium sulfate | — | — | — | — | — | — | — |
| water | — | — | 80.55 | 25.3 | — | — | — |

1)–10) in Table 36 indicate,
1) 23EO,
2) 25EO,
3) 9.12 kg (2EO) + 1.44 kg (6EO) + 1.44 kg (20EO),
4) 50EO,
5) 60EO,
6) 20EO,
7) 10EO,
8) Content, 40 wt. %,
9) Content, 90 wt. %,
10) Content, 85 wt. %

TABLE 37

| | Example | | | | | | |
|---|---|---|---|---|---|---|---|
| | 136 | 137 | 138 | 139 | 140 | 141 | 142 |
| ingredient (° C.) | 60–65 | 70 | 80 | 80 | 95–98 | 93~95 | 74–76 |
| ingredient (kg) | | | | | | | |
| ethanol | — | — | — | — | — | — | — |
| isopropanol | — | — | — | — | — | — | 3 |
| lauryl alcohol | — | 10 | — | — | — | — | — |
| myristyl alcohol | — | — | — | — | — | — | — |
| cetanol | — | 38 | 8 | 8 | — | — | — |
| oleyl alcohol | — | — | — | — | 0.7 | 0.5 | — |
| arachyl alcohol | — | — | — | — | — | — | — |
| behenyl alcohol | — | — | — | — | — | — | — |
| cetostearyl alcohol | 20 | — | — | — | — | — | — |
| propylene glycol | — | — | 14 | 16 | — | — | — |
| 1,3-butylene glycol | — | — | — | — | — | — | — |
| 3-methyl-1,3-butandiol | — | — | — | — | — | — | — |
| diethylene glycol monoethyl ether | — | — | — | — | — | — | — |
| conc. glycerin | — | — | — | — | — | — | — |
| 70% sorbitol solution | — | — | — | — | — | — | — |
| distearyl dimethyl ammonium chloride | — | — | — | — | — | — | — |
| dipolyoxyethylene oleyl methyl ammonium chloride | — | — | — | — | — | — | — |
| stearyl dimethyl benzyl ammonium chloride | — | — | — | — | — | — | — |
| benzalkonium chloride | — | — | — | — | — | — | — |
| lauryl trimethyl ammonum chloride[1)] | — | 24 | — | — | 0.98 | 1.48 | — |
| cetyl trimethyl ammonium chloride | — | — | 12[2)] | 21[2)] | 6.59[3)] | 9.88[3)] | — |
| cetyl trimethyl ammonium bromide | — | — | 11[4)] | — | — | — | — |
| stearyl trimethyl ammonium chloride | 40[5)] | — | — | — | — | — | — |
| stearyl trimethyl ammonium bromide | — | — | — | — | — | — | — |
| behenyl trimethyl ammonium chloride | 10[6)] | — | — | — | — | — | — |
| cethyl trimethyl ammonium saccarinate | — | — | — | — | — | — | — |
| cetyl pyridinium chloride | — | — | — | — | — | — | 3.9[8)] |

1)–8) in Table 37 indicate,
1) Content, 30 wt. %,
2) Content, 70 wt. %,
3) Content, 50 wt. %,
4) Content, 70 wt. %,
5) Content, 70 wt. %,
6) Content, 80 wt. %,
7) Content, 50 wt. %,
8) Content, 40 wt. %.

TABLE 38

| | Example | | | | | | |
|---|---|---|---|---|---|---|---|
| | 136 | 137 | 138 | 139 | 140 | 141 | 142 |
| ingredient (kg) | | | | | | | |
| polyoxyethylene lauryl ether | — | — | — | — | — | — | — |
| polyoxyethylene cetyl ether[1)] | 25[1)] | 28[5)] | 4[6)] | 4[7)] | — | — | |

TABLE 38-continued

| | Example | | | | | | |
|---|---|---|---|---|---|---|---|
| | 136 | 137 | 138 | 139 | 140 | 141 | 142 |
| polyoxyethylene oleyl ether | — | — | 4[8] | 4[9] | 8.03[2] | 6.61[3] | 6[4] |
| polyoxyethylene nonylphenyl ether | — | — | — | — | — | — | — |
| polyoxyethylene hydrogenated castor oil | — | — | — | — | — | — | — |
| polyoxyethylene almond oil | — | — | — | — | — | — | — |
| polyoxyethylene lanolin | — | — | — | — | — | — | — |
| polyethylene glycol monostearate | — | — | — | — | — | — | — |
| polyoxyethylene sorbitan monooleate | — | — | — | — | — | — | — |
| sorbitan monolaurate | — | — | — | — | — | — | — |
| lauric acid diethanolamide | — | — | — | — | — | — | — |
| stearic acid diethanolamide | — | — | 46 | 46 | — | — | — |
| coconut fatty acid diethanolamide | — | — | — | — | — | — | — |
| hydrogenated oil | — | — | — | — | — | — | — |
| jojoba oil | — | — | — | — | 2.3 | — | — |
| castor oil | — | — | — | — | — | — | — |
| safflower oil | — | — | — | — | — | — | 6 |
| lanolin | — | — | — | — | — | 4 | — |
| lactic acid | — | — | — | — | — | — | — |
| isostearic acid | — | — | — | — | — | — | — |
| oleic acidr | — | — | — | — | — | — | 0.33 |
| sorbic acid[10] | — | — | — | — | 0.1 | 0.15 | — |
| phosphoric acid[11] | — | — | 1 | 1 | 0.01 | 0.01 | — |
| dibasic sodium phosphate | — | — | — | — | — | — | 0.1 |
| sodium hydroxide | — | — | — | — | 0.04 | 0.06 | — |
| liquid petrolatum | — | — | — | — | 6 | 9 | 13 |
| light liquid isoaraffin | — | — | — | — | — | — | — |
| methyl parahydroxybenzoate | — | — | — | — | — | — | — |
| propyl parahydroxybenzoate | — | — | — | — | — | — | — |
| N-methacryloyl ethyl-N,N-dimethyl ammonium α-N-methyl carboxybetaine · butyl methacrylate copolymer | — | — | — | — | — | — | — |
| poly N,N'-dimethyl-3,5-methylene-piperidinium chloride | — | — | — | — | — | — | — |
| dimethylsiloxane · methylstearoxysioxane copolymer | 5 | — | — | — | — | — | — |
| dimethylsiloxane · methyl(polyoxyethylene) siloxane copolymer | — | — | — | — | — | — | — |
| methyl polysiloxane | — | — | — | — | — | — | — |
| disodium edetate | — | — | — | — | — | — | — |
| phenoxyethanol. | — | — | — | — | — | — | — |
| zinc sulfate | — | — | — | — | — | — | — |
| magnesium sulfate | — | — | — | — | — | — | — |
| water | — | — | — | — | 75.25 | 68.31 | 67.67 |

[1)–11)] in Table 38 indicate,
[1)]20 kg (5EO) + 5 kg (40EO),
[2)]2.36 kg (7EO) + 0.69 kg (15EO) + 0.98 kg (20EO) + 2.66 kg (30EO) + 1.34 kg (50EO),
[3)]3.88 kg (7EO) + 1.01 kg (15EO) + 1.72 kg (20EO),
[4)]5.3 kg (7EO) + 0.69 kg (13EO),
[5)]40EO,
[6)]20EO,
[7)]20EO,
[8)]50EO,
[9)]50EO,
[10)]Content, 85 wt.%,
[11)]Content, 85 wt.%.

TABLE 39

| | Example | | | | | | |
|---|---|---|---|---|---|---|---|
| | 143 | 144 | 145 | 146 | 147 | 148 | 149 |
| ingredient (° C.) | 80 | 50 | 80 | 80~85 | 80~85 | 80~85 | 80~85 |
| ingredient (kg) | | | | | | | |
| ethanol | — | 27 | — | — | — | — | — |
| isopropanol | 10 | — | — | — | — | — | — |
| lauryl alcohol | — | — | — | — | — | — | — |
| myristyl alcohol | — | — | — | — | — | — | — |
| cetanol | — | — | — | — | — | — | — |
| oleyl alcohol | — | — | — | — | — | — | — |
| arachyl alcohol | — | — | — | — | — | — | — |
| behenyl alcohol | — | — | — | — | — | — | — |

TABLE 39-continued

| | Example | | | | | | |
|---|---|---|---|---|---|---|---|
| | 143 | 144 | 145 | 146 | 147 | 148 | 149 |
| cetostearyl alcohol | — | — | — | — | — | — | — |
| propylene glycol | — | — | — | — | — | — | — |
| 1,3-butylene glycol | — | — | — | — | — | — | — |
| 3-methyl-1,3-butandiol | — | — | — | — | — | — | — |
| diethylene glycol monoethyl ether | — | — | 1.8 | — | — | — | — |
| conc. glycerin | — | — | 0.5 | 4.4 | 4.4 | 4.4 | 4.4 |
| 70% sorbitol solution | — | — | — | — | — | — | — |
| distearyl dimethyl ammonium chloride | — | — | — | — | — | — | — |
| dipolyoxyethylene oleyl methyl ammonium chloride[1] | — | 28 | — | — | — | 7 | 7 |
| stearyl dimethyl benzyl ammonium chloride | — | — | — | — | — | — | — |
| benzalkonium chloride | 4[2] | — | — | — | — | — | — |
| lauryl trimethyl ammonium chloride | 5[3] | — | — | — | — | — | — |
| cetyl trimethyl ammonium chloride[4] | — | — | — | 7 | 7 | — | — |
| cetyl trimethyl ammonium bromide | — | — | — | — | — | — | — |
| stearyl trimethyl ammonium chloride | — | 6[5] | 0.1[6] | — | — | — | — |
| stearyl trimethyl ammonium bromide | — | — | — | — | — | — | — |
| behenyl trimethyl ammonium chloride | — | — | — | — | — | — | — |
| cethyl trimethyl ammonium saccarinate[8] | — | — | — | 5 | 5 | 5 | 5 |
| cetyl pyridinium chloride | — | — | — | — | — | — | — |

[1]–[6] in Table 39 indicate,
[1]Content 75 wt.%, 2EO,
[2]Content, 50 wt.%,
[3]Content, 30 wt.%,
[4]Content, 50 wt.%,
[5]Content, 60 wt.%,
[6]Content, 35 wt.%.

TABLE 40

| | Example | | | | | | |
|---|---|---|---|---|---|---|---|
| | 143 | 144 | 145 | 146 | 147 | 148 | 149 |
| ingredient (kg) | | | | | | | |
| polyoxyethylene lauryl ether | 8[1] | — | 2.5[2] | — | 0.5[1] | — | — |
| polyoxyethylene cetyl ether | — | — | — | — | — | — | — |
| polyoxyethylene oleyl ether | — | — | — | — | — | — | — |
| polyoxyethylene nonylphenyl ether[3] | 8 | — | — | 0.5 | — | 0.5 | 0.4 |
| polyoxyethylene hydrogenated castor oil | — | — | — | — | — | — | — |
| polyoxyethylene almond oil | — | — | — | — | — | — | — |
| polyoxyethylene lanolin | — | — | — | — | — | — | — |
| polyethylene glycol monostearate | — | — | — | — | — | — | — |
| polyoxyethylene sorbitan monooleate | — | — | — | — | — | — | — |
| sorbitan monolaurate | — | 4 | — | — | — | — | — |
| lauric acid diethanolamide | 1 | — | — | — | — | — | — |
| stearic acid diethanolamide | — | — | — | — | — | — | — |
| coconut fatty acid diethanolamide | — | — | — | — | — | — | — |
| hydrogenated oil | — | — | — | — | — | — | — |
| jojoba oil | — | — | — | — | — | — | — |
| castor oil | — | — | — | — | — | — | — |
| safflower oil | — | — | — | — | — | — | — |
| lanolin | — | — | — | — | — | — | — |
| lactic acid[7] | — | — | — | 0.1 | 0.1 | 0.1 | 0.1 |
| isostearic acid | — | — | — | — | — | — | — |
| oleic acidr | — | — | — | — | — | — | — |
| sorbic acid | — | — | — | — | — | — | — |
| phosphoric acid | — | — | — | — | — | — | — |
| dibasic sodium phosphate | — | — | — | — | — | — | — |
| sodium hydroxide | — | — | — | — | — | — | — |
| liquid petrolatum | — | — | — | — | — | — | — |
| light liquid isoparaffin | — | 2 | — | — | — | — | — |
| methyl parahydroxybenzoate | — | — | 0.2 | — | — | — | — |
| propyl parahydroxybenzoate | — | — | 0.05 | — | — | — | — |
| N-methacryloyl ethyl- N,N-dimethyl ammonium α-N-methyl carboxybetaine · butyl methacrylate copolymer | — | 6[4] | — | — | — | — | — |
| poly N,N'-dimethyl-3,5-methylene-piperidinium chloride | — | — | — | — | — | — | — |
| dimethylsiloxane · methylstearoxysiloxane copolymer | — | — | — | — | — | — | — |

TABLE 40-continued

| | Example | | | | | | |
|---|---|---|---|---|---|---|---|
| | 143 | 144 | 145 | 146 | 147 | 148 | 149 |
| dimethylsiloxane · methyl(polyoxyethylene) siloxane copolymer | — | 23[5)] | — | — | — | — | — |
| methyl polysiloxane | — | — | 27[6)] | — | — | — | — |
| disodium edetate | 0.3 | — | — | — | — | — | — |
| phenoxyethanol | — | 4 | — | — | — | — | — |
| zinc sulfate | — | — | — | 22 | 22 | 22 | — |
| magnesium sulfate. | — | — | — | — | — | — | 30 |
| water | 63.7 | — | 67.85 | 61 | 61 | 61 | 53.1 |

1)–7) in Table 40 indicate,
1)25EO,
2)1.4 kg (2EO) + 1.1 kg (20EO),
3)11EO,
4)Content, 40 wt.%,
5)4 kg (15EO) + 8 kg (65EO) + 11 kg (250EO),
6)weight ratio, 350 cs:100,000 cs = about 1:1,
7)Content, 90 wt.%.

As illusted in the above-mentioned Examples, cationic surfactant may be used as mixture comprising alcohols (e.g. ethanol, IPA) instead of single cationic surfactant compound. In such case, the word, "alcohols", in this specification does not include alcohols that are contained in the mixture. Therefore, in the present invention, when the cationic surfactant are used as the above-mentioned mixture containing alcohol, at least one alcohol (for example, ethanol and IPA etc. except such ethanol and IPA etc. that are contained in the above-mentioned mixture) besides the alcohols that are contained in the above-mentioned mixture is further contained.

(Preparation of Hair Conditioners)

Examples 150–154

Initial water was heated to the temperature shown in Table 41. On the other hand, the composition for blending in hair conditioner obtained above (Examples 123, 126, 127 or 130) and parabens were mixed, and heated to the temperature shown in Table 41, and then dissolved homogeneously.

Next, this heated homogeneously dissolved material was added to the above-mentioned heated water with constant stirring and emulsified. Then the emulsion was cooled down to the temperature shown in Table 41 with constant stirring, perfume and, if necessary, 30% polypeptide aqueous solutions (PPT) were added. Finaly, purified water (add water) was added so as to adjust the total weight to be 100 kg, and mixed homogeneously. Thus, the hair conditioners of the present invention (Examples 150–154) were prepared. The heating temperature (C), ingredients and contents (kg) are shown in Table 41.

Examples 155,156

Disodium edetate, if necessary, was added to the initial water, and then heated as stirring to the temperature shown in Table 42. On the other hand, the composition for blending in hair conditioner obtained above (Example 133 or 134) was heated to the temperature shown in Table 42, and then dissolved homogeneously. Next, this heated homogeneously dissolved material was added to the above-mentioned heated water (or aqueous solution) with constant stirring and emulsified.

Then the emulsion was cooled down to the temperature shown in Table 42 with constant stirring. Finaly, purified water (add water) was added so as to adjust the total weight to be 100 kg, and mixed homogeneously. Thus, the hair conditioner of the present invention (Example 155,156) was prepared. The heating temperature (° C.), the cooling temperature (° C.), ingredients and contents (kg) are shown in Table 42.

TABLE 41

| | Example | | | | |
|---|---|---|---|---|---|
| | 150 | 151 | 152 | 153 | 154 |
| heating temperature (° C.) | 80~85 | 83~88 | 83~88 | 80~85 | 85~90 |
| cooling temperature (° C.) | 45 | 45~50 | 45~50 | 45 | 45~50 |
| ingredient (kg) | | | | | |
| composition blended in hair conditioner | Example 123 15 | Example 126 7 | Example 127 7 | Example 130 10 | Example 130 10 |
| parabens | 0.15 | 0.3 | 0.3 | 0.15 | 0.3 |
| perfume | proper amount | proper amount | proper amount | proper amount | proper amount |
| sodium edetate | — | — | — | — | — |
| 30% PPT | — | 20 | 20 | — | proper amount |
| initial water | 80 | 60 | 60 | 80 | 80 |

TABLE 42

| | Example | |
|---|---|---|
| | 155 | 156 |
| heating temperature (° C.) | 82~85 | 82~85 |
| cooling temperature (° C.) | 45 | 45 |
| ingredient (kg) | | |
| composition blended in hair conditioner | Example 133<br>16.1 | Example 134<br>10.1 |
| parabens | — | — |
| perfume | — | — |
| sodium edetate | 0.04 | — |
| 30% PPT | — | — |
| initial water | 80 | 80 |

(Preparation of 2-Bath Type of Treatments)

Examples 157

Preparation of Liquid 1 of 2-Bath Type of Treatment 58.85 kg of water, 7 kg of 1,3-butylene glycol, 4 kg of ethanol and 0.15 kg of parabens were added in order as stirring to 30 kg of the additive composition[1)], and mixed homogeneously. Thus, the Liquid 1 of 2-bath type of treatment of the present invention was prepared.

1) Ingredient (wt. %); 1,3-butylene Glycol (10), Carrageenan (4), Hydrolyzed Animal Protein (5), Parahydroxybenzoic Acid Ester (0.1), Water (80.9).

Preparation of Liquid 2 of 2-Bath Type of Treatment 64.85 kg of water was heated to 85–90° C. On the other hand, 20 kg of the composition for blending in hair conditioner (Examples 125) and 0.15 kg of parabens were mixed, and heated to 85–90° C., and then dissolved homogeneously. Next, this heated homogeneously dissolved material was added to the above-mentioned heated water with constant stirring and emulsified. Then the emulsion was cooled down to 45° C. with constant stirring, 15 kg of additive composition[2)] and proper amount of perfume were added. Finaly, water (add water) was added so as to adjust the total weight to be 100 kg, and mixed homogeneously. Thus, the Liquid 2 of 2-bath type of treatment of the present invention was prepared.

2) Ingredient (wt. %); Decamethyl Cyclopentasiloxane (56), Dimethyl Polysiloxane (24), Highly Polymerized Dimethyl Polysiloxane (20).

(Preparation of Waving Agent)

Example 158

Preparation of 5% Viscous Liquid

The composition for blending in waving agent (Example 135) was heated to about 83° C., and then dissolved homogeneously. On the other hand, water was heated to 83–85° C. Next, the above-mentioned homogeneously dissolved material was added as stirring to the heated water, and then mixed homogeneously. After the homogeneous mixture was cooled down to 46–48° C. with constant stirring, water (add water) was added so as to adjust the total weight to be 100 kg, and mixed homogeneously. Thus, 5% viscous liquid was prepared. Ingredients and contents (kg) are shown in Table 43.

Preparation of No. 1 Agents of Waving Agents

To 20 kg of 5% viscous liquid obtained above, 13 kg of 50 wt. % ammonium thioglycolate (ATG) rd and proper amount of strong ammonia solution were added at room temperature. Further, water (add water) was added so as to adjust the total weight to be 100 kg, and mixed homogeneously. Thus No. 1 agents of waving agents was prepared.

Preparation of No. 2 Agents of Waving Agents

To 20 kg of 5% viscous liquid obtained above, 8 kg of sodium bromate were added at room temperature. Further, water (add water) was added so as to adjust the total weight to be 100 kg, and mixed homogeneously. Thus No. 2 agent of waving agent was prepared.

Example 159–162

Preparation of 5% Viscous Liquid

5% viscous liquid was prepared in the same manner as Example 158 except that the composition for blending in waving agent (Example 136–139) was used instead of the composition for blending in waving agent (Example 135). The ingredients and contents (kg) are shown in Table 43.

Preparation of No. 1 Agents of Waving Agents

No. 1 agent of waving agent (Example 159–162) was prepared from the above-mentioned 5% viscous liquid in the same manner as Example 158.

Preparation of No. 2 Agents of Waving Agents

No. 2 agent of waving agent prepared in Example 158 was used as the No. 2 agent of waving agent in each Example 159–162.

TABLE 43

| 5% viscous liquid ingredient | Example | | | | |
|---|---|---|---|---|---|
| (kg) | 158 | 159 | 160 | 161 | 162 |
| composition blended in waving agent | Example 135<br>5 | Example 136<br>5 | Example 137<br>5 | Example 138<br>5 | Example 139<br>5 |
| initial water | 90 | 90 | 90 | 90 | 90 |

Example 163–166

Preparation of No. 1 Agents of Waving Agents

The composition for blending in a waving agent (Example 140–143), 50 wt. % ammonium thioglycolate (ATG), strong ammonia solution and water were mixed as stirring homogeneously at room temperature. Thus, No. 1 agent of waving agent (Example 163–166) was prepared. Ingredients and contents (kg) are shown in Table 44.

Preparation of No. 2 Agents of Waving Agents

The composition for blending in a waving agent (Example 140–142, and 135), sodium bromate and water were mixed as stirring homogeneously at room temperature. Thus No. 2 agent of waving agent (Example 163–166) was prepared. Ingredients and contents (kg) are shown in Table 44.

TABLE 44

| | Example | | | |
|---|---|---|---|---|
| ingredient (kg) | 163 | 164 | 165 | 166 |
| No. 1 agent | | | | |
| composition blended in waving agent | Example 140<br>2 | Example 141<br>2 | Example 142<br>2 | Example 143<br>5 |
| 50% ATG | 13 | 13 | 13 | 13 |
| strong ammonia solution | proper amount | proper amount | proper amount | proper amount |
| water | remaining volume | remaining volume | remaining volume | remaining volume |
| total amount | 100 | 100 | 100 | 100 |

TABLE 44-continued

| ingredient (kg) | Example 163 | Example 164 | Example 165 | Example 166 |
|---|---|---|---|---|
| No. 2 agent | | | | |
| composition blended in waving agent | Example 140 5 | Example 141 5 | Example 142 5 | Example 135 5 |
| sodium bromate | 8 | 8 | 8 | 8 |
| water | remaining volume | remaining volume | remaining volume | remaining volume |
| total amount | 100 | 100 | 100 | 100 |

(Preparation of Finishing Agents)

Example 167 and 168

The composition for blending in a finishing agent (Example 144 or 145), ethanol, parabens and water were added in order, and then mixed as stirring homogeneously. Thus finishing agent (Example 167 and 168) of the present invention was prepared. Ingredients and contents (kg) are shown in Table 45.

TABLE 45

| ingredient (kg) | Example 167 | Example 168 |
|---|---|---|
| composition blended in finishing agent | Example 144 10 | Example 145 10 |
| ethanol | proper amount | 10 |
| parabens | 0.1 | 0.1 |
| water | proper amount | remaining volume |
| total amount | 100 | 100 |

(Preparation of Deodorizing Rinse Liquids)

Example 169 and 170

The composition for blending in deodorizing rinse liquid (Example 146 or 147), additive composition, 10% lactic acid and initial water were added, and then mixed as stirring homogeneously to prepare solution. Next, perfume and aromatic material dispersants were added, and then water (add water) was further added so as to adjust the total weight to be 100 kg, and mixed homogeneously. Thus, the deodorizing rinse liquid of the present invention was prepared. The ingredients and contents (kg) are shown in Table 46.

(Preparation of Intermediate Treating Agents for Permanents)

Example 171

Intermediate treating agent for permanents of the present invention was prepared in the same manner as Example 169 and 170 except that the composition for blending in intermediate treating agent for permanents (Example 149) was used instead of the composition for blending in deodorizing rinse liquid. The ingredients and contents (kg) are shown in Table 46.

(Preparation of the Compositions for Blending in Hair Treating Agents)

Examples 172

66 kg of ethanol, 15 kg of dipolyoxyethylene oleyl methyl ammonium chloride, 3.01 kg of stearyl trimethyl ammonium chloride, 2 kg of sorbitan monolaurate, 12 kg of dimethylsiloxane.methyl (polyoxyethylene) siloxane copolymer and 2 kg of phenoxyethanol were mixed as stirring homogeneously. Thus, the composition for blending in hair treating agent of the present invention was prepared.

TABLE 46

| ingredient (kg) | Example 169 | Example 170 | Example 171 |
|---|---|---|---|
| compositions blended in deodorizing rinse liquids or compositions blended in intermediate treating agents for permanents | Example 146 25 | Example 147 4.5 | Example 149 25 |
| additive composition[-1)] | 10 | 10 | 10 |
| 10% lactic acid | 0.6 | 0.6 | 0.6 |
| perfume | proper amount | proper amount | proper amount |
| aromatic material dispersants[2)] | proper amount | proper amount | proper amount |
| initial water | 40 | 40 | 40 |

[1)] and [2)] in Table 46 indicate,
[1)]Ingredient (wt. %); dimethyl diallyl ammonium chloride · acrylamide copolymer (35), polyoxyethylene castor oil (1), 1,3-butylene glycol (3), methyl parahydroxybenzoate (0.1), isopropyl parahydroxybenzoate (0.05), dibasic sodium phosphate (0.2), disodium edetate (0.1), water (60.55),
[2)]polyoxyethylene (18E0) nonylphenyl ether.

(Preparation of the Compositions for Blending in Hair Treating Agents)

Examples 172

Polyoxyethylene oleyl ether [2.67 kg (30 EO)+1.33 kg (50 EO)] and 13.33 kg of water were mixed as stirring at 80° C. to prepare homogeneously dissolved material. Next, 13.33 kg of ice was added to the above-mentioned homogeneously dissolved material, and then the mixture was cooled below 30° C. To this, 66.67 kg of the aforementioned composition for blending in hair conditioner (Example 141) was added. Finally, water (add water) was further added so as to adjust the total weight to be 100 kg, and mixed homogeneously. Thus, the composition for blending in hair treating agent of the present invention was prepared.

(Preparation of Waving Agent)

Example 173

Preparation of No. 1 Agents of Waving Agents 2 kg of the composition for blending in a waving agent (Example 172), 13 kg of 50 wt. % ATG, proper amount of strong ammonia solution and such amount of water as the total weight of the waving agent was adjusted to be 100 kg were mixed homogeneously by stirring at room temperature. Thus, No. 1 agent of waving agent was prepared.

Preparation of No. 2 Agents of Waving Agents 5 kg of composition for blending in waving agent (Example 172), 8 kg of sodium bromate and such amount of water as the total weight of the waving agent was adjusted to be 100 kg were mixed homogeneously by stirring at room temperature. Thus, No. 2 agent of waving agent was prepared.

According to the following hair treating method, the organoleptic tests about the waving agent obtained above (Example 173) were carried out. From the results of the organoleptic tests, it was found that penetrating ability into hair and moisturizing ability to hair were excellent, the wave formation was smooth, and firmly rooted and no uneven wave was formed. Further, it was found that the treated hair was not damaged, and the formed wave was pleasant to the touch and beautiful.

(The Organoleptic Tests about Hair Treating Effects of the Hair Treating Agents)

Hair treatings were carried out to 50 monitors by the following methods. And the results of the organoleptic tests about hair treating effects (i.e. feel when used) of the hair treating agents were obtained. The results of organoleptic tests were summarized in Table 47 and 48.

The Method for Hair Treating with Hair Conditioners

In a Case of 1-Bath Type of Treatment

After ordinary shampoo, a specimen of each hair conditioners (Examples 150–156) was applied to hair and spread by combing, and then rinsed and dried using a dryer.

In a Case of 2-Bath Type of Treatment

After ordinary shampoo, the Liquid 1 of 2-bath type of treatment (Example 157) was applied to hair. Next, without washing out the Liquid 1, the Liquid 2 of 2-bath type of treatment was applied to hair, and then rinsed, and finally dried using a dryer.

The Method for Hair Treating with Waving Agents

No. 1 agent of the waving agents (Example158–166 and 173) was applied to hair and spread by combing, and the hair was wound to a rod and left for 7 minutes at 45° C. Then, No. 2 agent was applied by an applicator and left for 7 minutes. Repeatedly, No. 2 agent was applied by an applicator and left for 7 minutes. Next, the rod was removed, and the hair was rinsed and dried using a dryer.

The Method for Hair Treating with Finishing Agents

The finishing agent (Example 167 or 168) was applied to hair and spread.

The Method for Hair Treating with Deodorizing Rinse Liquids

40–60 mL of the deodorizing rinse liquid (Example 169 or 170) was applied and spread evenly to the whole of hair when the process time of the No. 1 agent of the waving agent had finished.

The Method for Hair Treating with Intermediate Treating Agents for Permanents

40–60 mL of the intermediate treating agent for permanents (Example 171) was applied and spread evenly to the whole of hair when the process time of the No. 1 agent of the waving agent had finished.

TABLE 47

| feel when used | hair treating agent (Example) | | | | | | | | | | |
|---|---|---|---|---|---|---|---|---|---|---|---|
| and functionality | 150 | 151 | 152 | 153 | 154 | 155 | 156 | 157 | 158 | 159 | 160 |
| pleasant sense of touch to the hair | ○ | ◎ | ◎ | Δ | Δ | ◎ | ◎ | ◎ | ◎ | ◎ | ◎ |
| slightly oily feel | ○ | Δ | Δ | ◎ | ◎ | ○ | Δ | ◎ | Δ | Δ | Δ |
| moist feel | Δ | ○ | ◎ | ◎ | ◎ | ○ | ○ | Δ | Δ | Δ | Δ |
| soft feel | Δ | ◎ | ◎ | ○ | ○ | ◎ | ◎ | Δ | ○ | ◎ | ○ |
| smooth feel | ◎ | Δ | Δ | Δ | Δ | Δ | Δ | ◎ | ◎ | ◎ | ○ |
| smooth combing | ○ | ○ | ○ | ◎ | ◎ | ○ | ○ | ◎ | Δ | Δ | Δ |
| moisturizing ability | Δ | Δ | Δ | Δ | Δ | Δ | Δ | Δ | ◎ | Δ | ◎ |
| easy hair care | ○ | ◎ | ◎ | ○ | Δ | ◎ | ◎ | ○ | ○ | ○ | ○ |
| long-lasting treatment effects | — | — | — | — | — | — | — | ◎ | — | — | — |
| less harsh smell of ammonia | — | — | — | — | — | — | — | — | ◎ | ○ | ◎ |
| no unevenness of wave | — | — | — | — | — | — | — | — | ◎ | ◎ | ◎ |
| firmly rooted wave formation | — | — | — | — | — | — | — | — | ◎ | ○ | ◎ |
| smooth wave formation | — | — | — | — | — | — | — | — | ○ | ○ | ○ |
| eliminating ability of unpleasant odors | — | — | — | — | — | — | — | — | — | — | — |
| adhesiveness of wave | — | — | — | — | — | — | — | — | — | — | — |

TABLE 48

| feel when used | hair treating agent (Example) | | | | | | | | | | |
|---|---|---|---|---|---|---|---|---|---|---|---|
| and functionality | 161 | 162 | 163 | 164 | 165 | 166 | 167 | 168 | 169 | 170 | 171 |
| pleasant sense of touch to the hair | ◎ | ◎ | ◎ | ◎ | 502 | ○ | ○ | ○ | — | — | — |
| slightly oily feel | Δ | Δ | ○ | ◎ | ◎ | Δ | ○ | ○ | — | — | — |
| moist feel | Δ | Δ | ○ | ○ | ○ | Δ | Δ | Δ | — | — | — |
| soft feel | ○ | ○ | ◎ | ◎ | ◎ | ◎ | Δ | Δ | — | — | — |
| smooth feel | ◎ | ◎ | Δ | Δ | Δ | Δ | ◎ | ◎ | — | — | — |
| smooth combing | Δ | Δ | ○ | ○ | ○ | Δ | ◎ | ◎ | — | — | — |
| moisturizing ability | ◎ | ◎ | ◎ | ◎ | ◎ | ◎ | Δ | Δ | — | — | — |
| easy hair care | ○ | ○ | ○ | ○ | ○ | Δ | ◎ | ◎ | — | — | — |
| long-lasting treatment effects | — | — | — | — | — | — | — | — | — | — | — |
| less harsh smell of ammonia | ◎ | ◎ | — | — | — | — | — | — | — | — | — |
| no unevenness of wave | ◎ | ◎ | ◎ | ◎ | ◎ | ◎ | — | — | — | — | — |
| firmly rooted wave formation | ◎ | ◎ | ◎ | ◎ | ◎ | ◎ | — | — | — | — | — |
| smooth wave formation | ○ | ○ | ◎ | ◎ | ◎ | ○ | — | — | — | — | — |
| eliminating ability of unpleasant odors | — | — | — | — | — | — | — | — | ◎ | ◎ | ◎ |
| adhesiveness of wave | — | — | — | — | — | — | — | — | ◎ | ◎ | ◎ |

In Table 47 and 48,
◎ indicates "very good",
○ indicates "good" and
Δ indicates "normal".

As clearly understood from the results of the above-mentioned Examples, the compositions for blending in hair treating agents of the present embodiment are prepared by selecting and combining adequately the ingredients which are cheap and easy to purchase so as to display excellent hair treating effects. Therefore, the compositions for blending in hair treating agents of the present invention can be produced by lower cost and easily.

Since the hair treating agents of the present embodiment are prepared using above-mentioned compositions for blending in hair treating agents of the present invention, the costs for production are low, further, have excellent feels when used such as the sense of touch to the hair, slightly oily feel, moist feel, soft feel, smooth feel, smooth combing, and have excellent functionalities such as conditioning ability (easiness of hair care), long-lasting treatment effects, moisturizing ability, less harsh smell (of ammonia) in waving agent, no uneven and firmly rooted wave formation, eliminating ability of unpleasant odors (when permanents are applied), adhesiveness of wave etc. Further, in the preparation process of hair treating agentsince it is possible by using the compositions for blending in a hair treating agents of the present invention to blend alcohols, cationic surfactants and nonionic surfactants etc. at a time, the production process may be remarkably simplified.

What is claimed is:

1. A composition blended in a hair treating agent, comprising:

an alcohol and an ingredient wherein the content of alcohol in the composition blended in the hair treating agent is A wt %, A satisfying the equation of $0.5 \leqq A \leqq 90$, wherein said alcohol is ethanol and D-manitol, said ingredient is dimethyl diallyl ammonium chloride-.acrylamide copolymer, trimethyiglycine, methyl parahydroxybenzoate and water.

2. A composition blended in a hair treating agent, comprising:

an alcohol and an ingredient wherein the content of alcohol in the composition blended in the hair treating agent is A wt %, A satisfying the equation of $0.5 \leqq A \leqq 90$, wherein said alcohol is 1,3-butylene glycol and said ingredient is vinyl methyl ether.ethyl maleate copolymer.

3. A composition blended in a hair treating agent, comprising:

alcohols and ingredients wherein the content of alcohol in the composition blended in the hair treating agent is A wt %, A satisfying the equation of $0.5 \leqq A \leqq 90$, wherein said alcohols are ethanol and 1,3-butylene glycol and said ingredients are/vinyl acetate crotonic acid copolymer, octylamide acrylate.hydroxypropyl, acrylate.butylaminoethyl methacrylate copolymer, 2-amino-2-methylpropanol, methyl parahydroxybenzoate and water.

4. A composition blended in a hair treating agent, comprising:

an alcohol and ingredients wherein the content of alcohol in the composition blended in the hair treating agent is A wt %, A satisfying the equation of $0.5 \leqq A \leqq 90$, wherein said alcohol is ethanol and dipropylene glycol and said ingredients are polyvinylpyrrolidone, N-methacryloyl ethyl-N, N-dimethyl ammonium α-N-methyl carboxybetaine.alkyl methacrylate copolymer and water.

5. A composition blended in a hair treating agent, comprising:

an alcohol and ingredients wherein the content of alcohol in the composition blended in the hair treating agent is A wt %, A satisfying the equation of $0.5 \leqq A \leqq 90$, wherein said alcohol is ethanol and said ingredients are carboxyvinylpolymer, methyl parahydroxybenzoate, propyl parahydroxybenzoate and water.

6. A composition blended in a hair treating agent, comprising:

an alcohol an anionic surfactant nonionic surfactants wherein an alcohol content is B wt % and a content of the anionic surfactant is C wt %, wherein B and C satisfy the equation of $$0.1 \leqq B \leqq 90,$$

$$0.05 \leqq C \leqq 65 \text{ and}$$

$$B+C \leqq 100,$$

wherein said alcohol is cetanol, and said anionic surfactant is sodium lauryl sulfate, said nonionic surfactants are polyoxyethylene lauryl ether and polyoxyethylene oleyl ether.

7. A composition blended in a hair treating agent, comprising:

an alcohol an anionic surfactant nonionic surfactants wherein an alcohol content is B wt % and a content of the anionic surfactant is C wt %, wherein B and C satisfy the equation of $$0.1 \leqq B \leqq 90,$$

$$0.05 \leqq C \leqq 65 \text{ and}$$

$$B+C \leqq 100,$$

wherein said alcohol is lauryl alcohol and cetanol, said anionic surfactant is sodium lauryl sulfate, said nonionic surfactants are polyoxyethylene lauryl ether and polyoxyethylene oleyl ether and water.

8. A composition blended in a hair treating agent, comprising:

an alcohol an anionic surfactant a nonionic surfactant wherein an alcohol content is B wt % and a content of the anionic surfactant is C wt %, wherein B and C satisfy the equation of $$0.1 \leq B \leq 90,$$

$$0.05 \leq C \leq 65 \text{ and}$$

$$B+C \leq 100$$

wherein said alcohol is lauryl alcohol and cetanol, said anionic surfactant is sodium lauryl sulfate , said nonionic surfactant is polyoxyethylene cetyl ether and water.

9. A composition blended in a hair treating agent, comprising:

an alcohol an anionic surfactant nonionic surfactants a polymer an inorganic alkaline agent wherein an alcohol content is B wt % and a content of the anionic surfactant is C wt %, wherein B and C satisfy the equation of $$0.1 \leq B \leq 90,$$

$$0.05 \leq C \leq 65 \text{ and}$$

$$B+C \leq 100$$

wherein said alcohols are lauryl alcohol, cetanol, stearyl alcohol and behenyl alcohol, said anionic surfactant is sodium lauryl sulfate, said inorganic alkaline agent is sodium hydroxide, said nonionic surfactants are polyoxyethylene lauryl ether and polyoxyethylene oleyl ether and said polymer is polypropylene glycol.

10. A composition blended in a hair treating agent, comprising:

an alcohol and an anionic surfactant nonionic surfactants a hydrocarbon wherein an alcohol content is B wt % and a content of the anionic surfactant is C wt %, wherein B and C satisfy the equation of $$0.1 \leq B \leq 90,$$

$$0.05 \leq C \leq 65 \text{ and}$$

$$B+C \leq 100,$$

wherein said alcohols are lauryl alcohol and cetostearyl alcohol, said anionic surfactant is sodium N-myristoyl methyl taurate, said nonionic surfactants are polyoxyethylene cetyl ether, polyoxyethylene stearyl ether, and polyoxyethylene oleyl ether, said hydrocarbon is liquid petrolatum and water.

11. A composition blended in a hair treating agent, comprising:

an alcohol an anionic surfactant nonionic surfactants an organic base an ampohteric surfactant a sequestering agent wherein an alcohol content is B wt % and a content of the anionic surfactant is C wt %, wherein B and C satisfy the equation of $$0.1 \leq B \leq 90,$$

$$0.05 \leq C \leq 65 \text{ and}$$

$$B+C \leq 100$$

wherein said alcohol is isopropanol, said anionic surfactant is triethanolamine polyoxyethylene lauryl ether sulfate, said nonionic surfactants are polyoxyethylene lauryl ether and polyoxyethylene lanolin, said organic base is triethanolamine, said amphoteric surfactant is 2-alkyl N-carboxymethyl N-hydroxyethyl imidazolinium betaine, said sequestering agent is 1-hydroxyethane-1-1'-diphosphonic acid and water.

12. A composition blended in a hair treating agent, comprising:

an alcohol an inorganic acid nonionic surfactant an amophoteric surfactant a sequestering agent a perfume a paraben wherein an alcohol content is B wt % and a content of the inorganic acid is C wt %, wherein B and C satisfy the equation of $$0.1 \leq B \leq 90,$$

$$0.05 \leq C \leq 65 \text{ and}$$

$$B+C \leq 100$$

wherein said alcohol is glycerin, said inorganic acid is phosphoric acid, said nonionic surfactants are polyoxyethylene oleyl ether and cocodimethyl amine oxide, said amphoteric surfactant is cocoyl amide propyldimethyl glycine, said sequestering agent is disodium edetate, said perfume is orange oil, said paraben is methyl parahydroxybenzoate and water.

13. A composition blended in a hair treating agent, comprising:

an alcohol an inorganic acid a nonionic surfactant a polymer a sequestering agent parabens wherein an alcohol content is B wt % and a content of the inorganic acid is C wt %, wherein B and C satisfy the equation of $$0.1 \leqq B \leqq 90,$$

$$0.05 \leqq C \leqq 65 \text{ and}$$

$$B+C \leqq 100$$

wherein said alcohol is 1,3-butylene glycol, said inorganic acid is dibasic sodium phosphate, said nonionic surfactant is polyoxyethylene castor oil, said polymer is dimethyl diallyl ammonium chloride-.acrylamide copolymer, said sequestering agent is disodium edetate, said parabens are (iso)propyl parahydroxybenzoate and methyl parahydroxybenzoate and water.

14. A composition blended in a hair treating agent, comprising:

an alcohol an inorganic alkaline agent a polymer a organic acid wherein an alcohol content is B wt % and a content of the inorganic alkaline agent is C wt %, wherein B and C satisfy the equation of $$0.1 \leqq B \leqq 90,$$

$$0.05 \leqq C \leqq 65 \text{ and}$$

$$B+C \leqq 100$$

wherein said alcohols are ethanol and glycerin, said inorganic alkaline agent is sodium hydroxide, said polymer is hydroxyethyl cellulose, said organic acid is glycolic acid and water.

15. A composition blended in a hair treating agent, comprising:

an alcohol an inorganic acid a polymer, an organic acid, a nitrogen containing solvent wherein an alcohol content is B wt % and a content of the inorganic acid is C wt %, wherein B and C satisfy the equation of $$0.1 \leqq B \leqq 90,$$

$$0.05 \leqq C \leqq 65 \text{ and}$$

$$B+C \leqq 100$$

wherein said alcohols are ethanol and benzyl alcohol, said inorganic acid is phosphoric acid, said polymer is carboxyvinyl polymer, an organic acid is tartaric acid, a nitrogen containing solvent is N-methyl-2pyrrolidone and water.

16. A composition blended in a hair treating agent, comprising:

an alcohol an anionic surfactant nonionic surfactants parabens wherein an alcohol content is B wt % and a content of the anionic surfactant is C wt %, wherein B and C satisfy the equation of $$0.1 \leqq B \leqq 90,$$

$$0.05 \leqq C \leqq 65 \text{ and}$$

$$B+C \leqq 100$$

wherein said alcohols are propylene glycol and glycerin, said anionic surfactant is polyoxyethylene oleylether phosphate, and said nonionic surfactants are polyoxyethylene hydrogenated castor oil, polyoxyethylene cocoalkyl amine and polyoxyethylene.polyoxypropylene cetyl ether, and said parabens are (iso)propyl parahydroxybenzoate and methyl parahydroxybenzoate.

17. A composition blended in a hair treating agent, comprising:

an alcohol and a cationic surfactant wherein the respective content of alcohols is D wt % and content of cationic surfactants is E wt %, D and E satisfy the equation of $$0.5 \leqq D \leqq 85,$$

$$1 \leqq E \leqq 30 \text{ and}$$

$$D+E \leqq 100$$

wherein said alcohols are glycerin and cetanol, said cationic surfactants are stearyl trimethyl ammonium chloride and behenyl trimethyl ammonium chloride.

18. A composition blended in a hair treating agent, comprising:

an alcohol and a cationic surfactant an amphoteric surfactant an inorganic acid a sequestering agent wherein the respective content of alcohols is D wt % and content of cationic surfactants is E wt %, D and E satisfy the equation of $$0.5 \leqq D \leqq 85,$$

$$1 \leqq E \leqq 30 \text{ and}$$

$$D+E \leqq 100$$

wherein said alcohol is D-mannitol, said cationic surfactants is lauryl pyridinium chloride and said amphoteric surfactant is lauryl dimethylaminoacetic acid betaine, said inorganic acid is phosphoric acid, said sequestering agent is pentasodium diethylenetriamine pentaacetate and water.

19. A composition blended in a hair treating agent, comprising:

an alcohol an ingredient and a cationic surfactant wherein the respective content of alcohols is D wt % and content of cationic surfactants is E wt %, D and E satisfy the equation of $$0.5 \leqq D \leqq 85,$$

$$1 \leqq E \leqq 30 \text{ and}$$

$$D+E \leqq 100$$

wherein said alcohol is sorbit, said cationic surfactants is cetyl trimethyl ammonium saccarinate and said ingredient is 2-alkyl N-carboxymethyl N-hydroxyethyl imidazolinium betaine,disodium phosphate, disodium edetate and water.

20. A composition blended in a hair treating agent, comprising:

an alcohol an ingredient and a cationic surfactant wherein the respective content of alcohols is D wt % and content of cationic surfactants is E wt %, D and E satisfy the equation of $$0.5 \leqq D \leqq 85,$$

$$1 \leqq E \leqq 30 \text{ and}$$

$$D+E \leqq 100$$

wherein said alcohol is ethanol, said cationic surfactants is cetyl trimethyl ammonium chloride and said ingredients are citric acid, methyl parahydroxybenzoate, propyl parahydroxybenzoate, carboxyvinyl polymer and water.

21. A composition blended in a hair treating agent, comprising:

an alcohol a cationic surfactant, and a non-ionic surfactant wherein the alcohol content is F wt %, cationic surfactant content is G wt %, and nonionic surfactant content is H wt %, F, G and H satisfy the equation of $$0.1 \leqq F \leqq 85,$$

$$0.01 \leqq G \leqq 45,$$

$$0.1 \leqq H \leqq 60 \text{ and}$$

$$F+G+H \leqq 100,$$

wherein alcohol is cetanol, said cationic surfactant is cetyl trimethyl ammonium bromide, and said nonionic surfactants are polyoxyethylene lanolin and polyethylene glycol monostearate.

22. A composition blended in a hair treating agent, comprising:

an alcohol a cationic surfactant, and a non-ionic surfactant an inorganic acid wherein the alcohol content is F wt %, cationic surfactant content is G wt %, and nonionic surfactant content is H wt %, F, G and H satisfy the equation of $$0.1 \leqq F \leqq 85,$$

$$0.01 \leqq G \leqq 45,$$

$$0.1 \leqq H \leqq 60 \text{ and}$$

$$F+G+H \leqq 100,$$

wherein alcohols are cetanol and propylene glycol, said cationic surfactant is cetyl trimethyl ammonium chloride, said nonionic surfactants are polyoxyethylene cetyl ether, polyoxyethylene oleyl ether and stearic acid diethanolamide and said inorganic acid is lactic acid.

23. A composition blended in a hair treating agent, comprising:

an alcohol a cationic surfactant, and a non-ionic surfactant a polymer wherein the alcohol content is F wt %, cationic surfactant content is G wt %, and nonionic surfactant content is H wt %, F, G and H satisfy the equation of $$0.1 \leqq F \leqq 85,$$

$$0.01 \leqq G \leqq 45,$$

$$0.1 \leqq H \leqq 60 \text{ and}$$

$$F+G+H \leqq 100,$$

wherein said alcohols is cetostearyl alcohol, said cationic surfactants are stearyl trimethyl ammonium chloride and behenyl trimethyl ammonium chloride, said nonionic surfactant is polyoxyethylene cetyl ether and said polymer is dimethylsiloxane.methylstearoxysiloxane copolymer.

24. A composition blended in a hair treating agent, comprising:

an alcohol a cationic surfactant, and a non-ionic surfactant wherein the alcohol content is F wt %, cationic surfactant content is G wt %, and nonionic surfactant content is H wt %, F, C and H satisfy the equation of $$0.1 \leqq F \leqq 85,$$

$$0.01 \leqq G \leqq 45,$$

$$0.1 \leqq H \leqq 60 \text{ and}$$

$$F+G+H \leqq 100,$$

wherein said alcohols are lauryl alcohol and cetanol, said cationic surfactant is lauryl trimethyl ainmonium chloride, said nonionic surfactant is polyoxyethylene cetyl ether.

25. A composition blended in a hair treating agent, comprising:

an alcohol a cationic surfactant a non-ionic surfactant and an ingredient wherein the alcohol content is F wt %, cationic surfactant content is G wt %, and nonionic surfactant content is H wt %, F, G and H satisfy the equation of $$0.1 \leqq F \leqq 85,$$

$$0.01 \leqq G \leqq 45,$$

$$0.1 \leqq H \leqq 60 \text{ and}$$

$$F+G+H \leqq 100,$$

wherein said alcohol is oleyl alcohol, said cationic surfactants are lauryl trimethyl ainmonium chloride and cetyl trimethyl ammonium chloride, said nonionic surfactant is polyoxyethylene oleyl ether and said ingredients are jojoba oil, sorbic acid, phosphoric acid, sodium hydroxide, liquid petrolatum and water.

26. A composition blended in a hair treating agent, comprising:

an alcohol a cationic surfactant a non-ionic surfactant and an ingredient wherein the alcohol content is F wt %, cationic surfactant content is G wt %, and nonionic surfactant content is H wt %, F, G and H satisfy the equation of $$0.1 \leqq F \leqq 85,$$

$$0.01 \leqq G \leqq 45,$$

$$0.1 \leqq H \leqq 60 \text{ and}$$

$$F+G+H \leqq 100,$$

wherein said alcohols is oleyl alcohol, said cationic surfactant are lauryl trimethyl ammonium chloride and cetyl trimethyl ammonium chloride, said nonionic surfactant is polyoxyethylene oleyl ether and said ingredients are lanolin, sorbic acid, phosphoric acid, sodium hydroxide, liquid petrolatum and water.

27. A composition blended in a hair treating agent, comprising:

an alcohol a cationic surfactant a non-ionic surfactant and an ingredient wherein the alcohol content is F wt %, cationic surfactant content is G wt %, and nonionic surfactant content is H wt %, F, G and H satisfy the equation of $$0.1 \leqq F \leqq 85,$$

$$0.01 \leqq G \leqq 45,$$

$$0.1 \leqq H \leqq 60 \text{ and}$$

$$F+G+H \leqq 100,$$

wherein said alcohols is glycerin, said cationic surfactants is cetyl trimethyl ammonium chloride and cethyl trimethyl ammonium saccarinate, said non-ionic surfactant is polyoxyethylene lauryl ether and said ingredients are lactic acid, zinc sulfate and water.

28. A composition blended in a hair treating agent, comprising:

an alcohol a cationic surfactant a non-ionic surfactant and an ingredient wherein the alcohol content is F wt %, cationic surfactant content is G wt %, and nonionic surfactant content is H wt %, F, G and H satisfy the equation of $$0.1 \leqq F \leqq 85,$$

$$0.01 \leqq G \leqq 45,$$

$$0.1 \leqq H \leqq 60 \text{ and}$$

$$F+G+H \leqq 100,$$

wherein said alcohol is ethanol, cationic surfactants are dipolyoxyethylene oleyl methyl ammonium chloride and stearyl trimethyl ammonium chloride, said nonionic surfactant is sorbitan monolaurate and said ingredient are dimethylsiloxane.methyl (polyoxyethylene) siloxane copolymer and phenoxyethanol.

* * * * *